United States Patent
Sampath et al.

(10) Patent No.: US 6,498,142 B1
(45) Date of Patent: *Dec. 24, 2002

(54) MORPHOGEN TREATMENT FOR CHRONIC RENAL FAILURE

(75) Inventors: Kuber T. Sampath, Holliston; Charles M. Cohen, Weston, both of MA (US)

(73) Assignee: Curis, Inc., Cambridge, MA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/643,321

(22) Filed: May 6, 1996

(51) Int. Cl.$^7$ .................. A61K 38/04; A61K 38/07; A61K 38/16

(52) U.S. Cl. .............. 514/12; 514/21; 530/300; 530/350; 530/351; 424/85.1

(58) Field of Search ............ 514/12, 21; 530/300, 530/350, 351; 424/85.1

(56) References Cited

U.S. PATENT DOCUMENTS

| | | | |
|---|---|---|---|
| 5,723,441 A | * | 3/1998 | Higley et al. ............ 514/12 |
| 5,849,686 A | * | 12/1998 | Kuberasampath et al. ..... 514/2 |
| 5,879,908 A | * | 3/1999 | Laping et al. ............ 435/69.1 |
| 6,120,760 A | * | 9/2000 | Hotten et al. ............ 424/85.1 |

FOREIGN PATENT DOCUMENTS

| | | |
|---|---|---|
| CA | 1128881 | 8/1982 |
| WO | WO 94/03200 | 2/1992 |
| WO | WO 92/15323 | 9/1992 |
| WO | WO 93/04692 | 3/1993 |
| WO | WO 93/05172 | 3/1993 |
| WO | WO 93/05751 | 4/1993 |
| WO | WO 94/03075 | 2/1994 |
| WO | WO 94/03600 | 2/1994 |
| WO | WO 94/06449 | 3/1994 |
| WO | 94/06449 | * 3/1994 |
| WO | WO 94/20539 | 9/1994 |
| WO | WO 95/08621 | 3/1995 |
| WO | WO 95/11983 | 5/1995 |

OTHER PUBLICATIONS

Vukicevic et al. (1994), "Recombinant Human OP–1 (BMP–7) Prevents Rapid Loss of Glomerular Function and Improves Mortality Associated with Chronic Renal Failure," *J. Am. Soc. Nephrol.* 7(9):1867 (Abstract A3102).

Avner and Sweeney, Polypeptide growth factors in metanephric growth and segmental nephron differentiation,: *Pediatr. Nephrol.*, 4:372–377 (1990).

Bard et al., "Towards a Genetic Basis for Kidney Development," *Mech. Develop.*, 48:3–11 (1994).

Border et al., "Suppression of Experimental Glomerulonephritis by Antiserum Against Transforming Growth Factor β1," *Nature*, 346:371–374 (1990).

Dudley et al., "A requirement for bone morphogenetic protein–7 during development of the mammalian kidney and eye," *Genes & Devel.* 9:2795–2807 (1995).

Guler et al., "Effects of Recombinant Insulin–Like Growth Factor I on Insulin Secretion and Renal Function in Normal Human Subjects," *Proc. Natl. Acad. Sci. (USA)*, 86:2868–2872 (1989).

Hamaguchi et al., "Transforming Growth Factor–β1 Expression and Phenotypic Modulation in the Kidney of Hypertensive Rats," *Hypertension*, 26(1):199–207 (1995).

Hirschberg et al., "Effects of Insulin–Like Growth Factor I on Renal Function in Normal Men," *Kidney Intl.* 43:387–397 (1993).

Jones et al., "Involvement of Bone Morphogenetic Protein–4 (BMP–4) and Vgr–1 in Morphogenesis and Neurogenesis in the Mouse," *Development 111*, pp. 531–542 (1991).

Kopple, "Mineral and Electrolyte Metabolism, Nutrition and Metabolism in Renal Disease," *Miner. Electrolyte Metab.*, 18:269–275 (1992).

Lemann et al., "Use of the Serum Creatinine to Estimate Glomerular Filtration Rate in Health and Early Diabetic Nephropathy," *Am. J. Kidney Dis.*, 3:236–243 (1990).

Luo et al., "BMP–7 is an inducer of nephrogenesis, and is also required for eye development and skeletal patterning," *Genes & Devel.*, 9:2808–2820 (1995).

Miller et al., "Effects of IGF–I on renal function in end–stage chronic renal failure," *Kidney Intl.*, 46:201–207 (1994).

Özkaynak et al., "Murine Osteogenic Protein (OP–1): High Levels of mRNA in Kidney," *Biochem. Biophys. Res. Comm.*, 179(1):116–123 (1991).

Özkaynak et al., "Osteogenic Protein–2: A New Member of the Transforming Growth Factor–β Superfamily Expressed Early in Embryogenesis," *J. Biol. Chem.*, 267(35):25220–25227 (1992).

Samaan and Freeman, "Growth Hormone Levels in Severe Renal Failure," *Metabolism*, 19(2):102–113 (1970).

(List continued on next page.)

Primary Examiner—Bennett Celsa
(74) *Attorney, Agent, or Firm*—Ropes & Gray; Matthew P. Vincent; Spencer Schneider

(57) ABSTRACT

The present invention provides methods for the treatment, and pharmaceuticals for use in the treatment, of mammalian subjects at risk chronic renal failure, or at risk of a need for renal replacement therapy. The methods involve the administration of certain morphogens, inducers of those morphogens, or agonists of the corresponding morphogen receptors, or implantation of renal cells induced with those morphogens. The morphogens useful in the invention include osteogenic protein-1 (OP-1) and other members of the OP-1 subfamily of the TGF-β superfamily of growth factors.

24 Claims, 18 Drawing Sheets

OTHER PUBLICATIONS

Shankland et al., "Expression of Transforming Growth Factor-β1 During Diabetic Renal Hypertrophy," *Kidney Intl.*, 46:433–442 (1994).

Tamaki et al., "TGF-β1 in Glomerulosclerosis and Interstitial Fibrosis of Adriamycin Nephropathy," *Kidney Intl.*, 45:525–536 (1994).

Toback, "Regeneration after acute tubular necrosis," *Kidney Intl.*, 41:226–246 (1992).

Vukicevic et al., "Developing Human Lung and Kidney are Major Sites for Synthesis of Bone Morphogenetic Protein–3 (Osteogenin)," *J. Histochem. Cytochem.*, 42(7):869–875 (1994).

Vukicevic et al., "Localization of Osteogenic Protein–1 (Bone Morphogenetic Protein–7) During Human Embryonic Development: High Affinity Binding to Basement Membrances," *Biochem. Biophys. Res. Comm.*, 198(2):693–700 (1994).

Wright et al., "Serum–Growth Hormone and Glucose Intolerance in Renal Failure," *The Lancet*, pp. 798–800 (1968).

Yamamoto et al., "Expression of Transforming Growth Factor β is Elevated in Human and Experimental Diabetic Nephropathy," *Proc. Natl. Acad. Sci. (USA)*, 90:1814–1818 (1993).

Yamamoto et al., "Sustained Expression of TGF-β1 Underlies Development of Progressive Kidney Fibrosis," *Kidney International*, 45:916–927 (1994).

\* cited by examiner

|        | Cys | Lys | Lys | His | Glu | Leu | Tyr | Val |
|--------|-----|-----|-----|-----|-----|-----|-----|-----|
| hOP-1  | .   | .   | .   | .   | .   | .   | .   | .   |
| mOP-1  | .   | .   | .   | .   | .   | .   | .   | .   |
| hOP-2  | .   | Arg | Arg | .   | .   | .   | .   | .   |
| mOP-2  | .   | Arg | Arg | .   | .   | .   | .   | .   |
| mOP-3  | .   | Arg | Arg | .   | .   | .   | .   | .   |
| DPP    | .   | Arg | Arg | .   | Ser | .   | .   | .   |
| Vg1    | .   | .   | Lys | Arg | His | .   | .   | .   |
| Vgr-1  | .   | .   | .   | .   | Gly | .   | .   | .   |
| CBMP-2A| .   | Arg | Arg | .   | Pro | .   | .   | .   |
| CBMP-2B| .   | Arg | Arg | .   | Ser | .   | .   | .   |
| BMP3   | .   | Ala | Arg | Arg | Tyr | .   | Lys | .   |
| GDF-1  | .   | Arg | Ala | Arg | Arg | .   | .   | .   |
| 60A    | .   | Gln | Met | Glu | Thr | .   | .   | .   |
| BMP5   | .   | .   | .   | .   | .   | .   | .   | .   |
| BMP6   | .   | Arg | .   | .   | 5   | .   | .   | .   |

Fig. 7-1

| | Ser | Phe | Arg | Asp | Leu | Gly | Trp | Gln | Asp |
|---|---|---|---|---|---|---|---|---|---|
| hOP-1 | Ser | Phe | Arg | Asp | Leu | Gly | Trp | Gln | Asp |
| mop-1 | . | . | . | . | . | . | . | . | . |
| hOP-2 | . | . | Gln | . | . | . | . | Leu | . |
| mOP-2 | Ser | . | . | . | . | . | . | Leu | . |
| mOP-3 | . | . | . | . | . | . | . | Leu | . |
| DPP | Asp | . | Ser | . | Val | . | . | Asp | . |
| Vg1 | Glu | . | Lys | . | Val | . | . | . | Asn |
| Vgr-I | . | . | Gln | . | Val | . | . | . | . |
| CBMP-2A | Asp | . | Ser | . | Val | . | . | Asn | . |
| CBMP-2B | Asp | . | Ser | . | Val | . | . | Asn | . |
| BMP3 | Asp | . | Ala | Glu | Ile | . | . | Ser | Glu |
| GDF-1 | . | . | . | . | Val | . | . | His | Arg |
| 60A | Asp | . | Lys | . | . | . | . | His | . |
| BMP5 | . | . | . | . | . | . | . | . | . |
| BMP6 | . | . | Gln | . | . | . | . | . | . |

Fig. 7-2

| | Trp | Ile | Ile | Ala | Pro | Glu | Gly | Tyr | Ala |
|---|---|---|---|---|---|---|---|---|---|
| hOP-1 | Trp | Ile | Ile | Ala | Pro | Glu | Gly | Tyr | Ala |
| mop-1 | . | . | . | . | . | . | . | . | . |
| hOP-2 | . | Val | . | . | . | Gln | . | . | Ser |
| mOP-2 | . | Val | Val | . | . | Gln | . | . | Ser |
| mOP-3 | Ser | Val | Val | . | . | Gln | . | . | Ser |
| DPP | . | . | Val | . | . | Leu | . | . | Asp |
| Vgl | . | Val | . | . | . | Gln | . | . | Met |
| Vgr-1 | . | . | . | . | . | Lys | . | . | . |
| CBMP-2A | . | . | Val | . | . | Pro | . | . | His |
| CBMP-2B | . | . | Val | . | . | Pro | . | . | Gln |
| BMP3 | . | . | . | Ser | . | Lys | Ser | Phe | Asp |
| GDF-1 | . | Val | . | . | . | Arg | . | Phe | Leu |
| 60A | . | . | . | . | . | . | . | . | Gly |
| BMP5 | . | . | . | . | . | . | . | . | . |
| BMP6 | . | . | 20 | . | . | Lys | . | 25 | . |

Fig. 7-3

|        | Ala | Tyr | Tyr | Cys | Glu | Gly | Glu | Cys | Ala |
|--------|-----|-----|-----|-----|-----|-----|-----|-----|-----|
| hOP-1  | Ala | Tyr | Tyr | Cys | Glu | Gly | Glu | Cys | Ala |
| mOP-1  | .   | .   | .   | .   | .   | .   | .   | .   | .   |
| hOP-2  | .   | .   | .   | .   | .   | .   | .   | .   | Ser |
| mOP-2  | .   | .   | .   | .   | .   | .   | .   | .   | .   |
| mOP-3  | .   | .   | .   | .   | Ala | .   | .   | .   | Ile |
| DPP    | .   | .   | Asn | .   | His | .   | Lys | .   | Pro |
| Vg1    | .   | .   | Asn | .   | Tyr | .   | .   | .   | Pro |
| Vgr-1  | .   | .   | Phe | .   | Asp | .   | .   | .   | Ser |
| CBMP-2A| .   | .   | Phe | .   | His | .   | Glu | .   | Pro |
| CBMP-2B| .   | .   | Phe | .   | His | .   | Asp | .   | Pro |
| BMP3   | .   | .   | .   | .   | Ser | .   | Ala | .   | Gln |
| GDF-1  | .   | .   | Asn | .   | Gln | .   | Gln | .   | .   |
| 60A    | .   | .   | Phe | .   | Ser | .   | .   | .   | Asn |
| BMP5   | .   | .   | Phe | .   | Asp | .   | .   | .   | Ser |
| BMP6   | .   | .   | Asn | .   | Asp | .   | .   | .   | Ser |
|        |     |     |     | 30  |     |     |     |     | 35  |

Fig. 7-4

|  | Phe | Pro | Leu | Asn | Ser | Tyr | Met | Asn | Ala |
|---|---|---|---|---|---|---|---|---|---|
| hOP-1 | Phe | Pro | Leu | Asn | Ser | Tyr | Met | Asn | Ala |
| mop-1 | . | . | . | . | . | . | . | . | . |
| hOP-2 | . | . | . | Asp | . | Cys | . | . | . |
| mOP-2 | . | . | . | Asp | . | Cys | . | . | . |
| mOP-3 | Tyr | . | . | . | . | Cys | Phe | . | Ser |
| DPP | . | . | . | Ala | Asp | His | Phe | . | Ser |
| Vgl | Tyr | . | . | Thr | Glu | Ile | Leu | . | Gly |
| Vgr-1 | . | . | . | . | Ala | His | . | . | . |
| CDMP-2A | . | . | . | Ala | Asp | His | Leu | . | Ser |
| CBMP-2B | . | . | . | Ala | Asp | His | Leu | . | Ser |
| GDF-1 | Leu | . | Val | Ala | Leu | Ser | Gly | Ser** | . |
| BMP3 | . | . | Met | Pro | Lys | Ser | Leu | Lys | Pro |
| 60A | . | . | . | . | Ala | His | . | . | . |
| BMP5 | . | . | . | . | Ala | His | Met | . | . |
| BMP6 | . | . | . | . | Ala | His | Met | . | . |

| | Thr | Asn | His | Ala | Ile | Val | Gln | Thr | Leu |
|---|---|---|---|---|---|---|---|---|---|
| hOP-1 | . | . | . | . | . | . | . | . | . |
| mop-1 | . | . | . | . | . | . | . | . | . |
| hOP-2 | . | . | . | . | . | Leu | . | Ser | . |
| mOP-2 | . | . | . | . | . | Leu | . | Ser | . |
| mOP-3 | . | . | . | . | Thr | Met | . | Ala | . |
| DPP | . | . | . | . | Val | . | . | . | . |
| Vgl | Ser | . | . | . | . | Leu | . | . | . |
| Vgr-1 | . | . | . | . | . | . | . | . | . |
| CBMP-2A | . | . | . | . | . | . | . | . | . |
| CBMP-2B | . | . | . | . | . | . | . | . | . |
| BMP3 | Ser | . | . | . | Thr | Ile | . | Ser | Ile |
| GDF-1 | Leu | . | . | . | Val | Leu | Arg | Ala | . |
| 60A | . | . | . | . | . | . | . | . | . |
| BMP5 | . | . | . | . | . | . | . | . | . |
| BMP6 | . | . | . | . | . | 50 | . | . | . |
| | 45 | | | | | | | | |

| | | | | | | | | | | |
|---|---|---|---|---|---|---|---|---|---|---|
| hOP-1 | Val | Val | His | Phe | Ile | Asn | Pro | Glu | Thr | Val |
| mop-1 | . | . | . | . | . | . | . | . | . | . |
| hOP-2 | . | . | His | Leu | . | Lys | . | Asp | Ala | . |
| mOP-2 | . | . | His | Leu | Met | Lys | . | Asn | Val | . |
| mOP-3 | . | . | . | Leu | Met | Lys | . | Asp | Ile | Ile |
| DPP | . | . | Asn | Asn | Asn | . | . | Asp | Lys | . |
| Vg1 | . | . | . | Ser | . | Glu | . | Gly | Asp | Ile |
| Vgr-1 | . | . | . | Val | Met | . | . | . | Tyr | . |
| CBMP-2A | . | . | Asn | Ser | Val | . | Ser | . | Lys | Ile |
| CBMP-2B | . | . | Asn | Ser | Val | . | Ser | . | Ser | Ile |
| BMP3 | . | Arg | Ala** | Gly | Val | Val | Pro | . | Gly | Ile |
| GDF-1 | Met | . | . | Ala | Ala | Ala | . | Pro | Ala | Ala |
| 60A | . | . | Leu | Leu | Leu | Glu | . | Gly | Lys | . |
| BMP5 | . | . | Leu | Leu | Met | Phe | . | Asp | His | . |
| BMP6 | . | . | Leu | Leu | Met | . | . | . | Tyr | . |
| | | 55 | | | | | 60 | | | |

|         | Pro | Lys | Pro | Cys | Cys | Ala | Pro | Thr | Gln |
|---------|-----|-----|-----|-----|-----|-----|-----|-----|-----|
| hOP-1   | Pro | Lys | Pro | Cys | Cys | Ala | Pro | Thr | Gln |
| mop-1   | .   | .   | .   | .   | .   | .   | .   | .   | .   |
| hOP-2   | .   | .   | Ala | .   | .   | .   | .   | .   | Lys |
| mOP-2   | .   | .   | Ala | .   | .   | .   | .   | .   | Lys |
| mOP-3   | .   | .   | Val | .   | .   | Val | .   | .   | Glu |
| DPP     | .   | .   | Ala | .   | .   | Val | .   | .   | .   |
| vg1     | .   | Leu | .   | .   | .   | Val | .   | .   | Lys |
| Vgr-1   | .   | .   | .   | .   | .   | .   | .   | .   | Lys |
| CBMP-2A | .   | .   | Ala | .   | .   | Val | .   | .   | Glu |
| CBMP-2B | .   | .   | Ala | .   | .   | Val | .   | .   | Glu |
| BMP3    | .   | Glu | .   | .   | .   | Val | .   | Glu | Lys |
| GDF-1   | Asp | Leu | .   | .   | .   | Val | .   | Ala | Arg |
| 60A     | .   | .   | .   | .   | .   | .   | .   | .   | Arg |
| BMP5    | .   | .   | .   | .   | .   | .   | .   | .   | Lys |
| BMP6    | .   | .   | .   | .   | .   | .   | .   | .   | Lys |
|         |     |     | 65  |     |     |     |     | 70  |     |

Fig. 7-8

| | | | | | | | | |
|---|---|---|---|---|---|---|---|---|
| hOP-1 | Leu | Asn | Ala | Ile | Ser | Val | Leu | Tyr | PHe |
| mop-1 | . | . | . | . | . | . | . | . | . |
| hOP-2 | . | Ser | . | Thr | . | . | . | . | Tyr |
| mOP-2 | . | Ser | . | Thr | . | . | . | . | Tyr |
| mOP-3 | . | Ser | . | . | . | . | . | . | Tyr |
| Vgl | Met | Ser | Pro | . | . | Leu | . | Phe | Tyr |
| Vgr-1 | Val | . | . | . | . | . | . | . | . |
| DPP | . | Asp | Ser | Val | Ala | Met | . | . | Leu |
| CBMP-2A | . | Ser | . | . | . | Met | . | . | Leu |
| CBMP-2B | . | Ser | . | . | . | Met | . | . | Leu |
| BMP3 | Met | Ser | Ser | Leu | . | Ile | . | . | Tyr |
| GDF-1 | . | Ser | Pro | Leu | Pro | . | . | Phe | . |
| 60A | . | Gly | . | Leu | . | . | . | . | His |
| BMP5 | . | . | . | . | . | . | . | . | . |
| BMP6 | . | . | . | . | . | . | . | . | . |
| | | | 75 | | | | | 80 | |

Fig. 7-9

| | Asp | Asp | Ser | Ser | Asn | Val | Ile | Leu | Lys |
|---|---|---|---|---|---|---|---|---|---|
| hOP-1 | Asp | Asp | Ser | Ser | Asn | Val | Ile | Leu | Lys |
| mop-1 | : | : | : | : | : | : | : | : | : |
| hOP-2 | : | Ser | : | Asn | Asn | : | : | : | Arg |
| mOP-2 | : | Ser | : | Asn | Asn | : | : | : | Arg |
| mOP-3 | : | Arg | Asn | Asn | Asn | : | : | : | Arg |
| DPP | Asn | : | Gln | : | Thr | : | Val | : | : |
| Vg1 | : | Asn | Asn | Asp | : | : | Val | : | Arg |
| Vgr-1 | : | : | Asn | : | : | : | : | : | : |
| CBMP-2A | : | Glu | Asn | Glu | Lys | : | Val | : | : |
| CBMP-2B | : | Glu | Tyr | Asp | Lys | : | Val | : | : |
| BMP3 | : | Glu | Asn | Lys | Asp | : | Val | : | : |
| GDF-1 | : | Asn | : | Asp | : | : | Val | : | : |
| 60A | Leu | Asn | Asp | Glu | : | : | Asn | : | : |
| BMP5 | : | : | : | : | : | : | : | : | : |
| BMP6 | : | : | Asn | : | : | : | : | : | : |

| | Lys | Tyr | Arg | Asn | Met | Val | Val | Val | Arg |
|---|---|---|---|---|---|---|---|---|---|
| hOP-1 | | | | | | | | | |
| mop-I | | His | | | | | | | Lys |
| hOP-2 | | His | | | | | | | Lys |
| mOP-2 | Arg | Glu | | | | | | | Gln |
| mOP-3 | Asn | | | | | Thr | | | Val |
| DPP | His | | Gln | Glu | | Ala | | | Asp |
| vgl | | | Glu | | | | | | |
| Vgr-1 | | | | | | | | | |
| CBMP-2A | Asn | | Gln | Asp | | | | | Glu |
| CBMP-2B | Asn | | Gln | Glu | | | | | Glu |
| BMP3 | Val | | Pro | | | Thr | | | Glu |
| GDF-1 | Gln | | Glu | Asp | | | | | Asp |
| 60A | | | | | | Ile | | | Lys |
| BMP5 | | | | TrP | | | | | |
| BMP6 | 90 | | | | | 95 | | | |

Fig. 7-11

|  | Ala | Cys | Gly | Cys | His |
|---|---|---|---|---|---|
| hOP-1 | Ala | Cys | Gly | Cys | His |
| mop-1 | . | . | . | . | . |
| hOP-2 | . | . | . | . | . |
| mOP-2 | . | . | . | . | . |
| mOP-3 | . | . | . | . | . |
| DPP | Gly | . | . | . | Arg |
| Vgl | Glu | . | . | . | Arg |
| Vgr-1 | . | . | . | . | . |
| CBMP-2A | Gly | . | . | . | Arg |
| CBMP-2B | Gly | . | . | . | Arg |
| BMP3 | Ser | . | Ala | . | Arg |
| GDF-1 | Glu | . | . | . | Arg |
| 60A | Ser | . | . | . | . |
| BMP6 | . | . | . | . | . |
|  |  |  | 100 |  |  |

Fig. 7-12

**Between residues 56 and 57 of BMP3 is a Val residue; between residues 43 and 44 of GDF-1 lies the amino acid sequence Gly-Gly-Pro-Pro.

MORPHOGEN TREATMENT FOR CHRONIC RENAL FAILURE

FIELD OF THE INVENTION

The present invention relates generally to methods of treatment for renal disease. In particular, the invention relates to methods of treatment for conditions which place mammals, including humans, at risk of chronic renal failure. The methods involve the administration of certain morphogens, inducers of those morphogens, or agonists of the corresponding morphogen receptors, or implantation of renal cells induced with those morphogens.

BACKGROUND OF THE INVENTION

The mammalian renal system serves primary roles both in the removal of catabolic waste products from the bloodstream and in the maintenance of fluid and electrolyte balances in the body. Renal failures are, therefore, life-threatening conditions in which the build-up of catabolites and other toxins, and/or the development of significant imbalances in electrolytes or fluids, may lead to the failure of other major organs systems and death. As a general matter, renal failure is classified as "acute" or "chronic." As detailed below, the differences between these two conditions are not merely a matter of severity or rapidity but, rather, reflect differences in etiology, prognosis, and treatment.

Acute Renal Failure

Acute renal failure is defined as an abrupt cessation or substantial reduction of renal function and, in as many as 90–95% of cases, may be secondary to trauma, surgery or another acute medical condition. Acute renal failure may be due to pre-renal causes (e.g., decreased cardiac output, hypovolemia, altered vascular resistance) or to post-renal causes (e.g., obstructions or constrictions of the ureters, bladder or urethra) which do not directly involve the kidneys and which, if treated quickly, will not entail significant loss of nephrons or other damage to the kidneys. Alternatively, acute renal failure may be due to intrinsic renal causes which involve a more direct insult or injury to the kidneys, and which may entail permanent damage to the nephrons or other kidney structures. Intrinsic causes of acute renal failure include but are not limited to infectious diseases (e.g., various bacterial, viral or parasitic infections), inflammatory diseases (e.g., glomerulonephritis, systemic lupus erythematosus), ischemia (e.g., renal artery occlusion), toxic syndromes (e.g., heavy metal poisoning, side-effects of antimicrobial treatments or chemotherapy), and direct traumas.

The diagnosis and treatment of acute renal failure is as varied as its causes. In human patients, oliguria (urine output<400 ml/day) or anuria (urine output<50 ml/day) may be present in 50–70% of cases, BUN levels may climb 10–20 mg/dl/day or faster, plasma creatinine levels may climb 0.5–1.0 mg/dl/day, and metabolic acidosis is almost always present. If not treated, the electrolyte and fluid imbalances (e.g., hyperkalemia, acidosis edema) associated with acute renal failure may lead to life-threatening arrhythmia, congestive heart failure, or multiple organ system failures. Present therapies are typically directed at the underlying causes of the acute renal failure (e.g., pre-renal, post-renal, or infectious causes) and management of the complications. Due to the severity of acute renal failure, episodes rarely last longer than several weeks without mortality and are treated on an in-patient basis.

Chronic Renal Failure

Chronic renal failure may be defined as a progressive, permanent and significant reduction of the glomerular filtration rate (GFR) due to a significant and continuing loss of nephrons. Chronic renal failure typically begins from a point at which a chronic renal insufficiency (i.e., a permanent decrease in renal function of at least 50–60%) has resulted from some insult to the renal tissues which has caused a significant loss of nephron units. The initial insult may or may not have been associated with an episode of acute renal failure. Irrespective of the nature of the initial insult, chronic renal failure manifests a "final common path" of signs and symptoms as nephrons are progressively lost and GFR progressively declines. This progressive deterioration in renal ftmction is slow, typically spanning many years or decades in human patients, but seemingly inevitable.

The early stage of chronic renal failure typically begins when GFR has been reduced to approximately one-third of normal (e.g., 30–40 ml/min for an average human adult). As a result of the significant nephron loss, and in an apparent "attempt" to maintain the overall GFR with fewer nephrons, the average single nephron GFR (SNGFR) is increased by adaptations of the remaining nephrons at both the structural and functional level. One structural manifestation of this adaptation, readily detectable by microscopic examination of biopsy samples, is a "compensatory hypertrophy" of both the glomeruli and the tubules of the kidney, a process which literally increases the volume of filtrate which can be produced by each remaining nephron by literal enlargement of the glomeruli and tubules. Indeed, as a result of the hypertrophy or dilation of the collecting ducts, the urine of subjects with chronic renal failure often contains broad "casts," typically 2–6 times normal diameter, which aid in diagnosis and have also been referred to as "renal failure casts." At the same time, there are functional changes in the remaining nephrons, such as decreased absorption or increased secretion of normally excreted solutes, which may be responses to hormonal or paracrine changes elsewhere in the body (e.g., increasing levels of parathyroid hormone (PTH) in response to changes in serum levels of calcium and phosphate).

These adaptations in early stage chronic renal failure are not successful in completely restoring GFR or other parameters of renal function and, in fact, subject the remaining nephrons to increased risk of loss. For example, the increased SNGFR is associated with mechanical stresses on the glomerulus due to hypertension and hyperperfusion. The loss of integrity of podocyte junctures leads to increased permeability of the glomerulus to macromolecules or "leakiness" of the glomerular capsule. Proliferative effects are also observed in mesangial, epithelial and endothelial cells, as well as increases in the deposition of collagen and other matrix proteins. Sclerosis of both the glomeruli and tubules is another common symptom of the hypertrophied nephrons and the risk of coagulation in the glomerulus is increased. In particular, these adaptations of the remaining nephrons, by pushing the SNGFR well beyond its normal level, actually decrease the capacity of the remaining nephrons to respond to acute changes in water, solute, or acid loads and, therefore, actually increase the probability of additional nephron loss.

As chronic renal failure progresses, and GFR continues to decline to less than 10% of normal (e.g., 5–10 ml/min), the subject enters end-stage renal disease (ESRD). During this phase, the inability of the remaining nephrons to adequately remove waste products from the blood, while retaining useful products and maintaining fluid and electrolyte balance, leads to a rapid decline in which many organ systems, and particularly the cardiovascular system, may begin to fail. For example, BUN and creatinine levels may be expected to rise and, at BUN levels of 60–100 mg/dl and serum creatinine levels of 8–12 mg/dl, a uremic syndrome will typically develop in which the kidneys can no longer remove the end products of nitrogen metabolism. At this point, renal failure will rapidly progress to death unless the subject receives renal replacement therapy (i.e., chronic hemodialysis, continuous peritoneal dialysis, or kidney transplantation).

Approximately 600 patients per million receive chronic dialysis each year in the United States, at an average cost approaching $60,000–$80,000 per patient per year. Of the new cases of end-stage renal disease each year, approximately 28–33% are due to diabetic nephropathy (or diabetic glomerulopathy or diabetic renal hypertrophy), 24–29% are due to hypertensive nephrosclerosis (or hypertensive glomerulosclerosis), and 15–22% are due to glomerulonephritis. The 5-year survival rate for all chronic dialysis patients is approximately 40%, but for patients over 65, the rate drops to approximately 20%.

Morphogens and Growth Factors

A great many proteins have now been identified which appear to act as morphogenetic or growth factors, regulating cell proliferation or differentiation. Typically these growth factors exert their effects on specific sets or subsets of cells or tissues. Thus, for example, epidermal growth factors, nerve growth factors, fibroblast growth factors, various hormones, and many other proteins inducing or inhibiting cell proliferation or differentiation have been identified and shown to affect some subgroup of cells or tissues.

One group of morphogenetic proteins, referred to herein as "morphogens," includes members of the family of bone morphogenetic proteins (BMPs) which were initially identified by their ability to induce ectopic, endochondral bone morphogenesis. Subsequent characterization of the nucleic acid and amino acid sequences of the BMPs has shown them to be a subgroup of the TGF-β superfamily of growth factors. Members of the morphogen family have now been shown to include the mammalian osteogenic protein-1 (OP-1, also known as BMP-7), osteogenic protein-2 (OP-2), osteogenic protein-3 (OP-3). BMP-2 (also known as BMP-2A or CBMP-2A), BMP-3, BMP-4 (also known as BMP-2B or CBMP-2B), BMP-5, BMP-6, Vgr-1, and GDF-1, as well as the Xenopus homologue Vgl and the Drosophila homologues DPP and 60A. Members of this family encode secreted polypeptides that share common structural features and that are similarly processed from a pro-protein to yield a carboxy terminal mature protein of approximately 110 amino acids. All members share a conserved pattern of cysteines in this domain and the active form of these proteins is either a disulfide-bonded homodimer of a single family member, or a heterodimer of two different members (see, e.g., Massague (1990) *Annu. Rev. Cell Biol.* 6:597; Sampath, et al. (1990) *J. Biol. Chem.* 265:13198).

The members of the morphogen family of proteins are expressed in a variety of tissues during development. BMP-3 for, example, has been shown to be expressed in developing human lung and kidney (Vukicevic et al. (1994) *J. Histochem. Cytochem.* 42:869–875), BMP-4 has been shown to be expressed in the developing limbs, heart, facial processes and condensed mesenchyme associated with early whisker follicles in embryonic mice (Jones, et al. (1991) *Development* 111:531–542), and OP-1 (BMP-7) has been shown immunohistochemically to be associated with basement membranes in human embryos, including those of the developing lungs, pancreas, skin, and convoluted tubules of kidneys (Vukicevic, et al. (1994) *Biochem. Biophys. Res. Commun.* 198:693–700). Some of the morphogens (e.g., OP-2 and BMP-2) were not detected in analyses of adult tissues, suggesting only an early developmental role for these morphogens (Ozkaynak, et al. (1992) *J. Biol. Chem.* 267:25220–25227). In contrast, high levels of murine OP-1 expression have been observed in adult mouse kidneys (Ozkaynak, et al. (1991) *Biochem. Biophys. Res. Commun.* 179:116–123). This suggests a possible role for OP-1 synthesized in the kidney as a paracrine regulator of bone growth, and would be consistent with the role of the kidneys in both calcium regulation and bone homeostasis.

A great variety of growth factors have been considered which may participate in the regulation of the growth and repair of renal tissues (reviewed in, e.g., Toback (1992) *Kidney Intl.* 41:226–246). For example, EGF, TGF-α, TGF-β, IGF-I, IGF-II, PDGF, FGF, Renin/Angiotensin II, IL-I and OP-I have all been found to be expressed by various adult renal cells or tissues and to have effects on renal cell proliferation or differentiation (see, Toback (1992) supra, Ozkaynak, et al. (1991) a). In addition, several of these have been found to be expressed in the developing kidney, including IGF-I, TGF-β and OP-1 (reviewed in, e.g., Bard, et al. (1994) *Mech. Develop.* 48:3–11).

Interestingly, TGF-β has been shown in a murine metanephric organ culture system to retard overall growth and segmental differentiation of all segments of developing nephrons except the thick ascending limb-early distal tubules (Avner and Sweeney (1990) *Pediatr. Nephrol.* 4:372–377). In addition, TGF-β expression has been found to be increased in several models of renal disease, suggesting that TGF-β mediated increases in the synthesis of extracellular matrix components may be involved in the etiology of diabetic nephropathy (or diabetic glomerulopathy or diabetic renal hypertrophy), renal fibrosis, glomerulosclerosis and glomerulonephritis, interstitial fibrosis. and hypertensive nephrosclerosis (Shankland, et al. (1994) *Kidney Intl.* 46:430–442; Yamamoto, et al. (1994) *Kidney Intl.* 45:916–927; Yamamoto, et al. (1993) *PNAS* 90:1814–1818; Tamaki, et al. (1994) *Kidney Intl.* 45:525–536; Border, et al. (1990) *Nature* 346:371–374; Hamaguchi, et al. (1995) *Hypertension* 26:199–207).

Also of interest is the fact that serum levels of human growth hormone (GH) are elevated in subjects with chronic renal failure (Wright et al. (1968) *Lancet* 2:798; Samaan and Freeman (1970) *Metabolism* 19:102). Recombinant GH has been shown to help maintain protein balance in malnourished chronic renal failure patients, and to promote "catch-up" growth in children with chronic renal failure. It has been suggested that these effects are mediated by IGF-I (see, e.g., Kopple (1992) *Miner. Electrolyte Metab.* 18:269–275). Although some studies have found that the administration of IGF-I increases renal plasma flow and GFR in chronic renal failure patients (e.g., Guler, et al. (1989) *PNAS* 86:2868–2872; Hirschberg, et al. (1993) *Kidney Intl.* 43:387–397), other studies have found that this effect is merely transient (Miller, et al. (1994) *Kidney Intl.* 46:201–207).

Thus, although some growth factors have been shown to be expressed in both developing and adult renal tissues, and although at least one has been shown to increase renal function in the short term, none has yet been shown to be of therapeutic benefit in preventing, inhibiting, or delaying the progressive loss of renal function that characterizes chronic renal failure. A need remains, therefore, for treatments which will prevent the progressive loss of renal function which has caused almost two hundred thousand patients in the United States alone to become dependent upon chronic dialysis, and which results in the premature deaths of tens of thousands each year.

SUMMARY OF THE INVENTION

The present invention is directed to methods of treatment, and pharmaceutical preparations for use in the treatment, of mammalian subjects at risk of chronic renal failure, or at risk of the need for renal replacement therapy. Such subjects include subjects already afflicted with chronic renal failure, or which have already received renal replacement therapy, as well as any subject reasonably expected to suffer a progressive loss of renal function associated with progressive loss of functioning nephron units. Whether a particular subject is at riskis a determination which may routinely be made by one of ordinary skill in the relevant medical or veterinary art. Subjects at risk of chronic renal failure, or at risk of the need for renal replacement therapy, include but are not limited to the following: subjects which may be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min, 30 ml/min or 20 ml/min; human female subjects weighing at least about 40 kg and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

The methods and compositions of this invention capitalize in part upon the discovery that certain proteins of eukaryotic origin, defined herein as morphogens, may be used in the treatment of subjects at risk, as defined herein, of chronic renal failure or the need for renal replacement therapy. Generally, the morphogens of the invention are dimeric proteins that induce morphogenesis of one or more eukaryotic (e.g., mammalian) cells, tissues or organs. Of particular interest herein are morphogens that induce morphogenesis at least of mammalian renal tissue, including formation of functional renal epithelium and, in particular, functional glomerular and tubular epithelium. Morphogens comprise a pair of polypeptides that, when folded, adopt a configuration sufficient for the resulting dimeric protein to elicit morphogenetic responses in cells and tissues displaying receptors specific for said morphogen. That is, morphogens generally induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. "Progenitor" cells are uncommitted cells that are competent to differentiate into one or more specific types of differentiated cells, depending on their genomic repertoire and the tissue specificity of the permissive environment in which morphogenesis is induced. Morphogens further can delay or mitigate the onset of senescence- or quiescence-associated loss of phenotype and/or tissue function. Morphogens still further can stimulate phenotypic expression of differentiated cells, including expression of metabolic and/or functional, e.g., secretory, properties thereof. In addition, morphogens can induce redifferentiation of committed cells under appropriate environmental conditions. As noted above, morphogens that induce proliferation and/or differentiation at least of mammalian renal tissue, and/or support the growth, maintenance and/or functional properties of mammalian nephrons, are of particular interest herein.

In preferred embodiments, the pair of morphogen polypeptides have amino acid sequences each comprising a sequence that shares a defined relationship with an amino acid sequence of a reference morphogen. Herein, preferred morphogen polypeptides share a defined relationship with a sequence present in morphogenically active human OP-1, SEQ ID NO: 4. However, any one or more of the naturally occurring or biosynthetic sequences disclosed herein similarly could be used as a reference sequence. Preferred morphogen polypeptides share a defined relationship with at least the C-terminal six cysteine domain of human OP-1, residues 43–139 of SEQ ID NO: 4. Preferably, morphogen polypeptides share a defined relationship with at least the C-terminal seven cysteine domain of human OP-1, residues 38–39 of SEQ ID NO: 4. That is, preferred morphogen polypeptides in a dimeric protein with morphogenic activity each comprise a sequence that corresponds to a reference sequence or is functionally equivalent thereto.

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. Functionally equivalent sequences further include those wherein one or more amino acid residues differs from the corresponding residue of a reference morphogen sequence, e.g., the C-terminal seven cysteine domain (also referred to herein as the conserved seven cysteine skeleton) of human OP-1, provided that this difference does not destroy morphogenic activity. Accordingly, conservative substitutions of corresponding amino acids in the reference sequence are preferred. Amino acid residues that are "conservative substitutions" for corresponding residues in a reference sequence are those that are physically or functionally similar to the corresponding reference residues, e.g., that have similar size, shape, electric charge, chemical properties including the ability to form covalent or hydrogen bonds, or the like. Particularly preferred conservative substitutions are those fulfilling the criteria defined for an "accepted point mutation" in Dayhoff et al. (1978), 5 *Atlas of Protein Sequence and Structure*, Suppl. 3, ch. 22 (pp. 354–352), Natl. Biomed. Res. Found., Washington, D.C. 20007, the teachings of which are incorporated by reference herein.

In certain embodiments, a polypeptide suspected of being functionally equivalent to a reference morphogen polypeptide is aligned therewith using the method of Needleman, et al. (1970), *J. Mol. Biol.* 48:443–453, implemented conveniently by computer programs such as the Align program (DNAstar, Inc.). As noted above, internal gaps and amino acid insertions in the candidate sequence are ignored for purposes of calculating the defined relationship, conventionally expressed as a level of amino acid sequence homology or identity, between the candidate and reference sequences. "Amino acid sequence homology" is understood herein to mean amino acid sequence similarity. Homologous sequences share identical or similar amino acid residues, where similar residues are conservative substitutions for, or "allowed point mutations" of, corresponding amino acid residues in an aligned reference sequence. Thus, a candidate polypeptide sequence that shares 70% amino acid homology y with a reference sequence is one in which any 70% of the aligned residues are either identical to or are conservative substitutions of the corresponding residues in a reference sequence.

Of particular interest herein are morphogens, which, when provided to the kidney of a mammal, induce or maintain the normal state of differentiation and growth of nephron units. Of still more particular interest herein are morphogens which, when administered to a mammal, prevent, inhibit or delay the development of compensatory hypertrophy, including glomerular hypertrophy and/or tubular hypertrophy. Such morphogens can be used to treat a mammal at risk of chronic renal failure by preventing, inhibiting or delaying the progressive loss of functional nephron units and the consequent progressive loss of renal function.

The present invention alternatively can be practiced with methods and compositions comprising a morphogen stimulating agent or morphogen inducer in lieu of a morphogen. A "morphogen inducer" is a compound that stimulates in vivo production, e.g., expression, of a therapeutically effective concentration of an endogenous morphogen in the body of a mammal sufficient to regenerate or maintain renal tissue and/or to inhibit additional loss thereof. Such compounds are understood to include substances which, when administered to a mammal, act on cells of tissue(s) or organ(s) that normally are competent to produce and/or secrete a morphogen encoded within the genome of the mammal. and which cause the endogenous level of the morphogen in the mammal's body to be altered. Endogenous or administered morphogens can act as endocrine, paracrine or autocrine factors. That is, endogenous morphogens can be synthesized by the cells in which morphogenetic responses are induced, by neighboring cells, or by cells of a distant tissue, in which circumstances the secreted endogenous morphogen is transported to the site of morphogenesis, e.g., by the individual's bloodstream. In preferred embodiments, the agent stimulates expression and/or secretion of an endogenous morphogen so as to increase amounts thereof in renal tissues.

In still other embodiments, an agent which acts as an agonist of a morphogen receptor may be administered instead of the morphogen itself. An "agonist" of a receptor means a compound which binds to the receptor and for which such binding has a similar functional result as binding of the natural, endogenous ligand of the receptor. That is, the compound must, upon interaction with the receptor, produce the same or substantially similar transmembrane and/or intracellular effects as the endogenous ligand. Thus, an agonist of a morphogen receptor binds to the receptor and such binding has the same or a similar functional result as morphogen binding (e.g., induction of morphogenesis). The activity or potency of an agonist can be less than that of the natural ligand, in which case the agonist is said to be a "partial agonist," or it can be equal to or greater than that of the natural ligand, in which case it is said to be a "full agonist." Thus, for example, a small peptide or other molecule which can mimic the activity of a morphogen in binding to and activating the morphogen's receptor may be employed as an equivalent of the morphogen. Preferably the agonist is a full agonist, but partial morphogen receptor agonists may also be advantageously employed. Methods of identifying such agonists are known in the art and include assays for compounds which induce morphogen-mediated responses (e.g., induction of differentiation of metanephric mesenchyme, induction of endochondral bone formation, and the like). Such an agent may also be referred to as a morphogen "mimic," "mimetic," or "analog."

The morphogens, inducers and agonists of the invention may be administered by any route of administration which is compatible with the selected agent, and may be formulated with any pharmaceutically acceptable carrier appropriate to the route of administration. Preferred routes of administration are parenteral and, in particular, intravenous, intraperitoneal, and renal intracapsular. Treatments are also preferably conducted over an extended period on an outpatient basis with daily dosages for morphogens in the range of about 0.01–1000 µg/kg body weight, and more preferably about 0.1–100 µg/kg body weight.

Finally, in yet further embodiments, renal cells may be implanted into the kidney of a subject at risk of chronic renal failure, or at risk of needing renal replacement therapy, in order to serve as a source of morphogen and/or to provide a source of additional functional renal tissue. These cells may be renal mesenchymal progenitor cells, or renal mesenchymal progenitor cells which have been induced to undergo metanephric differentiation. The cells may be derived from a donor (e.g., a tissue-type matched donor, sibling, identical twin), may be derived from a tissue culture (e.g., undifferentiated renal mesenchyme culture, fetal renal tissue culture), or may be explanted from the subject and then be re-implanted after proliferation and/or differentiation. Preferably, the cells are induced to undergo metanephric differentiation by treatment with a morphogen (e.g., OP-1) either before or after implantation.

The treatments of the present invention are useful in preventing, inhibiting or delaying the progressive loss of functional nephron units, and the consequent progressive loss of renal function, which typify chronic renal failure. As such they are of great value in preventing or delaying the need for chronic dialysis or renal replacement therapy in subjects with chronic renal insufficiency, or reducing the necessary frequency of chronic renal dialysis in subjects with end-stage renal disease. As such, they are useful in prolonging the lives, and in maintaining the quality of life, of subjects at risk of, or already afflicted with, chronic renal failure.

BRIEF DESCRIPTION OF THE FIGURES

FIG. 7. Panels 7-1 through 7-12 of this figure are a tabular alignment of the amino acid sequences of various naturally occurring morphogens with a preferred reference sequence of human OP-1, residues 38–139 of SEQ ID NO: 4. Morphogen polypeptides shown in this figure also are identified in the Sequence Listing.

DETAILED DESCRIPTION OF THE INVENTION

I. Definitions

Figure 1:
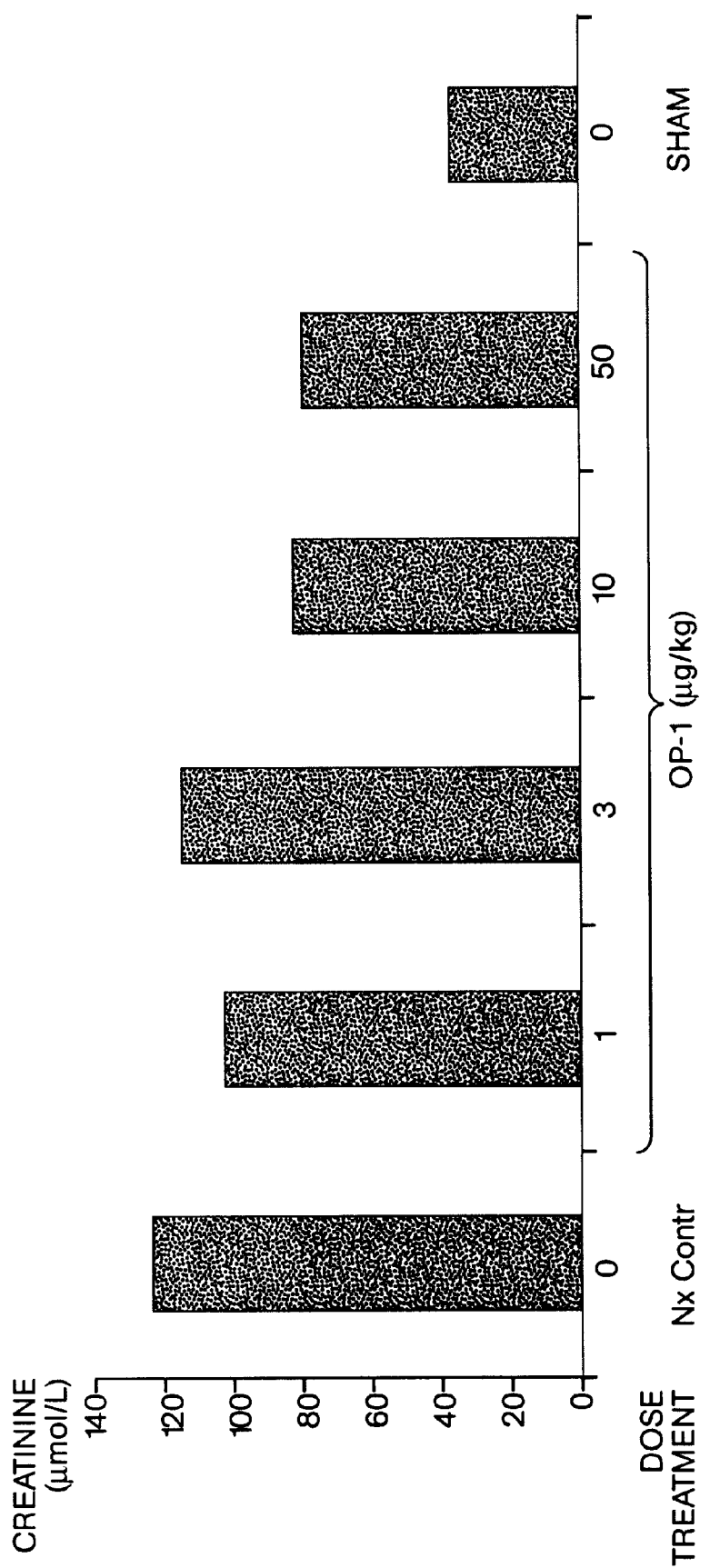
FIG. 1. This figure is a bar graph showing average serum creatinine levels for groups to sham-operated ("SHAM") or partially nephrectomized ("Nx Contr" and "OP-1") rats. 5–6 months post-surgery, rats received injections of vehicle only ("Nx control" and "SHAM") or 1, 3, 10 or 50 µg/kg body weight of soluble OP-1 ("OP-1") three times a week for 4–8 weeks.

In order to more clearly and concisely point out the subject matter of the claimed invention, the following definitions are provided for specific terms used in the following written description and appended claims.

Glomerular Filtration Rate (GFR). The "glomerular filtration rate" or "GFR" is proportional to the rate of clearance into urine of a plasma-borne substance which is not bound by serum proteins, is freely filtered across glomeruli, and is neither secreted nor reabsorbed by the renal tubules. Thus, as used herein, GFR preferably is defined by the following equation:

$$GFR = \frac{U_{conc} \times V}{P_{conc}}$$

where $U_{conc}$ is the urine concentration of the marker, $P_{conc}$ is the plasma concentration of the marker, and V is the urine flow rate in ml/min. Optionally, GFR is corrected for body surface area. Thus, the GFR values used herein may be regarded as being in units of ml/min/1.73 m².

The preferred measure of GFR is the clearance of inulin but, because of the difficulty of measuring the concentrations of this substance, the clearance of creatinine is typically used in clinical settings. For example, for an average size, healthy human male (70 kg, 20–40 yrs), a typical GFR measured by creatinine clearance is expected to be approximately 125 ml/min with plasma concentrations of creatinine of 0.7–1.5 mg/dl. For a comparable, average size woman, a typical GFR measured by creatinine clearance is expected to be approximately 115 ml/min with creatinine levels of 0.5–1.3 mg/dl. During times of good health, human GFR values are relatively stable until about age 40, when GFR typically begins to decrease with age. For subjects surviving to age 85 or 90, GFR may be reduced to 50% of the comparable values at age 40.

The "single nephron GFR" or "SNGFR" is the rate of filtration for a single nephron. With a GFR of 120 ml/min and approximately 1 million nephrons per intact healthy kidney, the single nephron glomerular filtration rate (SNGFR) has been estimated at approximately 60 nl/min in a typical, healthy human adult.

Expected Glomerular Filtration Rate ($GFR_{exp}$). An estimate of the "expected GFR" or "$GFR_{exp}$" may be provided based upon considerations of a subject's age, weight, sex, body surface area, and degree of musculature, and the plasma concentration of some marker compound (e.g., creatinine) as determined by a blood test. Thus, as an example, an expected GFR or $GFR_{exp}$ may be estimated as:

$$GFR_{exp} \approx \frac{(140 - age) \times weight\ (kg)}{72 \times P_{conc}\ (mg/dl)}$$

This estimate does not take into consideration such factors as surface area, degree of musculature, or percentage body fat. Nonetheless, using plasma creatinine levels as the marker, this formula has been employed for human males as an inexpensive means of estimating GFR. Because creatinine is produced by striated muscle, the expected GFR or $GFR_{exp}$ of human female subjects is estimated by the same equation multiplied by 0.85 to account for expected differences in muscle mass. (See Lemann, et al. (1990) *Am. J. Kidney Dis.* 16(3):236–243.)

Broad Cast. Microscopic examination of urinary sediment for the presence formed elements is a standard procedure in urinalysis. Amongst the formed elements which may be present in urine are cylindrical masses of agglutinated materials that typically represent a mold or "cast" of the lumen of a distal convoluted tubule or collecting tubule. In healthy human subjects, such casts typically have a diameter of 15–25 μm. In subjects with chronic renal failure, however, hypertrophy of the tubules may result in the presence of "broad casts" or "renal failure casts" which are 2–6 times the diameter of normal casts and often have a homogeneous waxy appearance. Thus, as used herein, a "broad cast" means a urinary sediment cast having a diameter of 2–6 times normal, or about 30–150 μm for human casts.

Chronic. As used herein with respect to clinical indications such as urinary casts, measured GFR, or other markers of renal function, "chronic" means persisting for a period of at least three, and more preferably, at least six months. Thus, for example, a subject with a measured GFR chronically below 50% of $GFR_{exp}$ is a subject in which the GFR has been measured and found to be below 50% of $GFR_{exp}$ in at least two measurements separated by at least three, and more preferably, by at least six months, and for which there is no medically sound reason to believe that GFR was substantially (e.g., 10%) higher during the intervening period.

Subjects "At Risk". As used herein, a subject is said to be "at risk" of chronic renal failure, or at risk of the need for renal replacement therapy, if the subject is reasonably expected to suffer a progressive loss of renal function associated with progressive loss of functioning nephron units. Whether a particular subject is at risk is a determination which may routinely be made by one of ordinary skill in the relevant medical or veterinary art. Subjects at risk of chronic renal failure, or at risk of the need for renal replacement therapy, include but are not limited to the following: subjects which may be regarded as afflicted with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, and/or chronic tubulointerstitial sclerosis; subjects having an ultrasound, MRI, CAT scan, or other non-invasive examination indicating renal fibrosis; subjects having an unusual number of broad casts present in urinary sediment; subjects having a GFR which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min, 30 ml/min or 20 ml/min; human female subjects weighing at least about 40 kg and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

II. Description of the Preferred Embodiments

A. General

The present invention depends, in part, upon the surprising discovery that administration of a morphogen to a subject at risk of chronic renal failure, or at risk of a need for renal replacement therapy, can prevent, inhibit or delay the progressive loss of renal function associated with such clinical conditions. In particular, it is now disclosed that the administration of morphogens can prevent, inhibit or delay the progressive loss of functional nephron units and the progressive decline in glomerular filtration rate (GFR) which slowly but inevitably leads to the need for renal replacement therapy (i.e., renal transplant or chronic dialysis) or death. This result is surprising in light of the fact that, although the kidney has previously been disclosed to be an expression source for at least the morphogen OP-1, and although morphogen treatment has previously been indicated for certain traumatic or acute injuries or insults to renal tissue (e.g., ischemia-reperfusion injury, cell-mediated inflammatory injury), the morphogens were not previously known to have any role in ameliorating or mediating the compensatory hypertrophy of renal tissue which is characteristic of chronic renal failure. Furthermore, unlike tissues such as bone or glandular epithelia which retain significant capacity for regeneration, it has generally been believed that new nephron units are not produced after birth, that the ability of the highly differentiated tissues and structures of the kidneys have limited reparative powers and, therefore, that mammals possess a number of nephron units that can only decline during post-natal life.

Without being bound to any particular theory, it is believed that the morphogens of the present invention, and in particular OP-1, have the ability to prevent, inhibit or delay the compensatory hypertrophy which typifies the syndrome of chronic renal failure. This ability may derive from a role of the morphogens in maintaining or preserving the differentiated state of renal tissues even under adverse conditions. Alternatively, or in addition, the morphogens when used according to the invention, are believed to initiate the development of new nephron units by recruiting undifferentiated renal mesenchymal progenitor cells into a nephrogenetic pathway.

B. Morphogens, Inducers and Agonists

Morphogens useful in this invention include eukaryotic proteins originally identified as osteogenic proteins (see U.S. Pat. No. 5,011,691, incorporated herein by reference), such as the OP-1, OP-2, OP-3 and CBMP-2 proteins (SEQ ID NOs: 4–9, 15–22, 25 and 26), as well as amino acid sequence-related proteins such as DPP (SEQ ID NO: 10, from Drosophila), Vgl (SEQ. ID NO: 11, from Xenopus), Vgr-1 (SEQ ID NO: 12, from mouse), GDF-1 (SEQ ID NOs: 13, 30 and 31, from humans, see Lee (1991), *PNAS* 88:4250–4254), 60A (SEQ ID NOs: 23 and 24, from Drosophila, see Wharton et al. (1991) *PNAS* 88:9214–9218), dorsalin-1 (from chick, see Basler et al. (1993) *Cell* 73:687–702 and GenBank accession number L12032) and GDF-5 (from mouse, see Storm et al. (1994) *Nature* 368:639–643). BMP-3 (SEQ ID NO: 26) is also preferred as a morphogen because, like OP-1, it is expressed in renal tissues. Additional useful morphogens include biosynthetic morphogen constructs disclosed in U.S. Pat. No. 5,011,691, e.g., COP-1, 3–5, 7 and 16, as well as others known in the art including dor3, NODAL, UNIVIN, BMP-9, BMP-10, GDF-3, GDF-6, GDF-7, CDMP-2, and SCREW. See also U.S. Pat. No. 4,968,590, incorporated herein by reference.

Naturally occurring proteins identified and/or appreciated herein to be morphogens form a distinct subgroup within the loose evolutionary grouping of sequence-related proteins known as the TGF-β superfamily or supergene family. The naturally occurring morphogens share substantial amino acid sequence homology in their C-terminal regions (domains). Typically, the above-mentioned naturally occurring morphogens are translated as a precursor, having an N-terminal signal peptide sequence, typically less than about 30 residues, followed by a "pro" domain that is cleaved to yield the mature C-terminal domain. The signal peptide is cleaved rapidly upon translation, at a cleavage site that can be predicted in a given sequence using the method of Von Heijne (1986) *Nucleic Acids Research* 14:4683–4691. The pro domain typically is about three times larger than the fully processed mature C-terminal domain. Herein, the "pro" form of a morphogen refers to a morphogen comprising a folded pair of polypeptides each comprising the pro and mature domains of a morphogen polypeptide. Typically, the pro form of a morphogen is more soluble than the mature form under physiological conditions. The pro form appears to be the primary form secreted from cultured mammalian cells.

Table 1, below, summarizes various naturally occurring morphogens identified to date, including their nomenclature as used herein, their Sequence Listing references, and publication sources for the amino acid sequences for the full length proteins not included in the Sequence Listing. Each of the generic terms set forth in Table 1 is intended and should be understood to embrace morphogenically active proteins expressed from nucleic acids encoding the identified sequence mentioned below and set forth in the Sequence Listing, or a morphogenically active fragment or precursor thereof, including functional equivalents thereof such as naturally occurring and biosynthetic variants thereof.

Naturally occurring variants thereof include allelic variant forms isolated from other individuals of a single biological species, and phylogenetic counterpart (species) variant forms (homologues) isolated from phylogenetically distinct biological species. The disclosure of publications mentioned below is incorporated herein by reference.

TABLE 1

| | |
|---|---|
| "OP-1" | Refers generically to morphogenically active proteins expressed from nucleic acid encoding the human OP-1 protein disclosed in SEQ ID NO: 4 ("hOP-1"), and includes at least mouse OP-1, SEQ ID NO: 5 ("mOP-1"). In each of human and mouse OP-1, SEQ ID NOs: 4 and 5, the conserved seven cysteine skeleton is defined by residues 38 to 139. cDNA sequences and amino acid sequences encoded therein and corresponding to the fill length proteins are provided in SEQ ID NOs: 15 and 16 (hOP-1) and SEQ ID NOs: 17 and 18 (mOP-1.) The mature proteins are defined by residues 293-431 (hOP-1) and 292-430 (mOP-1). The "pro" regions of the proteins, cleaved to yield the mature, morphogenically active proteins are defined essentially by residues 30-292 (hOP-1) and residues 30-291 (mOP-1). |
| "OP-2" | Refers generically to morphogenically active proteins expressed from a nucleic acid encoding the human OP-2 protein disclosed in SEQ ID NO: 6 ("hOP-2"), and includes at least mouse OP-2 ("mOP-2", SEQ ID NO: 7). In each of human and mouse OP-2, the conserved seven cysteine skeleton is defined by residues 38 to 139 of SEQ ID NOs: 6 and 7. cDNA sequences and amino acid sequences encoded therein and corresponding to the full length proteins are provided in SEQ ID NOs: 19 and 20 (hOP-2) and SEQ ID NOs: 21 and 22 (mOP-2.) The mature proteins are defined essentially by residues 264-402 (hOP-2) and 261–399 (mOP-2). The "pro" regions of the proteins, cleaved to yield the mature, morphogenically active proteins are defined essentially by residues 18–263 (hOP-2) and residues 18-260 (mOP-1). |
| "OP-3" | Refers generically to morphogenically active proteins expressed from a nucleic acid encoding the mouse OP-3 protein disclosed in SEQ ID NO: 26 ("mOP-3"). The conserved seven cysteine domain is defined by residues 298 to 399 of SEQ ID NO: 26, which shares greater than 79% amino acid identity with the corresponding mOP-2 and hOP-2 sequences, and greater than 66% identity with the corresponding OP-1 sequences. A cDNA sequence encoding the above-mentioned amino acid sequence is provided in SEQ ID NO: 25. OP-3 is unique among the morphogens identified to date in that the residue at position 9 in the conserved seven cysteine domain (e.g., residue 315 of SEQ ID NO: 26) is a serine, whereas other morphogens typically have a tryptophan at this location. |
| "CBMP-2" | Refers generically to morphogenically active proteins expressed from a nucleic acid encoding the CBMP-2 proteins, including at least human CBMP-2A ("CBMP-2A(fx)", SEQ ID NO: 8) and human CBMP-2B ("CBMP-2B(fx)", SEQ ID NO: 9). The amino acid sequence for the full length proteins, referred to in the literature as BMP-2A and BMP-2B, or BMP-2 and BMP-4, appear in Wozney, et al. (1988) Science 242: 1528-1534. The pro domain for BMP-2 (BMP-2A) likely includes residues 25–248; the mature protein, residues 249–396. The pro domain for BMP-4 (BMP-2B) likely includes residues 25–256; the mature protein, residues 257–408. |
| "DPP(fx)" | refers to proteins encoded by the Drosophila DPP gene and defining the conserved seven cysteine skeleton (SEQ ID NO: 10). The amino acid sequence for the full length protein appears in Padgett, et al. (1987) Nature 325:81–84. The pro domain likely extends from the signal peptide cleavage site to residue 456; the mature protein likely is defined by residues 457–588. |
| "Vgl(fx)" | refers to proteins encoded by the Xenopus Vgl gene and defining the conserved seven cysteine skeleton (SEQ ID NO: 11). The amino acid sequence for the full length protein appears in Weeks (1987) Cell 51 :861–867. The prodomain likely extends from the signal peptide cleavage site to residue 246; the mature protein likely is defined by residues 247–360. |
| "Vgr-1(fx)" | refers to proteins encoded by the murine Vgr-1 gene and defining the conserved seven cysteine skeleton (SEQ ID NO: 12). The amino acid sequence for the full length protein appears in Lyons, et al. (1989) PNAS 86:4554–4558. The prodomain likely extends from the signal peptide cleavage site to residue 299; the mature protein likely is defined by residues 300–438. |
| "GDF-1(fx)" | refers to proteins encoded by the human GDF-1 gene and defining the conserved seven cysteine skeleton (SBQ ID NO: 13). The cDNA and encoded amino sequence for the full length protein are provided in SEQ ID NOs: 30 and 31. The prodomain likely extends from the signal peptide cleavage site to residue 214; the mature protein likely is defined by residues 215–372. |
| "60A" | refers generically to morphogenically active proteins expressed from nucleic acid (e.g., the Drosophila 60A gene) encoding 60A protein or morphogenically active fragments thereof (see SEQ ID NOs: 23 and 24 wherein the cDNA and encoded amino acid sequence for the full length protein are provided). "60A(fx)" refers to the protein sequences defining the conserved seven cysteine skeleton (residues 354 to 455 of SEQ ID NO: 24.) The prodomain likely extends from the signal peptide cleavage site to residue 324; the mature protein likely is defined by residues 325–455. The 60A protein is considered likely herein to be a phylogenetic counterpart variant of the human and mouse OP-1 genes; Sampath, et al. (1993) PNAS 90:6004–6008. |
| "BMP-3(fx)" | refers to proteins encoded by the human BMP-3 gene and defining the |

TABLE 1-continued conserved seven cysteine skeleton (SBQ ID NO: 26). The amino acid sequence for the full length protein appears in Wozney, et al. (1988) Science 242: 1528–1534. The pro domain likely extends from the signal peptide cleavage site to residue 290; the mature protein likely is defined by residues 291–472.

"BMP-5(fx)" refers to proteins encoded by the human BMP-5 gene and defining the conserved seven cysteine skeleton (SEQ ID NO: 27). The amino acid sequence for the full length protein appears in Celeste, et al. (1991) PNAS 87:9843–9847. The pro domain likely extends from the signal peptide cleavage site to residue 316; the mature protein likely is defined by residues 317–454.

"BMP-6(fx)" refers to proteins encoded by the human BMP-6 gene and defining the conserved seven cysteine skeleton (SEQ ID NO: 28). The amino acid sequence for the full length protein appears in Celeste, et al. (1990) PNAS 87:9843–5847. The pro domain likely includes extends from the signal peptide cleavage site to residue 374; the mature sequence likely includes residues 375–513.

As shown in FIG. 7, the OP-2 and OP-3 proteins have an additional cysteine residue in the conserved C-terminal region (e.g., see residue 41 of SEQ ID NOs: 6 and 7), in addition to the conserved cysteine skeleton or domain in common with the other known proteins in this family. The GDF-1 protein has a four amino acid insert within the conserved skeleton (residues 44–47 of SEQ ID NO: 13) but this insert likely does not interfere with the relationship of the cysteines in the folded structure. Further, the CBMP-2 proteins are missing one amino acid residue within the cysteine skeleton. Thus, these morphogen polypeptides illustrate principles of alignment used herein with respect to the preferred reference morphogen sequence of human OP-1, residues 38–139 of SEQ ID NO: 4.

In certain preferred embodiments, morphogens useful herein include those in which the amino acid sequences of morphogen polypeptides comprise a sequence sharing at least 70% amino acid sequence homology or "similarity", and preferably 80% homology or similarity with a reference morphogen selected from the foregoing naturally occurring morphogens. Preferably, the reference morphogen is human OP-1, and the reference sequence thereof is the C-terminal seven cysteine domain present in morphogenically active forms of human OP-1, residues 38–139 of SEQ ID NO: 4. Morphogens useful herein accordingly include allelic, phylogenetic counterpart and other variants of the preferred reference sequence, whether naturally-occurring or biosynthetically produced (e.g., including "muteins" or "mutant proteins"), as well as novel members of the morphogenic family of proteins including the morphogens set forth and identified above, e.g., in connection with Table 1. Certain particularly preferred morphogen polypeptides share at least 60% amino acid identity with the preferred reference sequence of human OP-1, still more preferably at least 65% amino acid identity therewith.

In other preferred embodiments, the family of morphogen polypeptides useful in the present invention, and members thereof, are defined by a generic amino acid sequence. For example, Generic Sequence 7 (SEQ ID NO: 1) and Generic Sequence 8 (SEQ ID NO: 2) disclosed below, accommodate the homologies shared among preferred morphogen protein family members identified to date, including at least OP-1, OP-2, OP-3, CBMP-2A, CBMP-2B, BMP-3, 60A, DPP, Vgl, BMP-5, BMP-6, Vgr-1, and GDF-1 (SEQ ID NOs: 4–15, 24, and 26–29). The amino acid sequences for these proteins are described herein (see Sequence Listing) and/or in the art, as summarized above. The generic sequences include both the amino acid identity shared by these sequences in the C-terminal domain, defined by the six and seven cysteine skeletons (Generic Sequences 7 and 8, respectively), as well as alternative residues for the variable positions within the sequence. The generic sequences provide an appropriate cysteine skeleton where inter- or intramolecular disulfide bonds can form, and contain certain critical amino acids likely to influence the tertiary structure of the folded proteins. In addition, the generic sequences allow for an additional cysteine at position 41 (Generic Sequence 7) or position 46 (Generic Sequence 8), thereby encompassing the morphogenically active sequences of OP-2 and OP-3.

```
              Generic Sequence 7
              Leu Xaa Xaa Xaa Phe Xaa Xaa
               1                5

Xaa Gly Trp Xaa Xaa Xaa Xaa Xaa Xaa Pro
               10                      15

Xaa Xaa Xaa Xaa Ala Xaa Tyr Cys Xaa Gly
               20                      25

Xaa Cys Xaa Xaa Pro Xaa Xaa Xaa Xaa Xaa
               30                      35

Xaa Xaa Xaa Asn His Ala Xaa Xaa Xaa Xaa
               40                      45

Xaa Xaa Xaa Xaa Xaa Xaa Xaa Xaa Xaa Xaa
               50                      55

Xaa Xaa Xaa Cys Cys Xaa Pro Xaa Xaa Xaa
               60                      65

Xaa Xaa Xaa Xaa Xaa Leu Xaa Xaa Xaa Xaa
               70                      75

Xaa Xaa Xaa Val Xaa Leu Xaa Xaa Xaa Xaa
               80                      85

Xaa Met Xaa Val Xaa Xaa Cys Xaa Cys Xaa
               90                      95
``` wherein each Xaa independently is selected from a group of one or more specified amino acids defined as follows: "Res." means "residue" and Xaa at res.2=(Tyr or Lys); Xaa at res.3=Val or Ile); Xaa at res.4=(Ser, Asp or Glu); Xaa at res.6=(Arg, Gln, Ser, Lys or Ala); Xaa at res.7=(Asp or Glu); Xaa at res.8=(Leu, Val or Ile); Xaa at res.11=(Gln, Leu, Asp, His, Asn or Ser); Xaa at res.12=(Asp, Arg, Asn or Glu); Xaa at res.13=(Trp or Ser); Xaa at res.14=(Ile or Val); Xaa at res.15=(Ile or Val); Xaa at res.16 (Ala or Ser); Xaa at res.18=(Glu, Gln, Leu, Lys, Pro or Arg); Xaa at res.19=(Gly or Ser); Xaa at res.20=(Tyr or Phe); Xaa at res.21=(Ala, Ser, Asp, Met, His, Gln, Leu or Gly); Xaa at res.23=(Tyr, Asn or Phe); Xaa at res.26=(Glu, His, Tyr, Asp, Gin, Ala or Ser); Xaa at res.28=(Glu, Lys, Asp, Gln or Ala); Xaa at res.30= (Ala, Ser, Pro, Gin, Ile or Asn); Xaa at res.31=(Phe, Leu or Tyr); Xaa at res.33=(Leu, Val or Met); Xaa at res.34=(Asn, Asp, Ala, Thr or Pro); Xaa at res.35=(Ser, Asp, Glu, Leu, Ala or Lys); Xaa at res.36=(Tyr, Cys, His, Ser or Ile); Xaa at res.37=(Met, Phe, Gly or Leu); Xaa at res.38=(Asn, Ser or Lys); Xaa at res.39=(Ala, Ser, Gly or Pro); Xaa at res.40= (Thr, Leu or Ser); Xaa at res.44=(Ile, Val or Thr); Xaa at res.45=(Val, Leu, Met or Ile); Xaa at res.46=(Gln or Arg); Xaa at res.47=(Thr, Ala or Ser); Xaa at res.48=(Leu or Ile); Xaa at res.49=(Val or Met); Xaa at res.50=(His, Asn or Arg); Xaa at res.51=(Phe, Leu, Asn, Ser, Ala or Val); Xaa at res.52=(Ile, Met, Asn, Ala, Val, Gly or Leu); Xaa at res.53= (Asn, Lys, Ala, Glu, Gly or Phe); Xaa at res.54=(Pro, Ser or Val); Xaa at res.55=(Glu, Asp, Asn, Gly, Val, Pro or Lys); Xaa at res.56=(Thr, Ala, Val, Lys, Asp, Tyr, Ser, Gly, Ile or His); Xaa at res.57=(Val, Ala or Ile); Xaa at res.58=(Pro or Asp); Xaa at res.59=(Lys, Leu or Glu); Xaa at res.60=(Pro, Val or Ala); Xaa at res.63=(Ala or Val); Xaa at res.65=(Thr, Ala or Glu); Xaa at res.66=(Gln, Lys, Arg or Glu); Xaa at res.67=(Leu, Met or Val); Xaa at res.68=(Asn, Ser, Asp or Gly); Xaa at res.69=(Ala, Pro or Ser); Xaa at res.70=(Ile, Thr, Val or Leu); Xaa at res.71=(Ser, Ala or Pro); Xaa at res.72=(Val, Leu, Met or Ile); Xaa at res.74=(Tyr or Phe); Xaa at res.75=(Phe, Tyr, Leu or His); Xaa at res.76=(Asp, Asn or Leu); Xaa at res.77=(Asp, Glu, Asn, Arg or Ser); Xaa at res.78=(Ser, Gln, Asn, Tyr or Asp); Xaa at res.79=(Ser, Asn, Asp, Glu or Lys); Xaa at res.80=(Asn, Thr or Lys); Xaa at res.82=(Ile, Val or Asn); Xaa at res.84=(Lys or Arg); Xaa at res.85=(Lys, Asn, Gln, His, Arg or Val); Xaa at res.86= (Tyr, Glu or His); Xaa at res.87=(Arg, Gln, Glu or Pro); Xaa at res.88=(Asn, Glu, Trp or Asp); Xaa at res.90=(Val, Thr, Ala or Ile); Xaa at res.92=(Arg, Lys, Val, Asp, Gln or Glu); Xaa at res.93=(Ala, Gly, Glu or Ser); Xaa at res.95=(Gly or Ala) and Xaa at res.97=(His or Arg).

Generic Sequence 8 (SEQ ID NO: 2) includes all of Generic Sequence 7 and in addition includes the following sequence (SEQ ID NO: 14) at its N-terminus:

```
Cys Xaa Xaa Xaa Xaa
 1               5
```

Accordingly, beginning with residue 7, each "Xaa" in Generic Sequence 8 is a specified amino acid defined as for Generic Sequence 7, with the distinction that each residue number described for Generic Sequence 7 is shifted by five in Generic Sequence 8. Thus, "Xaa at res.2=(Tyr or Lys)" in Generic Sequence 7 refers to Xaa at res. 7 in Generic Sequence 8. In Generic Sequence 8, Xaa at res.2=(Lys, Arg, Ala or Gln); Xaa at res.3=(Lys, Arg or Met); Xaa at res.4=(His, Arg or Gln); and Xaa at res.5=(Glu, Ser, His, Gly, Arg, Pro, Thr, or Tyr).

As noted above, certain currently preferred morphogen polypeptide sequences useful in this invention have greater than 60% identity, preferably greater than 65% identity, with the amino acid sequence defining the preferred reference sequence of hOP-1. These particularly preferred sequences include allelic and phylogenetic counterpart variants of the OP-1 and OP-2 proteins, including the Drosophila 60A protein. Accordingly, in certain particularly preferred embodiments, useful morphogens include active proteins comprising pairs of polypeptide chains within the generic amino acid sequence herein referred to as "OPX" (SEQ ID NO: 3), which defines the seven cysteine skeleton and accommodates the homologies between several identified variants of OP-1 and OP-2. As described therein, each Xaa at a given position independently is selected from the residues occurring at the corresponding position in the C-terminal sequence of mouse or human OP-1 or OP-2 (see SEQ ID NOs: 4–7 and/or SEQ ID NOs: 15–22).

In still other preferred embodiments, useful morphogen polypeptides have amino acid sequences comprising a sequence encoded by nucleic acid that hybridizes, under stringent hybridization conditions, to DNA or RNA encoding reference morphogen sequences, e.g., C-terminal sequences defining the conserved seven cysteine domains of OP-1 or OP-2, e.g., nucleotides 1036–1341 and nucleotides 1390–1695 of SEQ ID NO: 15 and 19, respectively. As used herein, stringent hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C.

As noted above, morphogens useful in the present invention generally are dimeric proteins comprising a folded pair of the above polypeptides. Morphogens are inactive when reduced, but are active as oxidized homodimers and when oxidized in combination with other morphogens of this invention to produce heterodimers. Thus, members of a folded pair of morphogen polypeptides in a morphogenically active protein can be selected independently from any of the specific morphogen polypeptides mentioned above.

The morphogens useful in the methods, compositions and devices of this invention include proteins comprising any of the polypeptide chains described above, whether isolated from naturally-occurring sources, or produced by recombinant DNA or other synthetic techniques, and includes allelic and phylogenetic counterpart variants of these proteins, as well as biosynthetic variants (muteins) thereof, and various truncated and fusion constructs. Deletion or addition mutants also are envisioned to be active, including those which may alter the conserved C-terminal six or seven cysteine domain, provided that the alteration does not functionally disrupt the relationship of these cysteines in the folded structure. Accordingly, such active forms are considered the equivalent of the specifically described constructs disclosed herein. The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogenic proteins can be expressed from intact or truncated cDNA or from synthetic DNAs in prokaryotic or eukaryotic host cells, and purified, cleaved, refolded, and dimerized to form morphogenically active compositions. Currently preferred host cells include E. coli or mammalian cells, such as CHO, COS or BSC cells. A detailed description of the morphogens useful in the methods, compositions and devices of this invention is disclosed in published application WO92/15323, the disclosure or which is incorporated by reference herein.

Thus, in view of this disclosure, skilled genetic engineers can isolate genes from cDNA or genomic libraries of various different biological species, which encode appropriate amino acid sequences, or construct DNAs from oligonucleotides, and then can express them in various types of host cells, including both prokaryotes and eukaryotes, to produce large quantities of active proteins capable of stimulating the morphogenesis of, and/or inhibiting damage or loss of, mammalian renal tissues.

As noted above, a protein is morphogenic herein generally if it induces the developmental cascade of cellular and molecular events that culminate in the formation of new, organ-specific tissue. Preferably, a morphogen comprises a pair of polypeptides having a sequence that corresponds to or is functionally equivalent to at least the conserved C-terminal six or seven cysteine skeleton of human OP-1, included in SEQ ID NO: 4. The morphogens generally are competent to induce all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells. Details of how the morphogens useful in this invention first were identified, as well as a description on how to make, use and test them for morphogenic activity are disclosed in published application WO92/15323. As disclosed therein, the morphogens can be purified from naturally-sourced material or recombinantly produced from prokaryotic or eukaryotic host cells, using the genetic sequences disclosed therein. Alternatively, novel morphogenic sequences can be identified following the procedures disclosed therein.

Exemplary useful morphogens include naturally derived proteins comprising a pair of polypeptides, the amino acid sequences of which comprise one or more of the sequences disclosed in the Sequence Listing and FIG. 7. Other useful sequences include those of the naturally derived morphogens dorsalin-1, SCREW, NODAL, UNIVIN and GDF-5, discussed herein in connection with Table 1, as well as biosynthetic constructs disclosed in U.S. Pat. No. 5,011,691, the disclosure of which is incorporated herein by reference (e.g., COP-1, COP-3, COP-4, COP-5, COP-7, and COP-16).

Accordingly, certain preferred morphogens useful in the methods and compositions of this invention can be described as morphogenically active proteins having amino acid sequences sharing 70% or, preferably, 80% homology (similarity) with a reference morphogen sequence described above, e.g., residues 38–139 of SEQ ID NO: 4, where "homology" is as defined herein above. Alternatively, in other preferred embodiments, morphogens useful in the methods and compositions disclosed herein fall within the family of polypeptides described by Generic Sequence 7, SEQ ID NO: 1, more preferably by Generic Sequence 8, SEQ ID NO: 2.

FIG. 7 herein sets forth an alignment of the amino acid sequences of the active regions of naturally occurring proteins that have been identified or appreciated herein as morphogens, including human OP-1 (hOP-1, SEQ ID NOs: 4 and 15–16), mouse OP-1 (mOP-1, SEQ ID NOs: 5 and 17–18), human and mouse OP-2 (SEQ ID NOs: 6, 7, and 19–22), mouse OP-3 (SEQ ID NOs: 25–26), CBMP-2A (SEQ ID NO: 8), CBMP-2B (SEQ ID NO: 9), BMP-3 (SEQ ID NO: 27), DPP (from Drosophila, SEQ ID NO: 10), Vgl, (from Xenopus, SEQ ID NO: 11), Vgr-1 (from mouse, SEQ ID NO: 12), GDF-1 (from mouse and/or human, SEQ ID NOs: 13, 30 and 31), 60A protein (from Drosophila, SEQ ID NOs: 23 and 24), BMP-5 (SEQ ID NO: 28) and BMP-6 (SEQ ID NO: 29). The sequences are aligned essentially following the method of Needleman, et al. (1970) *J. Mol. Biol.*, 48:443–453, calculated using the Align Program (DNAstar, Inc.). In FIG. 7, three dots indicates that the amino acid in that position is the same as the corresponding amino acid in hOP-1. Three dashes indicates that no amino acid is present in that position, and are included for purposes of illustrating homologies. For example, amino acid residue 60 of CBMP-2A and CBMP-2B is "missing." Of course, both of these amino acid sequences in this region comprise Asn-Ser (residues 58, 59), with CBMP-2A then comprising Lys and Ile, whereas CBMP-2B comprises Ser and Ile. FIG. 7 also illustrates the handling of insertions in the morphogen amino acid sequence: between residues 56 and 57 of BMP-3 is an inserted Val residue; between residues 43 and 44 of GDF-1 is inserted the amino acid sequence, Gly-Gly-Pro-Pro. Such deviations from the reference morphogen sequence are ignored for purposes of calculating the defined relationship between, e.g., GDF-1 and hOP-1. As is apparent from the amino acid sequence comparisons set forth in FIG. 7, significant amino acid changes can be made from the reference sequence while retaining morphogenic activity. For example, while the GDF-1 protein sequence depicted in FIG. 7 shares only about 50% amino acid identity with the hOP-1 sequence described therein, the GDF-1 sequence shares greater than 70% amino acid sequence homology (or "similarity") with the hOP-1 sequence, where "homology" or "similarity" includes allowed conservative amino acid substitutions within the aligned sequence, e.g., as defined by Dayhoff, et al. (1979) 5 *Atlas of Protein Sequence and Structure* Suppl. 3, pp. 345–362, (M. O. Dayhoff, ed., Natl. BioMed. Res. Found., Washington D.C.).

The currently most preferred protein sequences useful as morphogens in this invention include those having greater than 60% identity, preferably greater than 65% identity, with the amino acid sequence defining the conserved six or seven cysteine skeleton of hOP-1 (e.g., residues 43–139 or 38–139 of SEQ ID NO: 5). These most preferred sequences include both allelic and phylogenetic counterpart variants of the OP-1 and OP-2 proteins, including the Drosophila 60A protein. Accordingly, in still another preferred aspect, the invention includes morphogens comprising species of polypeptide chains having the generic amino acid sequence referred to herein as "OPX", which defines the seven cysteine domain and accommodates the identities and homologies between the various identified OP-1 and OP-2 proteins. OPX is presented in SEQ ID NO: 3. As described therein, each Xaa at a given position independently is selected from the residues occurring at the corresponding position in the C-terminal sequence of mouse or human OP-1 or OP-2 (see FIG. 7 and SEQ ID NOs: 4–7 and/or SEQ ID NOs: 15–22).

Alternatively, an effective amount of an agent competent to stimulate or induce increased endogenous morphogen expression in a mammal may be administered by any of the routes described herein. For example, an agent competent to stimulate or induce morphogen production and/or secretion from renal tissue may be provided to a mammal, e.g., by systemic administration to the mammal or by direct administration of the morphogen-stimulating agent to renal tissue. Alternatively, the morphogen-stimulating agent or "morphogen inducer" may induce morphogen expression and/or secretion at a distant site (e.g., at a tissue locus other than renal tissue), with the expressed morphogen circulating to renal tissue competent to take up the morphogen and respond thereto. A method for identifying and testing agents competent to modulate the levels of endogenous morphogens in a given tissue is described in detail in published applications WO93/05172 and WO93/05751, the teachings of which are incorporated herein by reference. Briefly, candidate compounds can be identified and tested by incubation in vitro with a test tissue or cells thereof, or a cultured cell line derived therefrom, for a time sufficient to allow the compound to affect the production, i.e., the expression and/or secretion, of a morphogen produced by the cells of that tissue. Here, suitable tissue, or cultured cells of a suitable tissue, preferably can be selected from renal epithelium, fibroblasts, and osteoblasts.

In another series of embodiments, an agent which acts as an agonist of a morphogen receptor may be administered instead of the morphogen itself. Such an agent may also be referred to an a morphogen "mimic," "mimetic," or "analog." Thus, for example, a small peptide or other molecule which can mimic the activity of a morphogen in binding to and activating the morphogen's receptor may be employed as an equivalent of the morphogen. Preferably the agonist is a full agonist, but partial morphogen receptor agonists may also be advantageously employed. Methods of identifying such agonists are known in the art and include assays for compounds which induce morphogen-mediated responses (e.g., induction of differentiation of metanephric mesenchyme, induction of endochondral bone formation). For example, methods of identifying morphogen inducers or agonists of morphogen receptors may be found in U.S. Ser. No. 08/478,097 filed Jun. 7, 1995 and U.S. Ser. No. 08/507, 598 filed Jul. 26, 1995, the disclosures of which are incorporated herein by reference.

Finally, as described below, in other embodiments cells may be implanted into the kidney of a subject at risk of chronic renal failure, or at risk of needing renal replacement therapy, in order to serve as a source of morphogen and/or to provide a source of additional functional renal tissue. Such cells may be host or donor cells which normally express morphogens, which have been transformed so as to express morphogens, or which have been treated with morphogens to induce metanephric differentiation.

C. Subjects for Treatment

As a general matter, the methods of the present invention may be utilized for any mammalian subject at risk of chronic renal failure, or at risk of the need for renal replacement therapy (i.e., chronic dialysis or renal transplant). Mammalian subjects which may be treated according to the methods of the invention include, but are not limited to, human subjects or patients. In addition, however, the invention may be employed in the treatment of domesticated mammals which are maintained as human companions (e.g., dogs, cats, horses), which have significant commercial value (e.g., dairy cows. beef cattle, sporting animals), which have significant scientific value (e.g., captive or free specimens of endangered species), or which otherwise have value. In addition, as a general matter, the subjects for treatment with the methods of the present invention need not present indications for morphogen treatment other than those associated with risk of chronic renal failure. That is, the subjects for treatment are expected to be otherwise free of indications for morphogen treatment. In some number of cases, however, the subjects may present with other symptoms (e.g., osteodystrophy) for which morphogen treatment would be indicated. In such cases, the morphogen treatment should be adjusted accordingly so to avoid excessive dosing.

One of ordinary skill in the medical or veterinary arts is trained to recognize subjects which may be at a substantial risk of chronic renal failure, or at substantial risk of the need for renal replacement therapy. In particular, clinical and non-clinical trials, as well as accumulated experience, relating to the presently disclosed and other methods of treatment, are expected to inform the skilled practitioner in deciding whether a given subject is at risk of chronic renal failure, or at risk of needing renal replacement therapy, and whether any particular treatment is best suited to the subject's needs, including treatment according to the present invention.

As a general matter, a mammalian subject may be regarded as being at risk of chronic renal failure, or at risk of needing renal replacement therapy, if that subject has already been diagnosed as afflicted with, or would be regarded as being afflicted with, a condition which typically leads to progressive loss of renal function associated with progressive loss of functioning nephron units. Such conditions include, but are not limited to, chronic renal failure, end-stage renal disease, chronic diabetic nephropathy, hypertensive nephrosclerosis, chronic glomerulonephritis, hereditary nephritis, renal dysplasia and the like. These, and other diseases and conditions known in the art, typically lead to a progressive loss of functioning nephrons and to the onset of chronic renal failure.

Frequently, one of skill in the medical or veterinary arts may base a prognosis, diagnosis or treatment decision upon an examination of a renal biopsy sample. Such biopsies provide a wealth of information useful in diagnosing disorders of the kidney but, due to the invasiveness of the procedure, and the additional trauma to a presumably unhealthy kidney, may not be appropriate for all subjects. Nonetheless, subjects at risk of chronic renal failure, or at risk of needing renal replacement therapy, may be recognized by histological indications from renal biopsies including, but not limited to, glomerular hypertrophy, tubular hypertrophy, glomerulosclerosis, tubulointerstitial sclerosis, and the like.

Less invasive techniques for assessing kidney morphology include MRI, CAT and ultrasound scans. Scanning techniques are also available which employ contrasting or imaging agents (e.g., radioactive dyes) but, it should be noted, some of these are particularly toxic to renal tissues and structures and, therefore, their use may be ill-advised in subjects at risk of chronic renal failure. Such non-invasive scanning techniques may be employed to detect conditions such as renal fibrosis or sclerosis, focal renal necrosis, renal cysts, and renal gross hypertrophy which will place a subject at risk of chronic renal failure, or at risk of needing renal replacement therapy.

Quite frequently, prognosis, diagnosis and/or treatment decisions are based upon clinical indications of renal function. One such indication is the presence in urinary sediment of an unusual number of "broad" or "renal failure" casts, which is indicative of tubular hypertrophy and suggests the compensatory renal hypertrophy which typifies chronic renal failure. A better indication of renal function is the glomerular flow rate (GFR), which can be measured directly by quantifying the rate of clearance of particular markers, or which may be inferred from indirect measurements.

It should be noted that the present invention is not directed to the measurement of GFR or to the diagnosis of chronic renal failure. The methods of treatment of the present invention need not, therefore, be restricted to subjects presenting with any particular measures of GFR, or any other particular marker of renal function. Indeed, it is not necessary that the GFR of a subject, or any other particular marker of renal function, be determined before practicing the treatments of the present invention. Nonetheless, the measurement of GFR is considered to be a preferred means of assessing renal function.

As is well known in the art, GFR reflects the rate of clearance of a reference or marker compound from the plasma to the urine. The marker compound to be considered is typically one which is freely filtered by the glomeruli, but which is not actively secreted or reabsorbed by the renal tubules, and which is not significantly bound by circulating proteins. The rate of clearance is typically defined by the formula, presented above, which relates the volume of urine produced in a twenty-four period, and the relative concentrations of the marker in the urine and plasma. To be more accurate, the GFR should also be corrected for body surface area. The "gold standard" reference compound is inulin because of its filtration properties and lack of serum-binding. The concentration of this compound is, however, difficult to quantify in blood or urine. The clearance rates of other compounds, including p-aminohippurate (PAH) and creatinine, are therefore often used instead of inulin. In addition, various formulas are often employed which seek to simplify the estimation of actual GFR by omitting considerations of actual urine concentrations of the marker, actual daily volumes of urine produced, or actual body surface area. These values may be replaced by estimates based on other factors, by baseline values established for the same subject, or by standard values for similar subjects. These estimates should be used with caution, however, as they may entail inappropriate assumptions based upon the renal function of normal or healthy subjects.

In addition to measurements or estimates of actual GFR, various methods and formulas have been developed in the art which describe an expected value of GFR for a healthy subject with certain characteristics. In particular, formulas are available which provide an expected value of the GFR based upon plasma creatinine levels, age, weight and sex. One such formula for an expected GFR is presented above. Other formulas may, of course, be employed and tables of standard values may be produced for subject's of a given age, weight, sex, and/or plasma creatinine concentration. Newer methods of measuring or estimating GFR (e.g., using NMR or MRI technologies) are also now available in the art and may be used in accordance with the present invention (see, e.g., U.S. Pat. Nos. 5,100,646 and 5,335,660).

As a general matter, irrespective of the manner in which GFR is measured or estimated, a subject may be considered to be at risk of chronic renal failure, or at risk of needing renal replacement therapy, when the subject has a GFR which is chronically less than about 50% of the expected GFR for that subject. The risk is considered greater as the GFR falls lower. Thus, a subject is increasingly considered at risk if the subject has a GFR which is chronically less than about 40%, 30% or 20% of the expected GFR.

As a general matter, irrespective of the manner in which GFR is measured or estimated, a human male subject weighing at least about 50 kg may be considered to be at risk of chronic renal failure, or at risk of needing renal replacement therapy, when the subject has a GFR which is chronically less than about 50 ml/min. The risk is considered greater as the GFR falls lower. Thus, a subject is increasingly considered at risk if the subject has a GFR which is chronically less than about 40, 30 or 20 ml/min.

As a general matter, irrespective of the manner in which GFR is measured or estimated, a human female subject weighing at least about 40 kg may be considered to be at risk of chronic renal failure, or at risk of needing renal replacement therapy, when the subject has a GFR which is chronically less than about 40 ml/min. The risk is considered greater as the GFR falls lower. Thus, a subject is increasingly considered at risk if the subject has a GFR which is chronically less than about 30, 20 or 10 ml/min.

By a employing a variety of methods, including the histological examinations, non-invasive scanning procedures, evaluations of clinical indicators, and other techniques described above and known in the art, those in the medical and veterinary arts may provide estimates of either the number of functioning nephron units which a subject possesses, or the percentage of functioning nephron units which a subject possesses relative to a healthy but otherwise similar subject (e.g., a conspecific subject of approximately the same age, weight, and sex). Thus, for example, a biopsy may reveal a decrease in the density of functional nephrons, or imaging with filtered agents may indicate losses of functional renal tissue and/or filtering capacity. Such measures or estimates provide another means of expressing when a subject is at risk of chronic renal failure, or at risk of needing renal replacement therapy. Thus, as a general matter, a subject may be regarded to be at risk of chronic renal failure, or at risk of needing renal replacement therapy, if that subject possesses a number of functional nephron units which is less than about 50% of the number of functional nephron units of a healthy, but otherwise similar, subject. As above, the risk is considered greater as the number of functional nephrons decreases further. Thus, a subject is increasingly considered at risk if the subject has a number of functional nephrons which is less than about 40, 30 or 20% of the number for a similar but healthy subject.

Finally, it should be noted that subjects possessing a single kidney, irrespective of the manner of loss of the other kidney (e.g., physical trauma, surgical removal, birth defect), may be considered to be prima facie at risk of chronic renal failure, or the need for renal replacement therapy. This is particularly true for those subjects in which one kidney has been lost due to a disease or condition which may afflict the remaining kidney. Similarly, subjects which are already recipients of a renal transplant, or which are already receiving chronic dialysis (e.g., chronic hemodialysis or continuous ambulatory peritoneal dialysis) may be considered prima facie to be at risk of chronic renal failure, or the need for further renal replacement therapy.

D. Formulations and Methods of Treatment

The morphogens, morphogen inducers, or agonists of morphogen receptors of the present invention may be administered by any route which is compatible with the particular morphogen, inducer, or agonist employed. Thus, as appropriate, administration may be oral or parenteral, including intravenous, intraperitoneal, and renal intracapsular routes of administration. In addition, administration may be by periodic injections of a bolus of the morphogen, inducer or agonist, or may be made more continuous by intravenous or intraperitoneal administration from a reservoir which is external (e.g., an i.v. bag) or internal (e.g., a bioerodable implant).

The therapeutic agents of the invention (i.e., morphogens, morphogen inducers or agonists of morphogen receptors) may be provided to an individual by any suitable means, preferably directly (e.g., locally, as by injection or topical administration to a tissue locus) or systemically (e.g., parenterally or orally). Where the agent is to be provided parenterally, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or by aerosol administration, the agent preferably comprises part of an aqueous solution. The solution is physiologically acceptable so that in addition to delivery of the desired agent to the patient, the solution does not otherwise adversely affect the patient's electrolyte and/or volume balance. The aqueous medium for the agent thus may comprise normal physiologic saline (e.g., 9.85% NaCl, 0.15M, pH 7–7.4). Such an aqueous solution containing the agent can be made, for example, by dissolving the agent in 50% ethanol containing acetonitrile in 0.1% trifluoroacetic acid (TFA) or 0.1% HCl, or equivalent solvents. One volume of the resultant solution then is added, for example, to ten volumes of phosphate buffered saline (PBS), which further may include 0.1–0.2% human serum albumin (HSA). The resultant solution preferably is vortexed extensively.

If desired, a given morphogen or other agent may be made more soluble by association with a suitable molecule. For example, association of the mature morphogen dimer with the pro domain results in the pro form of the morphogen which typically is more soluble or dispersible in physiological solutions than the corresponding mature form. In fact, endogenous morphogens are thought to be transported (e.g., secreted and circulated) in the mammalian body in this form. This soluble form of the protein can be obtained from culture medium of morphogen-secreting mammalian cells, e.g., cells transfected with nucleic acid encoding and competent to express the morphogen. Alternatively, a soluble species can be formulated by complexing the mature dimer (or an active fragment thereof) with a morphogen pro domain or a solubility-enhancing fragment thereof (described more fully below). Another molecule capable of enhancing solubility and particularly useful for oral administrations, is casein. For example, addition of 0.2% casein increases solubility of the mature active form of OP-1 by 80%. Other components found in milk and/or various serum proteins also may be useful.

Useful solutions for parenteral administration may be prepared by any of the methods well known in the pharmaceutical art, described, for example, in *Remington's Pharmaceutical Sciences* (Gennaro, A., ed.), Mack Pub., 1990. Formulations of the therapeutic agents of the invention may include, for example, polyalkylene glycols such as polyethylene glycol, oils of vegetable origin, hydrogenated naphthalenes, and the like. Formulations for direct administration, in particular, may include glycerol and other compositions of high viscosity to help maintain the agent at the desired locus. Biocompatible, preferably bioresorbable, polymers, including, for example, hyaluronic acid, collagen, tricalcium phosphate, polybutyrate, lactide, and glycolide polymers and lactide/glycolide copolymers, may be useful excipients to control the release of the agent in vivo. Other potentially useful parenteral delivery systems for these agents include ethylene-vinyl acetate copolymer particles, osmotic pumps, implantable infusion systems, and liposomes. Formulations for inhalation administration contain as excipients, for example, lactose, or may be aqueous solutions containing, for example, polyoxyethylene-9-lauryl ether, glycocholate and deoxycholate, or oily solutions for administration in the form of nasal drops, or as a gel to be applied intranasally. Formulations for parenteral administration may also include glycocholate for buccal administration, methoxysalicylate for rectal administration, or cutric acid for vaginal administration. Suppositories for rectal administration also may be prepared by mixing the morphogen, inducer or agonist with a non-irritating excipient such as cocoa butter or other compositions which are solid at room temperature and liquid at body temperatures.

Formulations for topical administration to the skin surface may be prepared by dispersing the morphogen, inducer or agonist with a dermatologically acceptable carrier such as a lotion, cream, ointment or soap. Particularly useful are carriers capable of forming a film or layer over the skin to localize application and inhibit removal. For topical administration to internal tissue surfaces, the agent may be dispersed in a liquid tissue adhesive or other substance known to enhance adsorption to a tissue surface. For example, hydroxypropylcellulose or fibrinogen/thrombin solutions may be used to advantage. Alternatively, tissue-coating solutions, such as pectin-containing formulations may be used.

Alternatively, the agents described herein may be administered orally. Oral administration of proteins as therapeutics generally is not practiced as most proteins are readily degraded by digestive enzymes and acids in the mammalian digestive system before they can be absorbed into the bloodstream. However, the morphogens described herein typically are acid stable and protease-resistant (see, for example, U.S. Pat. No. 4,968,590). In addition, at least one morphogen, OP-1, has been identified in mammary gland extract colostrum and 57-day milk. Moreover, the OP-1 purified from mammary gland extract is morphogenically active and also is detected in the bloodstream. Finally, soluble form morphogen, e.g., mature morphogen associated with the pro domain, is morphogenically active. These findings, as well as those disclosed in the examples below, indicate that oral and parenteral administration are viable means for administering morphogens to an individual. In addition, while the mature forms of certain morphogens described herein typically are sparingly soluble, the morphogen form found in milk (and mammary gland extract and colostrum) is readily soluble, probably by association of the mature, morphogenically active form with part or all of the pro domain of the intact sequence and/or by association with one or more milk components. Accordingly, the compounds provided herein also may be associated with molecules capable of enhancing their solubility in vitro or in vivo.

The compounds provided herein also may be associated with molecules capable of targeting the morphogen, inducer or agonist to the desired tissue. For example, an antibody, antibody fragment, or other binding protein that interacts specifically with a surface molecule on cells of the desired tissue, may be used. Useful targeting molecules may be designed, for example, using the single chain binding site technology disclosed, for example, in U.S. Pat. No. 5,091,513.

As will be appreciated by one of ordinary skill in the art, the formulated compositions contain therapeutically effective amounts of the morphogen, morphogen inducers or agonists of morphogen receptors. That is, they contain amounts which provide appropriate concentrations of the agent to the renal tissues for a time sufficient to stimulate renal morphogenesis and/or to prevent, inhibit or delay compensatory renal hypertrophy and/or further significant decline in renal function. As will be appreciated by those skilled in the art, the concentration of the compounds described in a therapeutic composition of the present invention will vary depending upon a number of factors, including the biological efficacy of the selected agent, the chemical characteristics (e.g., hydrophobicity) of the compounds employed, the formulation of the compound excipients, the administration route, and the treatment envisioned, including whether the active ingredient will be administered directly into a kidney or renal capsule, or whether it will be administered systemically. The preferred dosage to be administered also is likely to depend on such variables such as the condition of the renal tissues, extent of renal function loss, and the overall health status of the particular subject. As a general matter, daily or weekly dosages of 0.00001–1000 mg of a morphogen are sufficient with 0.0001–100 mg being preferable and 0.001 to 10 mg being even more preferable. Alternatively, a daily or weekly dosage of 0.01–1000 $\mu$g/kg body weight, more preferably 0.1–100 $\mu$g/kg body weight, may be advantageously employed. Dosages are preferably administered continuously, but daily, multi-weekly, weekly or monthly dosages may also be employed. For subjects which would otherwise require bi-weekly or tri-weekly hemodialysis sessions, bi-weekly or tri-weekly intravenous or intraperitoneal infusions are not considered unduly inconvenient. In addition, in order to facilitate frequent infusions, implantation of a semi-permanent stent (e.g., intravenous, intraperitoneal or intracapsular) may be advisable. It should be noted that no obvious morphogen induced pathological lesions arise when mature morphogen (e.g., OP-1, 20 mg) is administered daily to normal growing rats for 21 consecutive days. Moreover, 10 mg systemic injections of morphogen (e.g., OP-1) injected daily for 10 days into normal newborn mice does not produce any gross abnormalities.

The morphogens, inducers or agonists of the invention may, of course, be administered alone or in combination with other molecules known to be beneficial in the treatment of the conditions described herein.

Finally, as noted above, in another series of embodiments renal cells may be implanted into the kidney of a subject at risk of chronic renal failure, or at risk of needing renal replacement therapy, in order to serve as a source of morphogen and/or to provide a source of additional functional renal tissue. These cells may be renal mesenchymal progenitor cells, or renal mesenchymal progenitor cells which have been induced to undergo metanephric differentiation. The cells may be derived from a donor (e.g., a tissue-type matched donor, sibling, identical twin), may be derived from a tissue culture (e.g., undifferentiated renal mesenchyme culture, fetal renal tissue culture), or may be explanted from the subject and then be re-implanted after proliferation and/or differentiation. Preferably, the cells are induced to undergo metanephric differentiation by treatment with a morphogen (e.g., OP-1) either before or after implantation. Thus, for example, renal mesenchymal progenitor cells may be explanted from a subject, allowed or caused to proliferate in vitro, be induced to undergo metanephric differentiation by morphogen treatment, and be re-implanted where they may provide a source of morphogen and/or differentiate further into functional renal tissue.

Practice of the invention, including additional preferred aspects and embodiments thereof, will be still more fully understood from the following examples, which are presented herein for illustration only and should not be construed as limiting the invention in any way.

EXAMPLES

Rat Remnant Kidney Model

A rat partial (5/6) nephrectomy or rat remnant kidney model (RRKM) model was employed essentially as described (Vukicevic, et al. (1987) *J. Bone Mineral Res.* 2:533). Male rats (2–3 months old, weighing about 150–200 g) were subjected to unilateral nephrectomy (either left or right kidney). After approximately one week, 2/3 of the remaining kidney was surgically removed. Immediately following surgery, plasma creatinine and BUN levels rise dramatically due to the loss of renal mass and function. Over the next several weeks of this "acute" failure phase, plasma creatinine and BUN levels of surviving animals decline somewhat toward normal values but remain elevated. Renal function then appears to remain relatively constant or stable for a period of variable duration. After this point, the animals enter a period of chronic renal failure in which there is an essentially linear decline in renal function ending in death.

As surgical controls, additional rats were subjected to a "sham" operation in which the kidneys were decapsulated but no renal tissue was removed.

Intervention Model for Chronic Renal Failure

In this model, both nephrectomized and sham-operated rats were maintained for approximately 5–6 months after surgery. At this point, surviving nephrectomized animals were past the stable phase and had entered chronic renal failure.

Rats were divided into 8 groups with 12 rats in each group. Two groups of nephrectomized rats were used as controls (Nx controls), with one of those groups receiving no treatment at all, while the other received injections of only the vehicle buffer. In addition, two groups of sham-operated rats were used as controls (sham controls), with one group receiving only the vehicle buffer, while the other received soluble OP-1 (sOP-1) at 10 $\mu$g/kg body weight. Four experimental groups of nephrectomized rats were employed, receiving sOP-1 at 1, 3, 10 or 50 $\mu$g/kg body weight by intraperitoneal injection (OP-1 Nx animals). OP-1 treated and vehicle-only rats received three injections per week for 4–8 weeks. Total injection volume was 300 $\mu$l. No statistically significant differences were observed between the two Nx control groups or between the two sham control groups.

Figure 2:
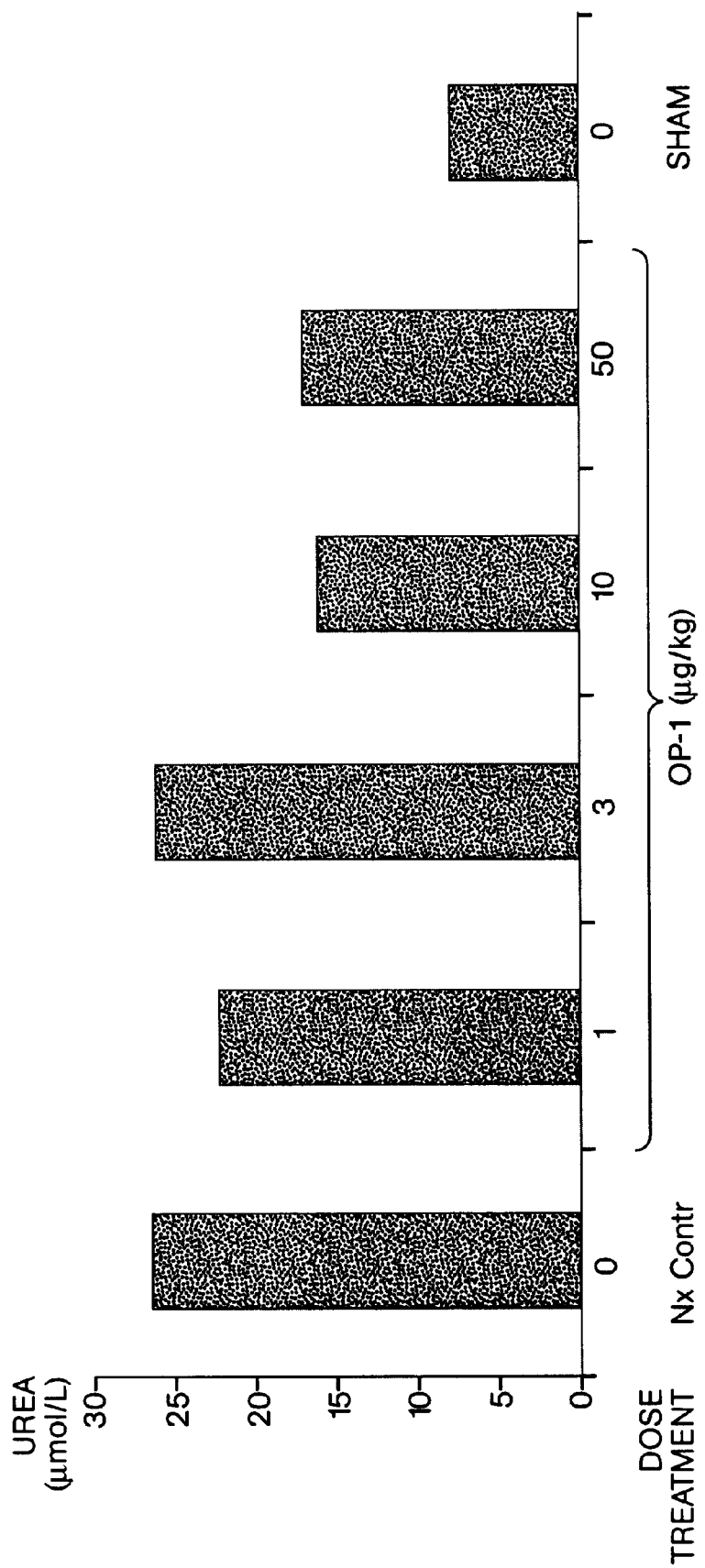
FIG. 2. This figure is a bar graph showing average serum urea levels for groups of sham-operated ("SHAM") or partially nephrectomized ("Nx Contr" and "OP-1") rats. 5–6 months post-surgery, rats received injections of vehicle only ("Nx control" and "SHAM") or 1, 3, 10 or 50 µg/kg body weight of soluble OP-1 ("OP-1") three times a week for 4–8 weeks.

Compared to the sham group receiving only vehicle, the Nx control receiving only vehicle demonstrated significantly ($p<0.01$) elevated serum creatinine (FIG. 1) at the end of the study, indicating a significant loss of renal function. Although nephrectomized rats treated with either 1 or 3 $\mu$g/kg body weight sOP-1 did not show significantly reduced serum creatinine when compared to the Nx control, nephrectomized rats treated with sOP-1 at doses of 10 or 50 $\mu$g/kg body weight showed significant ($p<0.05$) reductions in creatinine values (FIG. 1). Similar results were observed for serum urea levels: Although nephrectomized rats treated with either 1 or 3 $\mu$g/kg body weight sOP-1 did not show significantly reduced serum urea when compared to the Nx control, nephrectomized rats treated with sOP-1 at doses of 10 or 50 $\mu$g/kg body weight showed significant ($p<0.01$) reductions in serum urea values (FIG. 2). All nephrectomized rats showed significantly ($p<0.01$) higher serum urea when compared to the sham-operated rats (FIG. 2).

Figure 3A:
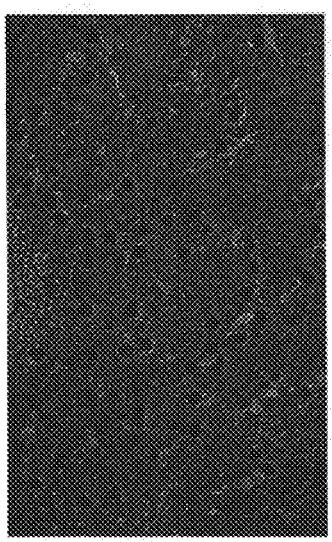
FIG. 3. Panels A-C of this figure are micrographs of renal tissue from rats at 10×magnification. (A) Tissue from sham-operated rat. (B) Tissue from rat in chronic renal failure after 5/6 nephrectomy (Nx control). (C) Tissue from rat treated with OP-1 after 5/6 nephrectomy.
Figure 3B:
Figure 3C:
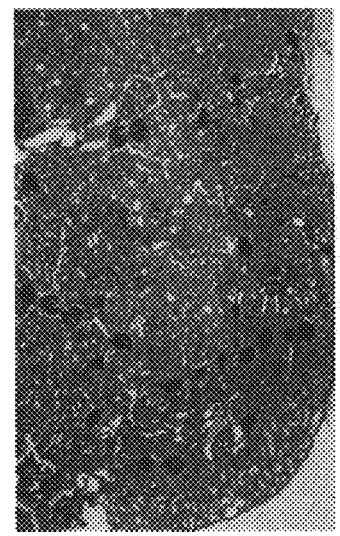
Figure 4A:
FIG. 4. Panels A-C of this figure are micrographs of renal tissue from rats at 40×magnification. (A) Tissue from sham-operated rat. (B) Tissue from rat in chronic renal failure after 5/6 nephrectomy (Nx control). (C) Tissue from rat treated with OP-1 after 5/6 nephrectomy.
Figure 4B:
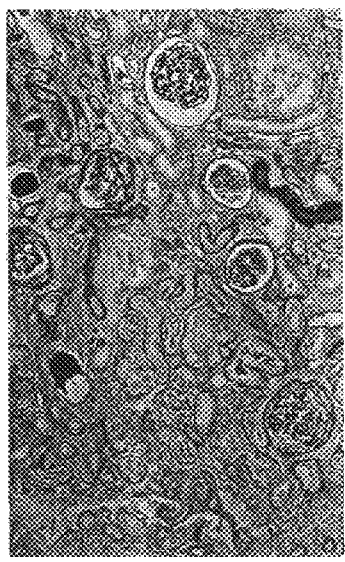
Figure 4C:
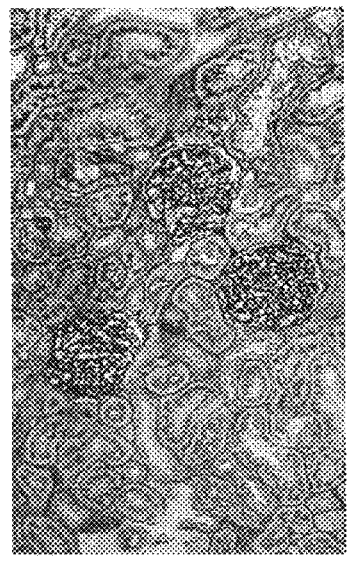

Histological observations indicate that, in contrast to the vehicle treated Nx control group, OP-1 treated nephrectomized rats exhibit relatively normal glomerular histology. FIG. 3, for example, shows typical renal samples from (A) normal rat kidney, (B) untreated Nx control animals, and (C) OP-1 treated nephrectomized rats under low magnification (10×). FIG. 4 shows similar samples under higher magnification (40×). Histomorphometric analysis indicates that OP-1 Nx rats showed reduced incidence of glomerular sclerosis and loop collapse, relatively scattered sclerosis and microaneurysms, and more viable glomeruli compared to Nx control rats (Table 2).

None of the rats died in any group during this study.

Prophylactic Model for Chronic Renal Failure

Rats were subjected to partial nephrectomies or sham-operated as described above. In this model, in order to test the ability of morphogens to prevent, inhibit or delay the initiation of chronic renal failure, the rats were allowed to recover for approximately two weeks after surgery before initiation of OP-1 therapy. At this point, surviving animals were past the acute renal failure phase and had not yet entered chronic renal failure.

Rats were divided into two groups of 15–20 rats. One group received only vehicle buffer (Nx control) whereas the other received OP-1 treatment at 10 $\mu$g/kg body weight given intraperitoneally three times per week. Administration of OP-1 or vehicle continued for a period of approximately 8–9 weeks.

Figure 5:
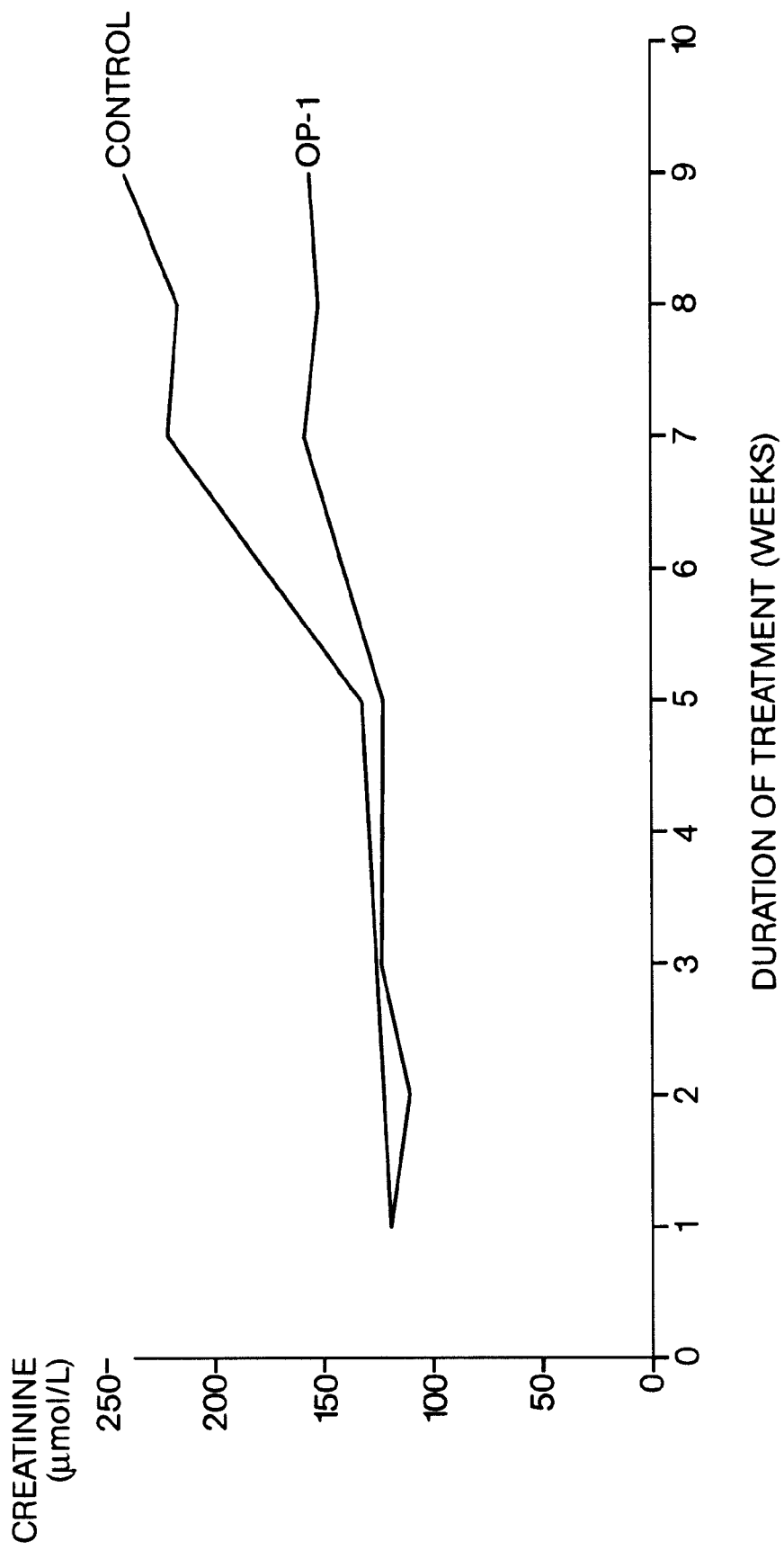
FIG. 5. This figure is a line graph showing average serum creatinine levels over 9 weeks for groups of partially nephrectomized rats. 2–3 weeks post-surgery, rats received injections of vehicle only ("Control") or 10 μg/kg body weight of soluble OP-1 ("OP-1") 3 times per week.

During weeks 1–5 of treatment, both groups showed elevated serum creatinine (>100 $\mu$mol/L) relative to sham-operated controls (35±7 $\mu$mol/L). At about 5 weeks, both groups began to show a rise in serum creatinine suggesting the onset of progressive or chronic renal failure. The rise in serum creatinine was, however, markedly less rapid in the OP-1 treated group and was significantly lower than in the Nx controls (FIG. 5: $p<0.02$ at weeks 6 and 8; $p<0.01$ at weeks 7 and 9). Similar results were observed in serum BUN values as well.

Figure 6:
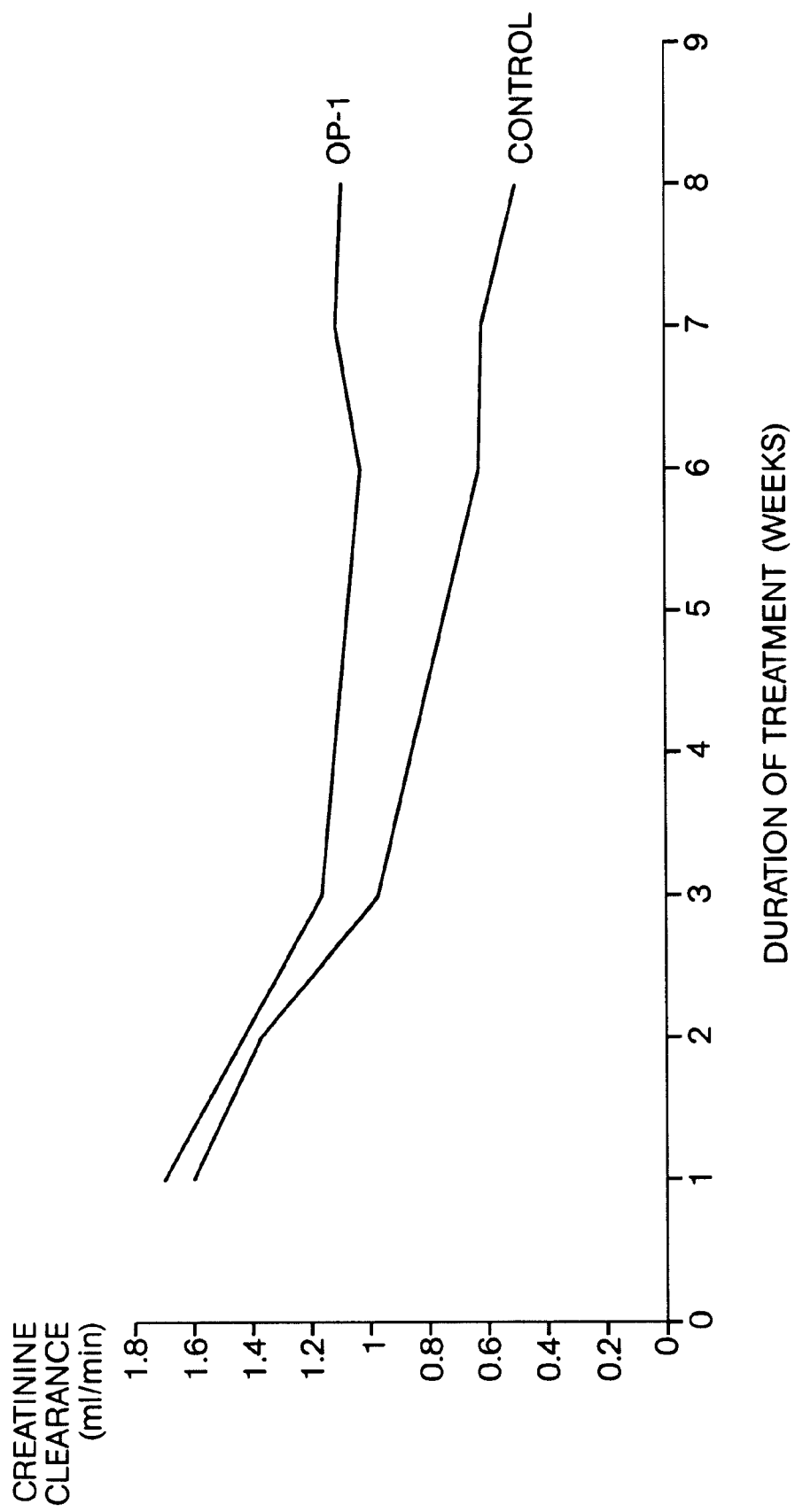
FIG. 6. This figure is a line graph showing average creatinine clearance rates as a measure of GFR over 8 weeks for groups of partially nephrectomized rats. 2–3 weeks post-surgery, rats received injections of vehicle only ("Control") or 10 μg/kg body weight of soluble OP-1 ("OP-1") 3 times per week.

More important, measurements of GFR, based on serum and urine creatinine values, showed a highly significant decrease in both groups of nephrectomized rats (<1.8 ml/min) relative to sham-operated controls (4.7±1.1 ml/min). The GFR in both groups continued to decline during weeks 1–3 of treatment. At approximately three weeks, however, GFR in the OP-1 treated group stabilized whereas the decline in renal function continued in the Nx controls. By week 5, the difference in GFR values between OP-1 treated and Nx control rats had become statistically significant (p<0.02). This difference in GFR continued to increase over time (p<0.01 at week 6; p<0.001 at weeks 7 and 8), as the Nx controls continued to decline but the OP-1 treated rats remained stable (FIG. 6). By the end of 9 weeks, 40% of the Nx control rats were dead whereas none of the OP-1 treated rats had died.

Histological evaluation of tissue sections confirmed that OP-1 treated rats showed greater preservation or maintenance of glomeruli, as well as proximal and distal tubule structures. There were also signs in the OP-1 treated rats of nephrogenic mesenchymal condensations and the appearance of developmental nephrogenic structures. Table 2 reports results of several standard quantitative (e.g., PAS-staining of extracellular matrix) and semi-quantitative (e.g., visual ranking) histomorphometric measures obtained for tissue slices from Nx control and OP-1 treated Nx rats. These results indicate that OP-1 treatment of nephrectomized rates resulted in overall improvement (or reduced degeneration) of kidney tissue morphology, increased mesangial or perivascular thickening, decreased glomerular sclerosis and loop collapse, decreased presence of "scattered" sclerosis and microaneurysms, and an increase in viable glomeruli.

dimers" wherein one subunit of the dimer is an uncleaved pro form of the protein, and the other subunit comprises the mature form of the protein, including truncated forms thereof, preferably noncovalently associated with a cleaved pro domain peptide.

As described above and in published application WO94/03600, the teachings of which are incorporated herein by reference, useful pro domains include the full length pro regions, as well as various truncated forms hereof, particularly truncated forms cleaved at proteolytic Arg-Xaa-Xaa-Arg cleavage sites within the pro domain polypeptide. For example, in OP-1, possible pro sequences include sequences defined by residues 30–292 (full length form); 48–292; and 158–292. Soluble OP-1 complex stability is best enhanced when the pro region comprises the full length form rather than a truncated form, such as the residues 48–292 truncated form, in that residues 30–47 show sequence homology to the N-terminal portions of other morphogens, and currently are believed to have particular utility in enhancing complex stability for all morphogens. Accordingly, currently preferred pro domains include peptides comprising at least the N-terminal fragment, e.g., amino acid residues 30–47 of a naturally occurring morphogen pro domain, or a biosynthetic variant thereof that retains the solubility and/or stability enhancing properties of the naturally-occurring peptide.

As will be appreciated by those having ordinary skill in the art, useful sequences encoding the pro region can be obtained from genetic sequences encoding known morphogens. Alternatively, chimeric pro regions can be constructed from the sequences of one or more known morphogens. Still another option is to create a synthetic sequence variant of one or more known pro region sequences.

In another preferred aspect, useful pro region peptides include polypeptide chains comprising an amino acid

TABLE 2

| Group | Normal Histology | Mesangial Thickening | Glomerular Sclerosis & Loop Collapse | Scattered Sclerosis & Microaneurysms | Absence of Viable Glomeruli |
|---|---|---|---|---|---|
| Control (N = 15) | 2.58 ± 0.22 | 27.3 ± 2.4 | 26.5 ± 3.5 | 34.7 ± 4.2 | 8.9 ± 0.7 |
| OP-1 (N = 20) | 11.41 ± 1.1 | 58.6 ± 3.2 | 14.7 ± 1.3 | 11.8 ± 1.1 | 2.5 ± 0.2 |
| Significance | p <0.01 | p < 0.01 | p < 0.02 | p < 0.01 | p < 0.01 |

Preparation of Soluble Morphogen Complexes

A currently preferred form of the morphogen useful herein, having improved solubility in aqueous solutions, is a dimeric morphogenic protein comprising at least the C-terminal seven cysteine domain characteristic of the morphogen family, complexed with a peptide comprising a pro region of a member of the morphogen family, or a solubility-enhancing fragment thereof, or an allelic, species or other sequence variant thereof. Preferably, the dimeric morphogenic protein is complexed with two pro region peptides. Also, the dimeric morphogenic protein preferably is noncovalently complexed with the pro region peptides. The pro region peptides preferably comprise at least the N-terminal eighteen amino acids that define the pro domain of a given naturally occurring morphogen, or an allelic or phylogenetic counterpart variant thereof. In other preferred embodiments, peptides defining substantially the full length pro domain are used.

Other soluble forms of morphogens include dimers of the uncleaved pro forms of these proteins, as well as "hemisequence encoded by a nucleic acid that hybridizes under stringent conditions with a DNA or RNA sequence encoding at least the N-terminal eighteen amino acids of the pro region sequence for OP-1 or OP-2, e.g., nucleotides 136–192 and 152–211 of SEQ ID NOs: 15 and 19, respectively.

A. Isolation from Conditioned Media or Body Fluid

Morphogens are expressed from mammalian cells as soluble complexes. Typically, however the complex is disassociated during purification, generally by exposure to denaturants often added to the purification solutions, such as detergents, alcohols, organic solvents, chaotropic agents and compounds added to reduce the pH of the solution. Provided below is a currently preferred protocol for purifying the soluble proteins from conditioned media (or, optionally, a body fluid such as serum, cerebrospinal or peritoneal fluid), under non-denaturing conditions. The method is rapid, reproducible and yields isolated soluble morphogen complexes in substantially pure form.

Soluble morphogen complexes can be isolated from conditioned media using a simple, three step chromatographic protocol performed in the absence of denaturants. The protocol involves running the media (or body fluid) over an affinity column, followed by ion exchange and gel filtration chromatographies. The affinity column described below is a Zn-IMAC column. The present protocol has general applicability to the purification of a variety of morphogens, all of which are anticipated to be isolatable using only minor modifications of the protocol described below. An alternative protocol also envisioned to have utility includes an immunoaffinity column, created using standard procedures and, for example, using antibody specific for a given morphogen pro domain (complexed, for example, to a protein A-conjugated Sepharose column). Protocols for developing immunoaffinity columns are well described in the art (see, for example, *Guide to Protein Purification*, M. Deutscher, ed., Academic Press, San Diego, 1990, particularly sections VII and XI thereof).

In this study, OP-1 was expressed in mammalian (CHO, Chinese hamster ovary) cells as described in the art (see, for example, international application US90/05903 (WO91/05802). The CHO cell conditioned media containing 0.5% FBS was initially purified using Immobilized Metal-Ion Affinity Chromatography (IMAC). The soluble OP-1 complex from conditioned media binds very selectively to the Zn-IMAC resin and a high concentration of imidazole (50 mM imidazole, pH 8.0) is required for the effective elution of the bound complex. The Zn-IMAC step separates the soluble OP-1 from the bulk of the contaminating serum proteins that elute in the flowthrough and 35 mM imidazole wash fractions. The Zn-IMAC purified soluble OP-1 is next applied to an S-Sepharose cation-exchange column equilibrated in 20 mM NaPO$_4$ (pH 7.0) with 50 mM NaCI. This S-Sepharose step serves to further purify and concentrate the soluble OP-1 complex in preparation for the following gel filtration step. The protein was applied to a Sephacryl S-200HR column equilibrated in TBS. Using substantially the same protocol, soluble morphogens also can be isolated from one or more body fluids, including serum, cerebrospinal fluid or peritoneal fluid.

IMAC was performed using Chelating-Sepharose (Pharmacia) that had been charged with three column volumes of 0.2 M ZnSO$_4$. The conditioned media was titrated to pH 7.0 and applied directly to the Zn-IMAC resin equilibrated in 20 mM HEPES (pH 7.0) with 500 mM NaCl. The Zn-IMAC resin was loaded with 80 mL of starting conditioned media per mL of resin. After loading, the column was washed with equilibration buffer and most of the contaminating proteins were eluted with 35 mM imidazole (pH 7.0) in equilibration buffer. The soluble OP-1 complex then is eluted with 50 mM imidazole (pH 8.0) in 20 mM HEPES and 500 mM NaCl.

The 50 mM imidazole eluate containing the soluble OP-1 complex was diluted with nine volumes of 20 mM NaPO$_4$ (pH 7.0) and applied to an S-Sepharose (Pharmacia) column equilibrated in 20 mM NaPO$_4$ (pH 7.0) with 50 mM NaCl. The S-Sepharose resin was loaded with an equivalent of 800 mL of starting conditioned media per mL of resin. After loading the S-Sepharose column was washed with equilibration buffer and eluted with 100 mM NaCl followed by 300 mM and 500 mM NaCl in 20 mM NaPO4 (pH 7.0). The 300 mM NaCl pool was further purified using gel filtration chromatography. Fifty mls of the 300 mM NaCl eluate was applied to a 5.0×90 cm Sephacryl S-200HR (Pharmacia) equilibrated in Tris buffered saline (TBS), 50 mM Tris, 150 mM NaCl (pH 7.4). The column was eluted at a flow rate of 5 mL/minute collecting 10 mL fractions. The apparent molecular of the soluble OP-1 was determined by comparison to protein molecular weight standards (alcohol dehydrogenase (ADH, 150 kDa), bovine serum albumin (BSA, 68 kDa), carbonic anhydrase (CA, 30 kDa) and cytochrome C (cytC, 12.5 kDa). The purity of the S-200 column fractions was determined by separation on standard 15% polyacrylamide SDS gels stained with coomassie blue. The identity of the mature OP-1 and the pro-domain was determined by N-terminal sequence analysis after separation of the mature OP-1 from the pro-domain using standard reverse phase C18 HPLC.

The soluble OP-1 complex elutes with an apparent molecular weight of 1 10 kDa. This agrees well with the predicted composition of the soluble OP-1 complex with one mature OP-1 dimer (35–36 kDa) associated with two pro-domains (39 kDa each). Purity of the final complex can be verified by running the appropriate fraction in a reduced 15% polyacrylamide gel.

The complex components can be verified by running the complex-containing fraction from the S-200 or S-200HR columns over a reverse phase C18 HPLC column and eluting in an acetonitrile gradient (in 0.1% TFA), using standard procedures. The complex is dissociated by this step, and the pro domain and mature species elute as separate species. These separate species then can be subjected to N-terminal sequencing using standard procedures (see, for example, *Guide to Protein Purification*, M. Deutscher, ed., Academic Press, San Diego, 1990, particularly pp. 602–613), and the identity of the isolated 36 kDa, 39 kDa proteins confirmed as mature morphogen and isolated, cleaved pro domain, respectively. N-terminal sequencing of the isolated pro domain from mammalian cell produced OP-1 revealed 2 forms of the pro region, the intact form (beginning at residue 30 of SEQ ID NO: 16) and a truncated form, (beginning at residue 48 of SEQ ID NO: 16.) N-terminal sequencing of the polypeptide subunit of the isolated mature species reveals a range of N-termini for the mature sequence, beginning at residues 293, 300, 313, 315, 316, and 318, of SEQ ID NO: 16, all of which are active as demonstrated by the standard bone morphogenesis assay set forth in published application WO92/15323 as incorporated herein by reference.

B. In Vitro Soluble Morphogen Complex Formation

As an alternative to purifying soluble complexes from culture media or a body fluid, soluble complexes can be formulated from purified pro domains and mature dimeric species. Successful complex formation apparently requires association of the components under denaturing conditions sufficient to relax the folded structure of these molecules, without affecting disulfide bonds. Preferably, the denaturing conditions mimic the environment of an intracellular vesicle sufficiently such that the cleaved pro domain has an opportunity to associate with the mature dimeric species under relaxed folding conditions. The concentration of denaturant in the solution then is decreased in a controlled, preferably step-wise manner, so as to allow proper refolding of the dimer and pro regions while maintaining the association of the pro domain with the dimer. Useful denaturants include 4–6M urea or guanidine hydrochloride (GuHCl), in buffered solutions of pH 4–10, preferably pH 6–8. The soluble complex then is formed by controlled dialysis or dilution into a solution having a final denaturant concentration of less than 0.1–2M urea or GuHCl, preferably 1–2 M urea of GuHCl, which then preferably can be diluted into a physiological buffer. Protein purification/renaturing procedures and considerations are well described in the art, and details for developing a suitable renaturing protocol readily can be determined by one having ordinary skill in the art. One useful text on the subject is *Guide to Protein Purification*, M. Deutscher, ed., Academic Press, San Diego, 1990, particularly section V. Complex formation also may be aided by addition of one or more chaperone proteins.

C. Stability of Soluble Morphogen Complexes

The stability of the highly purified soluble morphogen complex in a physiological buffer, e.g., Tris-buffered saline (TBS) and phosphate-buffered saline (PBS), can be enhanced by any of a number of means. Currently preferred is by means of a pro region that comprises at least the first 18 amino acids of the pro sequence (e.g., residues 30–47 of SEQ ID NO: 16 for OP-1), and preferably is the full length pro region. Residues 30–47 show sequence homology to the N-terminal portion of other morphogens and are believed to have particular utility in enhancing complex stability for all morphogens. Other useful means for enhancing the stability of soluble morphogen complexes include three classes of additives. These additives include basic amino acids (e.g., L-arginine, lysine and betaine); nonionic detergents (e.g., Tween 80 or Nonldet P-120); and carrier proteins (e.g., serum albumin and casein). Useful concentrations of these additives include 1–100 mM, preferably 10–70 mM, including 50 mM, basic amino acid;, 0.01–1.0%, preferably 0.05–0.2%, including 0.1% (v/v) nonionic detergent;, and 0.01–1.0%, preferably 0.05–0.2%, including 0.1% (w/v) carrier protein.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are intended to be embraced therein.

What is claimed is:

1. A method of treatment for a mammal at risk of chronic renal failure comprising:

administering to said mammal a therapeutically effective amount of a morphogen, wherein said morphogen comprises a dimeric protein having an amino acid sequence selected from the group consisting of:
 (i) a sequence having at least 70% amino acid sequence homology with the C-terminal seven-cysteine skeleton of human OP-1, amino acids 38–139 of SEQ ID NO:4;
 (ii) a sequence having at least a 60% amino acid sequence identity with the C-terminal six-cysteine skeleton of human OP-1, amino acid residues 43–139 of SEQ ID NO:4;
 (iii) an amino acid sequence variant defined by Generic Sequence 7, SEQ ID NO:1;
 (iv) an amino acid sequence variant defined by Generic Sequence 8, SEQ ID NO:2;
 (v) an amino acid substitution variant encoded by a nucleic acid sequence which possesses the ability to hybridize under stringent conditions to a nucleic acid sequence complementary to a nucleic acid sequence encoding the C-terminal seven-cysteine skeleton of OP-1, nucleotides 1036–1341 of SEQ ID NO:15; and
 (vi) an amino acid substitution variant encoded by a nucleic acid sequence which possesses the ability to hybridize under stringent conditions to a nucleic acid sequence complementary to a nucleic acid sequence encoding the C-terminal seven-cysteine skeleton of OP-2, nucleotides 1390–1695 of SEQ ID NO:19, wherein said morphogen induces endochondral bone formation in an in vivo assay.

2. A method as in claim 1 wherein said mammal is afflicted with a condition selected from the group consisting of chronic renal failure, end-stage renal disease, chronic diabetic nephropathy, diabetic glomerulopathy, diabetic renal hypertrophy, hypertensive nephrosclerosis, hypertensive glomerulosclerosis, chronic glomerulonephritis, hereditary nephritis, and renal dysplasia.

3. A method as in claim 1 wherein examination of a renal biopsy of said mammal indicates that said mammal is afflicted with a condition selected from the group consisting of glomerular hypertrophy, tubular hypertrophy, glomerulosclerosis, and tubulointerstitial sclerosis.

4. A method as in claim 1 wherein examination of said mammal indicates renal fibrosis.

5. A method as in claim 4 wherein said examination is an ultrasound, MRI or CAT scan of said mammal.

6. A method as in claim 1 wherein said mammal possesses a number of functional nephron units which is less than about 50% of a number of functional nephron units present in a mammal having intact healthy kidneys.

7. A method as in claim 1 wherein said mammal is a kidney transplant recipient.

8. A method as in claim 1 wherein said mammal possesses only one kidney.

9. A method as in claim 1 wherein examination of a urinary sediment of said mammal indicates a presence of broad casts.

10. A method as in claim 1 wherein said mammal has a GFR which is chronically less than about 50% of a $GFR_{exp}$ for said mammal.

11. A method as in claim 1 wherein said mammal is a human male weighing at least about 50 kg and has a GFR which is chronically less than about 50 ml/min.

12. A method as in claim 1 wherein said mammal is a human female weighing at least about 40 kg and has a GFR which is chronically less than about 40 ml/min.

13. A method as in claim 1 wherein said treatment reduces serum creatinine levels in said mammal by at least about 5% over 3 months.

14. A method as in claim 1 wherein prior to said treatment said mammal presented a chronic decline in a clinical indicator of renal function; and after at least about 3 months of said treatment, said indicator stabilizes.

15. A method as in claim 1 wherein said administration is oral.

16. A method as in claim 1 wherein said administration is parenteral.

17. A method as in claim 1 wherein said administration is at least once a week for a period of at least about one month.

18. A method as in claim 1 wherein said morphogen is selected from the group consisting of a pro form of a morphogen, a soluble form of a morphogen, and a mature morphogen.

19. A method as in claim 1 wherein said morphogen is selected from the group consisting of human osteogenic proteins and human bone morphogenic proteins.

20. The method of claim 1, wherein said morphogen is selected from the group comprising: OP-1, OP-2, OP-3, CBMP2A, CBMP2B, dpp, Vgl, Vgr-1, GDF-1, 60A, BMP-3, BMP-5, and BMP-6.

21. The method of claim 22, wherein said morphogen is OP-1.

22. A method of treatment to delay the need for, or reduce the frequency of, chronic dialysis treatments comprising:

administering to said mammal a therapeutically effective amount of a morphogen, wherein said morphogen comprises a dimeric protein having an amino acid sequence selected from the group consisting of:
- (i) a sequence having at least 70% amino acid sequence homology with the . C-terminal seven-cysteine skeleton of human OP-1, amino acids 38–139 of SEQ ID NO:4;
- (ii) a sequence having at least a 60% amino acid sequence identity with the C-terminal six-cysteine skeleton of human OP-1, amino acid residues 43–139 of SEQ ID NO:4;
- (iii) an amino acid sequence variant defined by Generic Sequence 7, SEQ ID NO:1;
- (iv) an amino acid sequence variant defined by Generic Sequence 8, SEQ ID NO:2;
- (v) an amino acid substitution variant encoded by a nucleic acid sequence which possesses the ability to hybridize under stringent conditions to a nucleic acid sequence complementary to a nucleic acid sequence encoding the C-terminal seven-cysteine skeleton of OP-1, nucleotides 1036–1341 of SEQ ID NO:15; and
- (vi) an amino acid substitution variant encoded by a nucleic acid sequence which possesses the ability to hybridize under stringent conditions to a nucleic acid sequence complementary to a nucleic acid sequence encoding the C-terminal seven-cysteine skeleton of OP-2, nucleotides 1390–1695 of SEQ ID NO: 19, wherein said morphogen induces endochondral bone formation in an in vivo assay.

23. The method of claim 22, wherein said morphogen is selected from the group comprising: OP-1, OP-2, OP-3, CBMP2A, CBMP2B, dpp, Vgl, Vgr-1, GDF-1, 60A, BMP-3, BMP-5, and BMP-6.

24. The method of claim 22, wherein said morphogen is OP-1.

* * * * *

```
                         SEQUENCE LISTING (1) GENERAL INFORMATION:

(iii) NUMBER OF SEQUENCES: 31

(2) INFORMATION FOR SEQ ID NO:1:

(i) SEQUENCE CHARACTERISTICS:
        (A) LENGTH: 97 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..97
        (D) OTHER INFORMATION: /label= Generic-Seq-7
            /note= "wherein each Xaa is independently selected
            from a group of one or more specified amino acids
            as defined in the specification."

(xi) SEQUENCE DESCRIPTION: SEQ ID NO:1:

Leu Xaa Xaa Xaa Phe Xaa Xaa Xaa Gly Trp Xaa Xaa Xaa Xaa Xaa Xaa
1               5                   10                  15

Pro Xaa Xaa Xaa Xaa Ala Xaa Tyr Cys Xaa Gly Xaa Cys Xaa Xaa Pro
            20                  25                  30

Xaa Xaa Xaa Xaa Xaa Xaa Xaa Asn His Ala Xaa Xaa Xaa Xaa Xaa
        35                  40                  45

Xaa Xaa Xaa Xaa Xaa Xaa Xaa Xaa Xaa Xaa Xaa Cys Cys Xaa Pro
    50                  55                  60

Xaa Xaa Xaa Xaa Xaa Xaa Xaa Xaa Leu Xaa Xaa Xaa Xaa Xaa Xaa
65                  70                  75                  80

Val Xaa Leu Xaa Xaa Xaa Xaa Xaa Met Xaa Val Xaa Xaa Cys Xaa Cys
                85                  90                  95

Xaa (2) INFORMATION FOR SEQ ID NO:2:

(i) SEQUENCE CHARACTERISTICS:
        (A) LENGTH: 102 amino acids
        (B) TYPE: amino acid
```

-continued

```
        (C) STRANDEDNESS: single
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= Generic-Seq-8
             /note= "wherin each Xaa is independently selected
             from a group of one or more specified amino acids
             as defined in the specification."

(xi) SEQUENCE DESCRIPTION: SEQ ID NO:2:

Cys Xaa Xaa Xaa Xaa Leu Xaa Xaa Xaa Phe Xaa Xaa Xaa Gly Trp Xaa
1               5                   10                  15

Xaa Xaa Xaa Xaa Xaa Pro Xaa Xaa Xaa Xaa Ala Xaa Tyr Cys Xaa Gly
            20                  25                  30

Xaa Cys Xaa Xaa Pro Xaa Xaa Xaa Xaa Xaa Xaa Xaa Xaa Asn His Ala
        35                  40                  45

Xaa Xaa Xaa Xaa Xaa Xaa Xaa Xaa Xaa Xaa Xaa Xaa Xaa Xaa Xaa Xaa
    50                  55                  60

Xaa Cys Cys Xaa Pro Xaa Xaa Xaa Xaa Xaa Xaa Xaa Xaa Leu Xaa Xaa
65                  70                  75                  80

Xaa Xaa Xaa Xaa Xaa Val Xaa Leu Xaa Xaa Xaa Xaa Xaa Met Xaa Val
                85                  90                  95

Xaa Xaa Cys Xaa Cys Xaa
            100

(2) INFORMATION FOR SEQ ID NO:3:

(i) SEQUENCE CHARACTERISTICS:
        (A) LENGTH: 102 amino acids
        (B) TYPE: amino acid
        (D) TOPOLOGY: linear (ii) MOLECULE TYPE: protein (ix) FEATURE:
        (A) NAME/KEY: Protein
        (B) LOCATION: 1..102
        (D) OTHER INFORMATION: /label= OPX
             /note= "WHEREIN EACH XAA IS INDEPENDENTLY SELECTED
             FROM A GROUP OF ONE OR MORE SPECIFIED AMINO ACIDS
             AS DEFINED IN THE SPECIFICATION"

(xi) SEQUENCE DESCRIPTION: SEQ ID NO:3:

Cys Xaa Xaa His Glu Leu Tyr Val Xaa Phe Xaa Asp Leu Gly Trp Xaa
1               5                   10                  15

Asp Trp Xaa Ile Ala Pro Xaa Gly Tyr Xaa Ala Tyr Tyr Cys Glu Gly
            20                  25                  30

Glu Cys Xaa Phe Pro Leu Xaa Ser Xaa Met Asn Ala Thr Asn His Ala
        35                  40                  45

Ile Xaa Gln Xaa Leu Val His Xaa Xaa Xaa Pro Xaa Xaa Val Pro Lys
    50                  55                  60

Xaa Cys Cys Ala Pro Thr Xaa Leu Xaa Ala Xaa Ser Val Leu Tyr Xaa
65                  70                  75                  80

Asp Xaa Ser Xaa Asn Val Xaa Leu Xaa Lys Xaa Arg Asn Met Val Val
                85                  90                  95

Xaa Ala Cys Gly Cys His
            100

(2) INFORMATION FOR SEQ ID NO:4:
```

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: Homo sapiens
        (F) TISSUE TYPE: HIPPOCAMPUS (ix) FEATURE:
        (A) NAME/KEY: Protein
        (B) LOCATION: 1..139
        (D) OTHER INFORMATION: /label= hOP1-MATURE (xi) SEQUENCE DESCRIPTION: SEQ ID NO:4:

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
            35                  40                  45

Asp Leu Gly Trp Gln Asp Trp Ile Ile Ala Pro Glu Gly Tyr Ala Ala
            50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
                100                 105                 110

Ser Val Leu Tyr Phe Asp Asp Ser Ser Asn Val Ile Leu Lys Lys Tyr
                115                 120                 125

Arg Asn Met Val Val Arg Ala Cys Gly Cys His
130                 135

(2) INFORMATION FOR SEQ ID NO:5:

(i) SEQUENCE CHARACTERISTICS:
        (A) LENGTH: 139 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: MURIDAE
        (F) TISSUE TYPE: EMBRYO (ix) FEATURE:
        (A) NAME/KEY: Protein
        (B) LOCATION: 1..139
        (D) OTHER INFORMATION: /label= MOP1-MATURE (xi) SEQUENCE DESCRIPTION: SEQ ID NO:5:

Ser Thr Gly Gly Lys Gln Arg Ser Gln Asn Arg Ser Lys Thr Pro Lys
1               5                   10                  15

Asn Gln Glu Ala Leu Arg Met Ala Ser Val Ala Glu Asn Ser Ser Ser
            20                  25                  30

Asp Gln Arg Gln Ala Cys Lys Lys His Glu Leu Tyr Val Ser Phe Arg
            35                  40                  45

Asp Leu Gly Trp Gln Asp Trp Ile Ile Ala Pro Glu Gly Tyr Ala Ala

```
                    50                  55                  60
Tyr Tyr Cys Glu Gly Glu Cys Ala Phe Pro Leu Asn Ser Tyr Met Asn
 65                      70                  75                  80

Ala Thr Asn His Ala Ile Val Gln Thr Leu Val His Phe Ile Asn Pro
                 85                  90                  95

Asp Thr Val Pro Lys Pro Cys Cys Ala Pro Thr Gln Leu Asn Ala Ile
             100                 105                 110

Ser Val Leu Tyr Phe Asp Asp Ser Ser Asn Val Ile Leu Lys Lys Tyr
         115                 120                 125

Arg Asn Met Val Val Arg Ala Cys Gly Cys His
         130                 135
```

(2) INFORMATION FOR SEQ ID NO:6:

(i) SEQUENCE CHARACTERISTICS:
　　　　　(A) LENGTH: 139 amino acids
　　　　　(B) TYPE: amino acid
　　　　　(C) STRANDEDNESS: single
　　　　　(D) TOPOLOGY: linear (ii) MOLECULE TYPE: protein (vi) ORIGINAL SOURCE:
　　　　　(A) ORGANISM: HOMO SAPIENS
　　　　　(F) TISSUE TYPE: HIPPOCAMPUS (ix) FEATURE:
　　　　　(A) NAME/KEY: Protein
　　　　　(B) LOCATION: 1..139
　　　　　(D) OTHER INFORMATION: /label= HOP2-MATURE (xi) SEQUENCE DESCRIPTION: SEQ ID NO:6:

```
Ala Val Arg Pro Leu Arg Arg Arg Gln Pro Lys Lys Ser Asn Glu Leu
 1               5                  10                  15

Pro Gln Ala Asn Arg Leu Pro Gly Ile Phe Asp Asp Val His Gly Ser
             20                  25                  30

His Gly Arg Gln Val Cys Arg Arg His Glu Leu Tyr Val Ser Phe Gln
         35                  40                  45

Asp Leu Gly Trp Leu Asp Trp Val Ile Ala Pro Gln Gly Tyr Ser Ala
 50                  55                  60

Tyr Tyr Cys Glu Gly Glu Cys Ser Phe Pro Leu Asp Ser Cys Met Asn
 65                      70                  75                  80

Ala Thr Asn His Ala Ile Leu Gln Ser Leu Val His Leu Met Lys Pro
                 85                  90                  95

Asn Ala Val Pro Lys Ala Cys Cys Ala Pro Thr Lys Leu Ser Ala Thr
             100                 105                 110

Ser Val Leu Tyr Tyr Asp Ser Ser Asn Asn Val Ile Leu Arg Lys His
         115                 120                 125

Arg Asn Met Val Val Lys Ala Cys Gly Cys His
         130                 135
```

(2) INFORMATION FOR SEQ ID NO:7:

(i) SEQUENCE CHARACTERISTICS:
　　　　　(A) LENGTH: 139 amino acids
　　　　　(B) TYPE: amino acid
　　　　　(C) STRANDEDNESS: single
　　　　　(D) TOPOLOGY: linear (ii) MOLECULE TYPE: protein (vi) ORIGINAL SOURCE:
　　　　　(A) ORGANISM: MURIDAE (F) TISSUE TYPE: EMBRYO (ix) FEATURE:
         (A) NAME/KEY: Protein
         (B) LOCATION: 1..139
         (D) OTHER INFORMATION: /label= MOP2-MATURE (xi) SEQUENCE DESCRIPTION: SEQ ID NO:7:

Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
            20                  25                  30

Arg Gly Arg Glu Val Cys Arg Arg His Glu Leu Tyr Val Ser Phe Arg
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ala Phe Pro Leu Asp Ser Cys Met Asn
65              70                  75                  80

Ala Thr Asn His Ala Ile Leu Gln Ser Leu Val His Leu Met Lys Pro
            85                  90                  95

Asp Val Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135

(2) INFORMATION FOR SEQ ID NO:8:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: bovinae (ix) FEATURE:
         (A) NAME/KEY: Protein
         (B) LOCATION: 1..101
         (D) OTHER INFORMATION: /label= CBMP-2A-FX (xi) SEQUENCE DESCRIPTION: SEQ ID NO:8:

Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45

Ile Val Gln Thr Leu Val Asn Ser Val Asn Ser Lys Ile Pro Lys Ala
    50                  55                  60

Cys Cys Val Pro Thr Glu Leu Ser Ala Ile Ser Met Leu Tyr Leu Asp
65              70                  75                  80

Glu Asn Glu Lys Val Val Leu Lys Asn Tyr Gln Asp Met Val Val Glu
            85                  90                  95

Gly Cys Gly Cys Arg
            100

(2) INFORMATION FOR SEQ ID NO:9:

(i) SEQUENCE CHARACTERISTICS:
        (A) LENGTH: 101 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS
        (F) TISSUE TYPE: hippocampus (ix) FEATURE:
        (A) NAME/KEY: Protein
        (B) LOCATION: 1..101
        (D) OTHER INFORMATION: /label= CBMP-2B-FX (xi) SEQUENCE DESCRIPTION: SEQ ID NO:9:

```
Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
        35                  40                  45

Ile Val Gln Thr Leu Val Asn Ser Val Asn Ser Ile Pro Lys Ala
    50                  55                  60

Cys Cys Val Pro Thr Glu Leu Ser Ala Ile Ser Met Leu Tyr Leu Asp
65                  70                  75                  80

Glu Tyr Asp Lys Val Val Leu Lys Asn Tyr Gln Glu Met Val Val Glu
                85                  90                  95

Gly Cys Gly Cys Arg
            100
```

(2) INFORMATION FOR SEQ ID NO:10:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: DROSOPHILA MELANOGASTER (ix) FEATURE:
        (A) NAME/KEY: Protein
        (B) LOCATION: 1..101
        (D) OTHER INFORMATION: /label= DPP-FX (xi) SEQUENCE DESCRIPTION: SEQ ID NO:10:

```
Cys Arg Arg His Ser Leu Tyr Val Asp Phe Ser Asp Val Gly Trp Asp
1               5                   10                  15

Asp Trp Ile Val Ala Pro Leu Gly Tyr Asp Ala Tyr Tyr Cys His Gly
            20                  25                  30

Lys Cys Pro Phe Pro Leu Ala Asp His Phe Asn Ser Thr Asn His Ala
        35                  40                  45

Val Val Gln Thr Leu Val Asn Asn Asn Asn Pro Gly Lys Val Pro Lys
    50                  55                  60

Ala Cys Cys Val Pro Thr Gln Leu Asp Ser Val Ala Met Leu Tyr Leu
65                  70                  75                  80

Asn Asp Gln Ser Thr Val Val Leu Lys Asn Tyr Gln Glu Met Thr Val
```

```
                   85                  90                  95
Val Gly Cys Gly Cys Arg
            100

(2) INFORMATION FOR SEQ ID NO:11:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: XENOPUS (ix) FEATURE:
         (A) NAME/KEY: Protein
         (B) LOCATION: 1..102
         (D) OTHER INFORMATION: /label= VGL-FX (xi) SEQUENCE DESCRIPTION: SEQ ID NO:11:

Cys Lys Lys Arg His Leu Tyr Val Glu Phe Lys Asp Val Gly Trp Gln
1               5                  10                  15

Asn Trp Val Ile Ala Pro Gln Gly Tyr Met Ala Asn Tyr Cys Tyr Gly
            20                  25                  30

Glu Cys Pro Tyr Pro Leu Thr Glu Ile Leu Asn Gly Ser Asn His Ala
        35                  40                  45

Ile Leu Gln Thr Leu Val His Ser Ile Glu Pro Glu Asp Ile Pro Leu
    50                  55                  60

Pro Cys Cys Val Pro Thr Lys Met Ser Pro Ile Ser Met Leu Phe Tyr
65                  70                  75                  80

Asp Asn Asn Asp Asn Val Val Leu Arg His Tyr Glu Asn Met Ala Val
                85                  90                  95

Asp Glu Cys Gly Cys Arg
            100

(2) INFORMATION FOR SEQ ID NO:12:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
         (A) ORGANISM: MURIDAE (ix) FEATURE:
         (A) NAME/KEY: Protein
         (B) LOCATION: 1..102
         (D) OTHER INFORMATION: /label= VGR-1-FX (xi) SEQUENCE DESCRIPTION: SEQ ID NO:12:

Cys Lys Lys His Glu Leu Tyr Val Ser Phe Gln Asp Val Gly Trp Gln
1               5                  10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Val Met Asn Pro Glu Tyr Val Pro Lys
    50                  55                  60
```

```
Pro Cys Cys Ala Pro Thr Lys Val Asn Ala Ile Ser Val Leu Tyr Phe
65                  70                  75                  80

Asp Asp Asn Ser Asn Val Ile Leu Lys Lys Tyr Arg Asn Met Val Val
                85                  90                  95

Arg Ala Cys Gly Cys His
            100
```

(2) INFORMATION FOR SEQ ID NO:13:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (vi) ORIGINAL SOURCE:
        (A) ORGANISM: Homo sapiens
        (F) TISSUE TYPE: brain (ix) FEATURE:
        (A) NAME/KEY: Protein
        (B) LOCATION: 1..106
        (D) OTHER INFORMATION: /note= "GDF-1 (fx)"

(xi) SEQUENCE DESCRIPTION: SEQ ID NO:13:

```
Cys Arg Ala Arg Arg Leu Tyr Val Ser Phe Arg Glu Val Gly Trp His
1               5                   10                  15

Arg Trp Val Ile Ala Pro Arg Gly Phe Leu Ala Asn Tyr Cys Gln Gly
                20                  25                  30

Gln Cys Ala Leu Pro Val Ala Leu Ser Gly Ser Gly Gly Pro Pro Ala
            35                  40                  45

Leu Asn His Ala Val Leu Arg Ala Leu Met His Ala Ala Ala Pro Gly
50                  55                  60

Ala Ala Asp Leu Pro Cys Cys Val Pro Ala Arg Leu Ser Pro Ile Ser
65                  70                  75                  80

Val Leu Phe Phe Asp Asn Ser Asp Asn Val Val Leu Arg Gln Tyr Glu
                85                  90                  95

Asp Met Val Val Asp Glu Cys Gly Cys Arg
            100                 105
```

(2) INFORMATION FOR SEQ ID NO:14:

(i) SEQUENCE CHARACTERISTICS:
        (A) LENGTH: 5 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:14:

```
Cys Xaa Xaa Xaa Xaa
1               5
```

(2) INFORMATION FOR SEQ ID NO:15:

(i) SEQUENCE CHARACTERISTICS:
        (A) LENGTH: 1822 base pairs
        (B) TYPE: nucleic acid

```
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: HOMO SAPIENS
            (F) TISSUE TYPE: HIPPOCAMPUS (ix) FEATURE:
            (A) NAME/KEY: CDS
            (B) LOCATION: 49..1341
            (C) IDENTIFICATION METHOD: experimental
            (D) OTHER INFORMATION: /function= "OSTEOGENIC PROTEIN"
                /product= "OP1"
                /evidence= EXPERIMENTAL
                /standard_name= "OP1"

(xi) SEQUENCE DESCRIPTION: SEQ ID NO:15:
```

```
GGTGCGGGCC CGGAGCCCGG AGCCCGGGTA GCGCGTAGAG CCGGCGCG ATG CAC GTG         57
                                                     Met His Val
                                                       1

CGC TCA CTG CGA GCT GCG GCG CCG CAC AGC TTC GTG GCG CTC TGG GCA         105
Arg Ser Leu Arg Ala Ala Ala Pro His Ser Phe Val Ala Leu Trp Ala
  5              10                  15

CCC CTG TTC CTG CTG CGC TCC GCC CTG GCC GAC TTC AGC CTG GAC AAC         153
Pro Leu Phe Leu Leu Arg Ser Ala Leu Ala Asp Phe Ser Leu Asp Asn
 20                  25                  30                  35

GAG GTG CAC TCG AGC TTC ATC CAC CGG CGC CTC CGC AGC CAG GAG CGG         201
Glu Val His Ser Ser Phe Ile His Arg Arg Leu Arg Ser Gln Glu Arg
                 40                  45                  50

CGG GAG ATG CAG CGC GAG ATC CTC TCC ATT TTG GGC TTG CCC CAC CGC         249
Arg Glu Met Gln Arg Glu Ile Leu Ser Ile Leu Gly Leu Pro His Arg
             55                  60                  65

CCG CGC CCG CAC CTC CAG GGC AAG CAC AAC TCG GCA CCC ATG TTC ATG         297
Pro Arg Pro His Leu Gln Gly Lys His Asn Ser Ala Pro Met Phe Met
         70                  75                  80

CTG GAC CTG TAC AAC GCC ATG GCG GTG GAG GAG GGC GGC GGG CCC GGC         345
Leu Asp Leu Tyr Asn Ala Met Ala Val Glu Glu Gly Gly Gly Pro Gly
     85                  90                  95

GGC CAG GGC TTC TCC TAC CCC TAC AAG GCC GTC TTC AGT ACC CAG GGC         393
Gly Gln Gly Phe Ser Tyr Pro Tyr Lys Ala Val Phe Ser Thr Gln Gly
100                 105                 110                 115

CCC CCT CTG GCC AGC CTG CAA GAT AGC CAT TTC CTC ACC GAC GCC GAC         441
Pro Pro Leu Ala Ser Leu Gln Asp Ser His Phe Leu Thr Asp Ala Asp
                120                 125                 130

ATG GTC ATG AGC TTC GTC AAC CTC GTG GAA CAT GAC AAG GAA TTC TTC         489
Met Val Met Ser Phe Val Asn Leu Val Glu His Asp Lys Glu Phe Phe
            135                 140                 145

CAC CCA CGC TAC CAC CAT CGA GAG TTC CGG TTT GAT CTT TCC AAG ATC         537
His Pro Arg Tyr His His Arg Glu Phe Arg Phe Asp Leu Ser Lys Ile
        150                 155                 160

CCA GAA GGG GAA GCT GTC ACG GCA GCC GAA TTC CGG ATC TAC AAG GAC         585
Pro Glu Gly Glu Ala Val Thr Ala Ala Glu Phe Arg Ile Tyr Lys Asp
    165                 170                 175

TAC ATC CGG GAA CGC TTC GAC AAT GAG ACG TTC CGG ATC AGC GTT TAT         633
Tyr Ile Arg Glu Arg Phe Asp Asn Glu Thr Phe Arg Ile Ser Val Tyr
180                 185                 190                 195

CAG GTG CTC CAG GAG CAC TTG GGC AGG GAA TCG GAT CTC TTC CTG CTC         681
Gln Val Leu Gln Glu His Leu Gly Arg Glu Ser Asp Leu Phe Leu Leu
                200                 205                 210
```

-continued

```
GAC AGC CGT ACC CTC TGG GCC TCG GAG GAG GGC TGG CTG GTG TTT GAC      729
Asp Ser Arg Thr Leu Trp Ala Ser Glu Glu Gly Trp Leu Val Phe Asp
            215                 220                 225

ATC ACA GCC ACC AGC AAC CAC TGG GTG GTC AAT CCG CGG CAC AAC CTG      777
Ile Thr Ala Thr Ser Asn His Trp Val Val Asn Pro Arg His Asn Leu
            230                 235                 240

GGC CTG CAG CTC TCG GTG GAG ACG CTG GAT GGG CAG AGC ATC AAC CCC      825
Gly Leu Gln Leu Ser Val Glu Thr Leu Asp Gly Gln Ser Ile Asn Pro
            245                 250                 255

AAG TTG GCG GGC CTG ATT GGG CGG CAC GGG CCC CAG AAC AAG CAG CCC      873
Lys Leu Ala Gly Leu Ile Gly Arg His Gly Pro Gln Asn Lys Gln Pro
260                 265                 270                 275

TTC ATG GTG GCT TTC TTC AAG GCC ACG GAG GTC CAC TTC CGC AGC ATC      921
Phe Met Val Ala Phe Phe Lys Ala Thr Glu Val His Phe Arg Ser Ile
                280                 285                 290

CGG TCC ACG GGG AGC AAA CAG CGC AGC CAG AAC CGC TCC AAG ACG CCC      969
Arg Ser Thr Gly Ser Lys Gln Arg Ser Gln Asn Arg Ser Lys Thr Pro
                295                 300                 305

AAG AAC CAG GAA GCC CTG CGG ATG GCC AAC GTG GCA GAG AAC AGC AGC     1017
Lys Asn Gln Glu Ala Leu Arg Met Ala Asn Val Ala Glu Asn Ser Ser
            310                 315                 320

AGC GAC CAG AGG CAG GCC TGT AAG AAG CAC GAG CTG TAT GTC AGC TTC     1065
Ser Asp Gln Arg Gln Ala Cys Lys Lys His Glu Leu Tyr Val Ser Phe
            325                 330                 335

CGA GAC CTG GGC TGG CAG GAC TGG ATC ATC GCG CCT GAA GGC TAC GCC     1113
Arg Asp Leu Gly Trp Gln Asp Trp Ile Ile Ala Pro Glu Gly Tyr Ala
340                 345                 350                 355

GCC TAC TAC TGT GAG GGG GAG TGT GCC TTC CCT CTG AAC TCC TAC ATG     1161
Ala Tyr Tyr Cys Glu Gly Glu Cys Ala Phe Pro Leu Asn Ser Tyr Met
                360                 365                 370

AAC GCC ACC AAC CAC GCC ATC GTG CAG ACG CTG GTC CAC TTC ATC AAC     1209
Asn Ala Thr Asn His Ala Ile Val Gln Thr Leu Val His Phe Ile Asn
                375                 380                 385

CCG GAA ACG GTG CCC AAG CCC TGC TGT GCG CCC ACG CAG CTC AAT GCC     1257
Pro Glu Thr Val Pro Lys Pro Cys Cys Ala Pro Thr Gln Leu Asn Ala
            390                 395                 400

ATC TCC GTC CTC TAC TTC GAT GAC AGC TCC AAC GTC ATC CTG AAG AAA     1305
Ile Ser Val Leu Tyr Phe Asp Asp Ser Ser Asn Val Ile Leu Lys Lys
            405                 410                 415

TAC AGA AAC ATG GTG GTC CGG GCC TGT GGC TGC CAC TAGCTCCTCC          1351
Tyr Arg Asn Met Val Val Arg Ala Cys Gly Cys His
420                 425                 430

GAGAATTCAG ACCCTTTGGG GCCAAGTTTT TCTGGATCCT CCATTGCTCG CCTTGGCCAG   1411

GAACCAGCAG ACCAACTGCC TTTTGTGAGA CCTTCCCCTC CCTATCCCCA ACTTTAAAGG   1471

TGTGAGAGTA TTAGGAAACA TGAGCAGCAT ATGGCTTTTG ATCAGTTTTT CAGTGGCAGC   1531

ATCCAATGAA CAAGATCCTA CAAGCTGTGC AGGCAAAACC TAGCAGGAAA AAAAAACAAC   1591

GCATAAAGAA AAATGGCCGG GCCAGGTCAT TGGCTGGGAA GTCTCAGCCA TGCACGGACT   1651

CGTTTCCAGA GGTAATTATG AGCGCCTACC AGCCAGGCCA CCCAGCCGTG GGAGGAAGGG   1711

GGCGTGGCAA GGGGTGGGCA CATTGGTGTC TGTGCGAAAG GAAAATTGAC CCGGAAGTTC   1771

CTGTAATAAA TGTCACAATA AAACGAATGA ATGAAAAAAA AAAAAAAAA A            1822
```

(2) INFORMATION FOR SEQ ID NO:16:

(i) SEQUENCE CHARACTERISTICS:
        (A) LENGTH: 431 amino acids
        (B) TYPE: amino acid (D) TOPOLOGY: linear (ii) MOLECULE TYPE: protein (xi) SEQUENCE DESCRIPTION: SEQ ID NO:16:

```
Met His Val Arg Ser Leu Arg Ala Ala Ala Pro His Ser Phe Val Ala
 1               5                  10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125

Asp Ala Asp Met Val Met Ser Phe Val Asn Leu Val Glu His Asp Lys
    130                 135                 140

Glu Phe Phe His Pro Arg Tyr His His Arg Glu Phe Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
            180                 185                 190

Ser Val Tyr Gln Val Leu Gln Glu His Leu Gly Arg Glu Ser Asp Leu
        195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
            260                 265                 270

Lys Gln Pro Phe Met Val Ala Phe Phe Lys Ala Thr Glu Val His Phe
    275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
            340                 345                 350

Gly Tyr Ala Ala Tyr Tyr Cys Glu Gly Glu Cys Ala Phe Pro Leu Asn
        355                 360                 365

Ser Tyr Met Asn Ala Thr Asn His Ala Ile Val Gln Thr Leu Val His
    370                 375                 380

Phe Ile Asn Pro Glu Thr Val Pro Lys Pro Cys Cys Ala Pro Thr Gln
```

| | | | | | | | | | | |
|---|---|---|---|---|---|---|---|---|---|---|
|385| | | |390| | | |395| | |400|
|Leu|Asn|Ala|Ile|Ser|Val|Leu|Tyr|Phe|Asp|Asp|Ser|Ser|Asn|Val|Ile|
| | | | |405| | | | |410| | | | |415| |

Leu Lys Lys Tyr Arg Asn Met Val Val Arg Ala Cys Gly Cys His
          420                 425                 430

(2) INFORMATION FOR SEQ ID NO:17:

(i) SEQUENCE CHARACTERISTICS:
        (A) LENGTH: 1873 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: MURIDAE
        (F) TISSUE TYPE: EMBRYO (ix) FEATURE:
        (A) NAME/KEY: CDS
        (B) LOCATION: 104..1393
        (D) OTHER INFORMATION: /function= "OSTEOGENIC PROTEIN"
            /product= "MOP1"
            /note= "MOP1 (CDNA)"

(xi) SEQUENCE DESCRIPTION: SEQ ID NO:17:

```
CTGCAGCAAG TGACCTCGGG TCGTGGACCG CTGCCCTGCC CCCTCCGCTG CCACCTGGGG      60

CGGCGCGGGC CCGGTGCCCC GGATCGCGCG TAGAGCCGGC GCG ATG CAC GTG CGC      115
                                              Met His Val Arg
                                                1
```

TCG CTG CGC GCT GCG GCG CCA CAC AGC TTC GTG GCG CTC TGG GCG CCT      163
Ser Leu Arg Ala Ala Ala Pro His Ser Phe Val Ala Leu Trp Ala Pro
 5                  10                  15                  20

CTG TTC TTG CTG CGC TCC GCC CTG GCC GAT TTC AGC CTG GAC AAC GAG      211
Leu Phe Leu Leu Arg Ser Ala Leu Ala Asp Phe Ser Leu Asp Asn Glu
                 25                  30                  35

GTG CAC TCC AGC TTC ATC CAC CGG CGC CTC CGC AGC CAG GAG CGG CGG      259
Val His Ser Ser Phe Ile His Arg Arg Leu Arg Ser Gln Glu Arg Arg
         40                  45                  50

GAG ATG CAG CGG GAG ATC CTG TCC ATC TTA GGG TTG CCC CAT CGC CCG      307
Glu Met Gln Arg Glu Ile Leu Ser Ile Leu Gly Leu Pro His Arg Pro
     55                  60                  65

CGC CCG CAC CTC CAG GGA AAG CAT AAT TCG GCG CCC ATG TTC ATG TTG      355
Arg Pro His Leu Gln Gly Lys His Asn Ser Ala Pro Met Phe Met Leu
 70                  75                  80

GAC CTG TAC AAC GCC ATG GCG GTG GAG GAG AGC GGG CCG GAC GGA CAG      403
Asp Leu Tyr Asn Ala Met Ala Val Glu Glu Ser Gly Pro Asp Gly Gln
 85                  90                  95                 100

GGC TTC TCC TAC CCC TAC AAG GCC GTC TTC AGT ACC CAG GGC CCC CCT      451
Gly Phe Ser Tyr Pro Tyr Lys Ala Val Phe Ser Thr Gln Gly Pro Pro
                105                 110                 115

TTA GCC AGC CTG CAG GAC AGC CAT TTC CTC ACT GAC GCC GAC ATG GTC      499
Leu Ala Ser Leu Gln Asp Ser His Phe Leu Thr Asp Ala Asp Met Val
        120                 125                 130

ATG AGC TTC GTC AAC CTA GTG GAA CAT GAC AAA GAA TTC TTC CAC CCT      547
Met Ser Phe Val Asn Leu Val Glu His Asp Lys Glu Phe Phe His Pro
    135                 140                 145

CGA TAC CAC CAT CGG GAG TTC CGG TTT GAT CTT TCC AAG ATC CCC GAG      595

-continued

```
Arg Tyr His His Arg Glu Phe Arg Phe Asp Leu Ser Lys Ile Pro Glu
    150                 155                 160

GGC GAA CGG GTG ACC GCA GCC GAA TTC AGG ATC TAT AAG GAC TAC ATC      643
Gly Glu Arg Val Thr Ala Ala Glu Phe Arg Ile Tyr Lys Asp Tyr Ile
165                 170                 175                 180

CGG GAG CGA TTT GAC AAC GAG ACC TTC CAG ATC ACA GTC TAT CAG GTG      691
Arg Glu Arg Phe Asp Asn Glu Thr Phe Gln Ile Thr Val Tyr Gln Val
                185                 190                 195

CTC CAG GAG CAC TCA GGC AGG GAG TCG GAC CTC TTC TTG CTG GAC AGC      739
Leu Gln Glu His Ser Gly Arg Glu Ser Asp Leu Phe Leu Leu Asp Ser
            200                 205                 210

CGC ACC ATC TGG GCT TCT GAG GAG GGC TGG TTG GTG TTT GAT ATC ACA      787
Arg Thr Ile Trp Ala Ser Glu Glu Gly Trp Leu Val Phe Asp Ile Thr
        215                 220                 225

GCC ACC AGC AAC CAC TGG GTG GTC AAC CCT CGG CAC AAC CTG GGC TTA      835
Ala Thr Ser Asn His Trp Val Val Asn Pro Arg His Asn Leu Gly Leu
    230                 235                 240

CAG CTC TCT GTG GAG ACC CTG GAT GGG CAG AGC ATC AAC CCC AAG TTG      883
Gln Leu Ser Val Glu Thr Leu Asp Gly Gln Ser Ile Asn Pro Lys Leu
245                 250                 255                 260

GCA GGC CTG ATT GGA CGG CAT GGA CCC CAG AAC AAG CAA CCC TTC ATG      931
Ala Gly Leu Ile Gly Arg His Gly Pro Gln Asn Lys Gln Pro Phe Met
                265                 270                 275

GTG GCC TTC TTC AAG GCC ACG GAA GTC CAT CTC CGT AGT ATC CGG TCC      979
Val Ala Phe Phe Lys Ala Thr Glu Val His Leu Arg Ser Ile Arg Ser
            280                 285                 290

ACG GGG GGC AAG CAG CGC AGC CAG AAT CGC TCC AAG ACG CCA AAG AAC     1027
Thr Gly Gly Lys Gln Arg Ser Gln Asn Arg Ser Lys Thr Pro Lys Asn
        295                 300                 305

CAA GAG GCC CTG AGG ATG GCC AGT GTG GCA GAA AAC AGC AGC AGT GAC     1075
Gln Glu Ala Leu Arg Met Ala Ser Val Ala Glu Asn Ser Ser Ser Asp
    310                 315                 320

CAG AGG CAG GCC TGC AAG AAA CAT GAG CTG TAC GTC AGC TTC CGA GAC     1123
Gln Arg Gln Ala Cys Lys Lys His Glu Leu Tyr Val Ser Phe Arg Asp
325                 330                 335                 340

CTT GGC TGG CAG GAC TGG ATC ATT GCA CCT GAA GGC TAT GCT GCC TAC     1171
Leu Gly Trp Gln Asp Trp Ile Ile Ala Pro Glu Gly Tyr Ala Ala Tyr
                345                 350                 355

TAC TGT GAG GGA GAG TGC GCC TTC CCT CTG AAC TCC TAC ATG AAC GCC     1219
Tyr Cys Glu Gly Glu Cys Ala Phe Pro Leu Asn Ser Tyr Met Asn Ala
            360                 365                 370

ACC AAC CAC GCC ATC GTC CAG ACA CTG GTT CAC TTC ATC AAC CCA GAC     1267
Thr Asn His Ala Ile Val Gln Thr Leu Val His Phe Ile Asn Pro Asp
        375                 380                 385

ACA GTA CCC AAG CCC TGC TGT GCG CCC ACC CAG CTC AAC GCC ATC TCT     1315
Thr Val Pro Lys Pro Cys Cys Ala Pro Thr Gln Leu Asn Ala Ile Ser
    390                 395                 400

GTC CTC TAC TTC GAC GAC AGC TCT AAT GTC ATC CTG AAG AAG TAC AGA     1363
Val Leu Tyr Phe Asp Asp Ser Ser Asn Val Ile Leu Lys Lys Tyr Arg
405                 410                 415                 420

AAC ATG GTG GTC CGG GCC TGT GGC TGC CAC TAGCTCTTCC TGAGACCCTG       1413
Asn Met Val Val Arg Ala Cys Gly Cys His
                425                 430

ACCTTTGCGG GGCCACACCT TTCCAAATCT TCGATGTCTC ACCATCTAAG TCTCTCACTG    1473

CCCACCTTGG CGAGGAGAAC AGACCAACCT CTCCTGAGCC TTCCCTCACC TCCCAACCGG    1533

AAGCATGTAA GGGTTCCAGA AACCTGAGCG TGCAGCAGCT GATGAGCGCC CTTTCCTTCT    1593

GGCACGTGAC GGACAAGATC CTACCAGCTA CCACAGCAAA CGCCTAAGAG CAGGAAAAAT    1653
```

```
GTCTGCCAGG AAAGTGTCCA GTGTCCACAT GGCCCCTGGC GCTCTGAGTC TTTGAGGAGT    1713

AATCGCAAGC CTCGTTCAGC TGCAGCAGAA GGAAGGGCTT AGCCAGGGTG GGCGCTGGCG    1773

TCTGTGTTGA AGGGAAACCA AGCAGAAGCC ACTGTAATGA TATGTCACAA TAAAACCCAT    1833

GAATGAAAAA AAAAAAAAAA AAAAAAAAAA AAAAGAATTC                          1873
```

(2) INFORMATION FOR SEQ ID NO:18:

(i) SEQUENCE CHARACTERISTICS:
        (A) LENGTH: 430 amino acids
        (B) TYPE: amino acid
        (D) TOPOLOGY: linear (ii) MOLECULE TYPE: protein (xi) SEQUENCE DESCRIPTION: SEQ ID NO:18:

```
Met His Val Arg Ser Leu Arg Ala Ala Ala Pro His Ser Phe Val Ala
  1               5                  10                  15

Leu Trp Ala Pro Leu Phe Leu Leu Arg Ser Ala Leu Ala Asp Phe Ser
                 20                  25                  30

Leu Asp Asn Glu Val His Ser Ser Phe Ile His Arg Arg Leu Arg Ser
             35                  40                  45

Gln Glu Arg Arg Glu Met Gln Arg Glu Ile Leu Ser Ile Leu Gly Leu
         50                  55                  60

Pro His Arg Pro Arg Pro His Leu Gln Gly Lys His Asn Ser Ala Pro
 65                  70                  75                  80

Met Phe Met Leu Asp Leu Tyr Asn Ala Met Ala Val Glu Glu Ser Gly
                 85                  90                  95

Pro Asp Gly Gln Gly Phe Ser Tyr Pro Tyr Lys Ala Val Phe Ser Thr
                100                 105                 110

Gln Gly Pro Pro Leu Ala Ser Leu Gln Asp Ser His Phe Leu Thr Asp
            115                 120                 125

Ala Asp Met Val Met Ser Phe Val Asn Leu Val Glu His Asp Lys Glu
130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
                180                 185                 190

Val Tyr Gln Val Leu Gln Glu His Ser Gly Arg Glu Ser Asp Leu Phe
            195                 200                 205

Leu Leu Asp Ser Arg Thr Ile Trp Ala Ser Glu Glu Gly Trp Leu Val
        210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
                260                 265                 270

Gln Pro Phe Met Val Ala Phe Phe Lys Ala Thr Glu Val His Leu Arg
            275                 280                 285

Ser Ile Arg Ser Thr Gly Gly Lys Gln Arg Ser Gln Asn Arg Ser Lys
        290                 295                 300

Thr Pro Lys Asn Gln Glu Ala Leu Arg Met Ala Ser Val Ala Glu Asn
305                 310                 315                 320
```

```
Ser Ser Ser Asp Gln Arg Gln Ala Cys Lys Lys His Glu Leu Tyr Val
            325                 330                 335

Ser Phe Arg Asp Leu Gly Trp Gln Asp Trp Ile Ile Ala Pro Glu Gly
            340                 345                 350

Tyr Ala Ala Tyr Tyr Cys Glu Gly Glu Cys Ala Phe Pro Leu Asn Ser
            355                 360                 365

Tyr Met Asn Ala Thr Asn His Ala Ile Val Gln Thr Leu Val His Phe
    370                 375                 380

Ile Asn Pro Asp Thr Val Pro Lys Pro Cys Cys Ala Pro Thr Gln Leu
385                 390                 395                 400

Asn Ala Ile Ser Val Leu Tyr Phe Asp Asp Ser Ser Asn Val Ile Leu
            405                 410                 415

Lys Lys Tyr Arg Asn Met Val Val Arg Ala Cys Gly Cys His
            420                 425                 430
```

(2) INFORMATION FOR SEQ ID NO:19:

(i) SEQUENCE CHARACTERISTICS:
        (A) LENGTH: 1723 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: Homo sapiens
        (F) TISSUE TYPE: HIPPOCAMPUS (ix) FEATURE:
        (A) NAME/KEY: CDS
        (B) LOCATION: 490..1696
        (D) OTHER INFORMATION: /function= "OSTEOGENIC PROTEIN"
            /product= "hOP2-PP"
            /note= "hOP2 (cDNA)"

(xi) SEQUENCE DESCRIPTION: SEQ ID NO:19:

```
GGCGCCGGCA GAGCAGGAGT GGCTGGAGGA GCTGTGGTTG GAGCAGGAGG TGGCACGGCA        60

GGGCTGGAGG GCTCCCTATG AGTGGCGGAG ACGGCCCAGG AGGCGCTGGA GCAACAGCTC       120

CCACACCGCA CCAAGCGGTG GCTGCAGGAG CTCGCCCATC GCCCCTGCGC TGCTCGGACC       180

GCGGCCACAG CCGGACTGGC GGGTACGGCG GCGACAGAGG CATTGGCCGA GAGTCCCAGT       240

CCGCAGAGTA GCCCCGGCCT CGAGGCGGTG GCGTCCCGGT CCTCTCCGTC CAGGAGCCAG       300

GACAGGTGTC GCGCGGCGGG GCTCCAGGGA CCGCGCCTGA GGCCGGCTGC CCGCCCGTCC       360

CGCCCCGCCC CGCCGCCCGC CGCCCGCCGA GCCCAGCCTC CTTGCCGTCG GGGCGTCCCC       420

AGGCCCTGGG TCGGCCGCGG AGCCGATGCG CGCCCGCTGA GCGCCCCAGC TGAGCGCCCC       480

CGGCCTGCC ATG ACC GCG CTC CCC GGC CCG CTC TGG CTC CTG GGC CTG           528
           Met Thr Ala Leu Pro Gly Pro Leu Trp Leu Leu Gly Leu
             1               5                  10

GCG CTA TGC GCG CTG GGC GGG GGC GGC CCC GGC CTG CGA CCC CCG CCC         576
Ala Leu Cys Ala Leu Gly Gly Gly Gly Pro Gly Leu Arg Pro Pro Pro
         15                  20                  25

GGC TGT CCC CAG CGA CGT CTG GGC GCG CGC GAG CGC CGG GAC GTG CAG         624
Gly Cys Pro Gln Arg Arg Leu Gly Ala Arg Glu Arg Arg Asp Val Gln
 30                  35                  40                  45

CGC GAG ATC CTG GCG GTG CTC GGG CTG CCT GGG CGG CCC CGG CCC CGC         672
Arg Glu Ile Leu Ala Val Leu Gly Leu Pro Gly Arg Pro Arg Pro Arg
                 50                  55                  60

GCG CCA CCC GCC GCC TCC CGG CTG CCC GCG TCC GCG CCG CTC TTC ATG         720
```

```
                Ala Pro Pro Ala Ala Ser Arg Leu Pro Ala Ser Ala Pro Leu Phe Met
                            65                  70                  75

CTG GAC CTG TAC CAC GCC ATG GCC GGC GAC GAC GAC GAG GAC GGC GCG             768
Leu Asp Leu Tyr His Ala Met Ala Gly Asp Asp Asp Glu Asp Gly Ala
            80                  85                  90

CCC GCG GAG CGG CGC CTG GGC CGC GCC GAC CTG GTC ATG AGC TTC GTT             816
Pro Ala Glu Arg Arg Leu Gly Arg Ala Asp Leu Val Met Ser Phe Val
        95                  100                 105

AAC ATG GTG GAG CGA GAC CGT GCC CTG GGC CAC CAG GAG CCC CAT TGG             864
Asn Met Val Glu Arg Asp Arg Ala Leu Gly His Gln Glu Pro His Trp
110                 115                 120                 125

AAG GAG TTC CGC TTT GAC CTG ACC CAG ATC CCG GCT GGG GAG GCG GTC             912
Lys Glu Phe Arg Phe Asp Leu Thr Gln Ile Pro Ala Gly Glu Ala Val
                130                 135                 140

ACA GCT GCG GAG TTC CGG ATT TAC AAG GTG CCC AGC ATC CAC CTG CTC             960
Thr Ala Ala Glu Phe Arg Ile Tyr Lys Val Pro Ser Ile His Leu Leu
            145                 150                 155

AAC AGG ACC CTC CAC GTC AGC ATG TTC CAG GTG GTC CAG GAG CAG TCC            1008
Asn Arg Thr Leu His Val Ser Met Phe Gln Val Val Gln Glu Gln Ser
        160                 165                 170

AAC AGG GAG TCT GAC TTG TTC TTT TTG GAT CTT CAG ACG CTC CGA GCT            1056
Asn Arg Glu Ser Asp Leu Phe Phe Leu Asp Leu Gln Thr Leu Arg Ala
175                 180                 185

GGA GAC GAG GGC TGG CTG GTG CTG GAT GTC ACA GCA GCC AGT GAC TGC            1104
Gly Asp Glu Gly Trp Leu Val Leu Asp Val Thr Ala Ala Ser Asp Cys
190                 195                 200                 205

TGG TTG CTG AAG CGT CAC AAG GAC CTG GGA CTC CGC CTC TAT GTG GAG            1152
Trp Leu Leu Lys Arg His Lys Asp Leu Gly Leu Arg Leu Tyr Val Glu
                210                 215                 220

ACT GAG GAC GGG CAC AGC GTG GAT CCT GGC CTG GCC GGC CTG CTG GGT            1200
Thr Glu Asp Gly His Ser Val Asp Pro Gly Leu Ala Gly Leu Leu Gly
            225                 230                 235

CAA CGG GCC CCA CGC TCC CAA CAG CCT TTC GTG GTC ACT TTC TTC AGG            1248
Gln Arg Ala Pro Arg Ser Gln Gln Pro Phe Val Val Thr Phe Phe Arg
        240                 245                 250

GCC AGT CCG AGT CCC ATC CGC ACC CCT CGG GCA GTG AGG CCA CTG AGG            1296
Ala Ser Pro Ser Pro Ile Arg Thr Pro Arg Ala Val Arg Pro Leu Arg
255                 260                 265

AGG AGG CAG CCG AAG AAA AGC AAC GAG CTG CCG CAG GCC AAC CGA CTC            1344
Arg Arg Gln Pro Lys Lys Ser Asn Glu Leu Pro Gln Ala Asn Arg Leu
270                 275                 280                 285

CCA GGG ATC TTT GAT GAC GTC CAC GGC TCC CAC GGC CGG CAG GTC TGC            1392
Pro Gly Ile Phe Asp Asp Val His Gly Ser His Gly Arg Gln Val Cys
                290                 295                 300

CGT CGG CAC GAG CTC TAC GTC AGC TTC CAG GAC CTC GGC TGG CTG GAC            1440
Arg Arg His Glu Leu Tyr Val Ser Phe Gln Asp Leu Gly Trp Leu Asp
            305                 310                 315

TGG GTC ATC GCT CCC CAA GGC TAC TCG GCC TAT TAC TGT GAG GGG GAG            1488
Trp Val Ile Ala Pro Gln Gly Tyr Ser Ala Tyr Tyr Cys Glu Gly Glu
        320                 325                 330

TGC TCC TTC CCA CTG GAC TCC TGC ATG AAT GCC ACC AAC CAC GCC ATC            1536
Cys Ser Phe Pro Leu Asp Ser Cys Met Asn Ala Thr Asn His Ala Ile
335                 340                 345

CTG CAG TCC CTG GTG CAC CTG ATG AAG CCA AAC GCA GTC CCC AAG GCG            1584
Leu Gln Ser Leu Val His Leu Met Lys Pro Asn Ala Val Pro Lys Ala
350                 355                 360                 365

TGT TGT GCA CCC ACC AAG CTG AGC GCC ACC TCT GTG CTC TAC TAT GAC            1632
Cys Cys Ala Pro Thr Lys Leu Ser Ala Thr Ser Val Leu Tyr Tyr Asp
                370                 375                 380
```

```
AGC AGC AAC AAC GTC ATC CTG CGC AAA CAC CGC AAC ATG GTG GTC AAG      1680
Ser Ser Asn Asn Val Ile Leu Arg Lys His Arg Asn Met Val Val Lys
        385                 390                 395

GCC TGC GGC TGC CAC T GAGTCAGCCC GCCCAGCCCT ACTGCAG                   1723
Ala Cys Gly Cys His
        400
```

(2) INFORMATION FOR SEQ ID NO:20:

(i) SEQUENCE CHARACTERISTICS:
        (A) LENGTH: 402 amino acids
        (B) TYPE: amino acid
        (D) TOPOLOGY: linear (ii) MOLECULE TYPE: protein (xi) SEQUENCE DESCRIPTION: SEQ ID NO:20:

```
Met Thr Ala Leu Pro Gly Pro Leu Trp Leu Gly Leu Ala Leu Cys
 1               5                  10                  15

Ala Leu Gly Gly Gly Pro Gly Leu Arg Pro Pro Gly Cys Pro
            20                  25                  30

Gln Arg Arg Leu Gly Ala Arg Glu Arg Asp Val Gln Arg Glu Ile
        35                  40                  45

Leu Ala Val Leu Gly Leu Pro Gly Arg Pro Arg Pro Arg Ala Pro Pro
    50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Asp Glu Asp Gly Ala Pro Ala Glu
                85                  90                  95

Arg Arg Leu Gly Arg Ala Asp Leu Val Met Ser Phe Val Asn Met Val
                100                 105                 110

Glu Arg Asp Arg Ala Leu Gly His Gln Glu Pro His Trp Lys Glu Phe
            115                 120                 125

Arg Phe Asp Leu Thr Gln Ile Pro Ala Gly Glu Ala Val Thr Ala Ala
        130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
                165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
        195                 200                 205

Lys Arg His Lys Asp Leu Gly Leu Arg Leu Tyr Val Glu Thr Glu Asp
    210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
                245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
        275                 280                 285

Phe Asp Asp Val His Gly Ser His Gly Arg Gln Val Cys Arg Arg His
    290                 295                 300

Glu Leu Tyr Val Ser Phe Gln Asp Leu Gly Trp Leu Asp Trp Val Ile
305                 310                 315                 320
```

```
Ala Pro Gln Gly Tyr Ser Ala Tyr Tyr Cys Glu Gly Glu Cys Ser Phe
            325                 330                 335

Pro Leu Asp Ser Cys Met Asn Ala Thr Asn His Ala Ile Leu Gln Ser
        340                 345                 350

Leu Val His Leu Met Lys Pro Asn Ala Val Pro Lys Ala Cys Cys Ala
            355                 360                 365

Pro Thr Lys Leu Ser Ala Thr Ser Val Leu Tyr Tyr Asp Ser Ser Asn
370                 375                 380

Asn Val Ile Leu Arg Lys His Arg Asn Met Val Val Lys Ala Cys Gly
385                 390                 395                 400

Cys His (2) INFORMATION FOR SEQ ID NO:21:

(i) SEQUENCE CHARACTERISTICS:
        (A) LENGTH: 1926 base pairs
        (B) TYPE: nucleic acid
        (C) STRANDEDNESS: single
        (D) TOPOLOGY: linear (vi) ORIGINAL SOURCE:
        (A) ORGANISM: MURIDAE
        (F) TISSUE TYPE: EMBRYO (ix) FEATURE:
        (A) NAME/KEY: CDS
        (B) LOCATION: 93..1289
        (D) OTHER INFORMATION: /function= "OSTEOGENIC PROTEIN"
            /product= "mOP2-PP"
            /note= "mOP2 cDNA"

(xi) SEQUENCE DESCRIPTION: SEQ ID NO:21:

GCCAGGCACA GGTGCGCCGT CTGGTCCTCC CCGTCTGGCG TCAGCCGAGC CCGACCAGCT          60

ACCAGTGGAT GCGCGCCGGC TGAAAGTCCG AG ATG GCT ATG CGT CCC GGG CCA          113
                                   Met Ala Met Arg Pro Gly Pro
                                    1               5

CTC TGG CTA TTG GGC CTT GCT CTG TGC GCG CTG GGA GGC GGC CAC GGT          161
Leu Trp Leu Leu Gly Leu Ala Leu Cys Ala Leu Gly Gly Gly His Gly
         10                  15                  20

CCG CGT CCC CCG CAC ACC TGT CCC CAG CGT CGC CTG GGA GCG CGC GAG          209
Pro Arg Pro Pro His Thr Cys Pro Gln Arg Arg Leu Gly Ala Arg Glu
 25                  30                  35

CGC CGC GAC ATG CAG CGT GAA ATC CTG GCG GTG CTC GGG CTA CCG GGA          257
Arg Arg Asp Met Gln Arg Glu Ile Leu Ala Val Leu Gly Leu Pro Gly
 40                  45                  50                  55

CGG CCC CGA CCC CGT GCA CAA CCC GCC GCT GCC CGG CAG CCA GCG TCC          305
Arg Pro Arg Pro Arg Ala Gln Pro Ala Ala Ala Arg Gln Pro Ala Ser
                 60                  65                  70

GCG CCC CTC TTC ATG TTG GAC CTA TAC CAC GCC ATG ACC GAT GAC GAC          353
Ala Pro Leu Phe Met Leu Asp Leu Tyr His Ala Met Thr Asp Asp Asp
             75                  80                  85

GAC GGC GGG CCA CCA CAG GCT CAC TTA GGC CGT GCC GAC CTG GTC ATG          401
Asp Gly Gly Pro Pro Gln Ala His Leu Gly Arg Ala Asp Leu Val Met
             90                  95                 100

AGC TTC GTC AAC ATG GTG GAA CGC GAC CGT ACC CTG GGC TAC CAG GAG          449
Ser Phe Val Asn Met Val Glu Arg Asp Arg Thr Leu Gly Tyr Gln Glu
            105                 110                 115

CCA CAC TGG AAG GAA TTC CAC TTT GAC CTA ACC CAG ATC CCT GCT GGG          497
Pro His Trp Lys Glu Phe His Phe Asp Leu Thr Gln Ile Pro Ala Gly
120                 125                 130                 135

GAG GCT GTC ACA GCT GCT GAG TTC CGG ATC TAC AAA GAA CCC AGC ACC          545
```

-continued

```
Glu Ala Val Thr Ala Ala Glu Phe Arg Ile Tyr Lys Glu Pro Ser Thr
            140                 145                 150

CAC CCG CTC AAC ACA ACC CTC CAC ATC AGC ATG TTC GAA GTG GTC CAA         593
His Pro Leu Asn Thr Thr Leu His Ile Ser Met Phe Glu Val Val Gln
                155                 160                 165

GAG CAC TCC AAC AGG GAG TCT GAC TTG TTC TTT TTG GAT CTT CAG ACG         641
Glu His Ser Asn Arg Glu Ser Asp Leu Phe Phe Leu Asp Leu Gln Thr
            170                 175                 180

CTC CGA TCT GGG GAC GAG GGC TGG CTG GTG CTG GAC ATC ACA GCA GCC         689
Leu Arg Ser Gly Asp Glu Gly Trp Leu Val Leu Asp Ile Thr Ala Ala
        185                 190                 195

AGT GAC CGA TGG CTG CTG AAC CAT CAC AAG GAC CTG GGA CTC CGC CTC         737
Ser Asp Arg Trp Leu Leu Asn His His Lys Asp Leu Gly Leu Arg Leu
200                 205                 210                 215

TAT GTG GAA ACC GCG GAT GGG CAC AGC ATG GAT CCT GGC CTG GCT GGT         785
Tyr Val Glu Thr Ala Asp Gly His Ser Met Asp Pro Gly Leu Ala Gly
                220                 225                 230

CTG CTT GGA CGA CAA GCA CCA CGC TCC AGA CAG CCT TTC ATG GTA ACC         833
Leu Leu Gly Arg Gln Ala Pro Arg Ser Arg Gln Pro Phe Met Val Thr
            235                 240                 245

TTC TTC AGG GCC AGC CAG AGT CCT GTG CGG GCC CCT CGG GCA GCG AGA         881
Phe Phe Arg Ala Ser Gln Ser Pro Val Arg Ala Pro Arg Ala Ala Arg
        250                 255                 260

CCA CTG AAG AGG AGG CAG CCA AAG AAA ACG AAC GAG CTT CCG CAC CCC         929
Pro Leu Lys Arg Arg Gln Pro Lys Lys Thr Asn Glu Leu Pro His Pro
265                 270                 275

AAC AAA CTC CCA GGG ATC TTT GAT GAT GGC CAC GGT TCC CGC GGC AGA         977
Asn Lys Leu Pro Gly Ile Phe Asp Asp Gly His Gly Ser Arg Gly Arg
280                 285                 290                 295

GAG GTT TGC CGC AGG CAT GAG CTC TAC GTC AGC TTC CGT GAC CTT GGC        1025
Glu Val Cys Arg Arg His Glu Leu Tyr Val Ser Phe Arg Asp Leu Gly
                300                 305                 310

TGG CTG GAC TGG GTC ATC GCC CCC CAG GGC TAC TCT GCC TAT TAC TGT        1073
Trp Leu Asp Trp Val Ile Ala Pro Gln Gly Tyr Ser Ala Tyr Tyr Cys
            315                 320                 325

GAG GGG GAG TGT GCT TTC CCA CTG GAC TCC TGT ATG AAC GCC ACC AAC        1121
Glu Gly Glu Cys Ala Phe Pro Leu Asp Ser Cys Met Asn Ala Thr Asn
        330                 335                 340

CAT GCC ATC TTG CAG TCT CTG GTG CAC CTG ATG AAG CCA GAT GTT GTC        1169
His Ala Ile Leu Gln Ser Leu Val His Leu Met Lys Pro Asp Val Val
345                 350                 355

CCC AAG GCA TGC TGT GCA CCC ACC AAA CTG AGT GCC ACC TCT GTG CTG        1217
Pro Lys Ala Cys Cys Ala Pro Thr Lys Leu Ser Ala Thr Ser Val Leu
360                 365                 370                 375

TAC TAT GAC AGC AGC AAC AAT GTC ATC CTG CGT AAA CAC CGT AAC ATG        1265
Tyr Tyr Asp Ser Ser Asn Asn Val Ile Leu Arg Lys His Arg Asn Met
                380                 385                 390

GTG GTC AAG GCC TGT GGC TGC CAC TGAGGCCCCG CCCAGCATCC TGCTTCTACT        1319
Val Val Lys Ala Cys Gly Cys His
            395

ACCTTACCAT CTGGCCGGGC CCCTCTCCAG AGGCAGAAAC CCTTCTATGT TATCATAGCT      1379

CAGACAGGGG CAATGGGAGG CCCTTCACTT CCCCTGCCA CTTCCTGCTA AAATTCTGGT       1439

CTTTCCCAGT TCCTCTGTCC TTCATGGGGT TTCGGGCTA TCACCCCGCC CTCTCCATCC       1499

TCCTACCCCA AGCATAGACT GAATGCACAC AGCATCCCAG AGCTATGCTA ACTGAGAGGT      1559

CTGGGGTCAG CACTGAAGGC CCACATGAGG AAGACTGATC CTTGGCCATC CTCAGCCCAC      1619

AATGGCAAAT TCTGGATGGT CTAAGAAGGC CCTGGAATTC TAAACTAGAT GATCTGGGCT      1679
```

```
CTCTGCACCA TTCATTGTGG CAGTTGGGAC ATTTTTAGGT ATAACAGACA CATACACTTA      1739

GATCAATGCA TCGCTGTACT CCTTGAAATC AGAGCTAGCT TGTTAGAAAA AGAATCAGAG      1799

CCAGGTATAG CGGTGCATGT CATTAATCCC AGCGCTAAAG AGACAGAGAC AGGAGAATCT      1859

CTGTGAGTTC AAGGCCACAT AGAAAGAGCC TGTCTCGGGA GCAGGAAAAA AAAAAAAAAC      1919

GGAATTC                                                                1926
```

(2) INFORMATION FOR SEQ ID NO:22:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:22:

```
Met Ala Met Arg Pro Gly Pro Leu Trp Leu Leu Gly Leu Ala Leu Cys
 1               5                  10                  15

Ala Leu Gly Gly Gly His Gly Pro Arg Pro Pro His Thr Cys Pro Gln
                20                  25                  30

Arg Arg Leu Gly Ala Arg Glu Arg Arg Asp Met Gln Arg Glu Ile Leu
            35                  40                  45

Ala Val Leu Gly Leu Pro Gly Arg Pro Arg Pro Arg Ala Gln Pro Ala
        50                  55                  60

Ala Ala Arg Gln Pro Ala Ser Ala Pro Leu Phe Met Leu Asp Leu Tyr
65                  70                  75                  80

His Ala Met Thr Asp Asp Asp Gly Gly Pro Pro Gln Ala His Leu
                85                  90                  95

Gly Arg Ala Asp Leu Val Met Ser Phe Val Asn Met Val Glu Arg Asp
                100                 105                 110

Arg Thr Leu Gly Tyr Gln Glu Pro His Trp Lys Glu Phe His Phe Asp
            115                 120                 125

Leu Thr Gln Ile Pro Ala Gly Glu Ala Val Thr Ala Ala Glu Phe Arg
130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
                180                 185                 190

Val Leu Asp Ile Thr Ala Ala Ser Asp Arg Trp Leu Leu Asn His His
            195                 200                 205

Lys Asp Leu Gly Leu Arg Leu Tyr Val Glu Thr Ala Asp Gly His Ser
210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
            260                 265                 270

Thr Asn Glu Leu Pro His Pro Asn Lys Leu Pro Gly Ile Phe Asp Asp
        275                 280                 285

Gly His Gly Ser Arg Gly Arg Glu Val Cys Arg Arg His Glu Leu Tyr
    290                 295                 300
```

```
Val Ser Phe Arg Asp Leu Gly Trp Leu Asp Trp Val Ile Ala Pro Gln
305                 310                 315                 320

Gly Tyr Ser Ala Tyr Tyr Cys Glu Gly Glu Cys Ala Phe Pro Leu Asp
                325                 330                 335

Ser Cys Met Asn Ala Thr Asn His Ala Ile Leu Gln Ser Leu Val His
            340                 345                 350

Leu Met Lys Pro Asp Val Val Pro Lys Ala Cys Cys Ala Pro Thr Lys
        355                 360                 365

Leu Ser Ala Thr Ser Val Leu Tyr Tyr Asp Ser Ser Asn Asn Val Ile
370                 375                 380

Leu Arg Lys His Arg Asn Met Val Val Lys Ala Cys Gly Cys His
385                 390                 395
```

(2) INFORMATION FOR SEQ ID NO:23:

(i) SEQUENCE CHARACTERISTICS:
        (A) LENGTH: 1368 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1368
        (D) OTHER INFORMATION: /label= "60A"

(xi) SEQUENCE DESCRIPTION: SEQ ID NO:23:

```
ATG TCG GGA CTG CGA AAC ACC TCG GAG GCC GTT GCA GTG CTC GCC TCC        48
Met Ser Gly Leu Arg Asn Thr Ser Glu Ala Val Ala Val Leu Ala Ser
1               5                   10                  15

CTG GGA CTC GGA ATG GTT CTG CTC ATG TTC GTG GCG ACC ACG CCG CCG        96
Leu Gly Leu Gly Met Val Leu Leu Met Phe Val Ala Thr Thr Pro Pro
                20                  25                  30

GCC GTT GAG GCC ACC CAG TCG GGG ATT TAC ATA GAC AAC GGC AAG GAC        144
Ala Val Glu Ala Thr Gln Ser Gly Ile Tyr Ile Asp Asn Gly Lys Asp
            35                  40                  45

CAG ACG ATC ATG CAC AGA GTG CTG AGC GAG GAC GAC AAG CTG GAC GTC        192
Gln Thr Ile Met His Arg Val Leu Ser Glu Asp Asp Lys Leu Asp Val
        50                  55                  60

TCG TAC GAG ATC CTC GAG TTC CTG GGC ATC GCC GAA CGG CCG ACG CAC        240
Ser Tyr Glu Ile Leu Glu Phe Leu Gly Ile Ala Glu Arg Pro Thr His
65                  70                  75                  80

CTG AGC AGC CAC CAG TTG TCG CTG AGG AAG TCG GCT CCC AAG TTC CTG        288
Leu Ser Ser His Gln Leu Ser Leu Arg Lys Ser Ala Pro Lys Phe Leu
                85                  90                  95

CTG GAC GTC TAC CAC CGC ATC ACG GCG GAG GAG GGT CTC AGC GAT CAG        336
Leu Asp Val Tyr His Arg Ile Thr Ala Glu Glu Gly Leu Ser Asp Gln
            100                 105                 110

GAT GAG GAC GAC GAC TAC GAA CGC GGC CAT CGG TCC AGG AGG AGC GCC        384
Asp Glu Asp Asp Asp Tyr Glu Arg Gly His Arg Ser Arg Arg Ser Ala
        115                 120                 125

GAC CTC GAG GAG GAT GAG GGC GAG CAG CAG AAG AAC TTC ATC ACC GAC        432
Asp Leu Glu Glu Asp Glu Gly Glu Gln Gln Lys Asn Phe Ile Thr Asp
130                 135                 140

CTG GAC AAG CGG GCC ATC GAC GAG AGC GAC ATC ATC ATG ACC TTC CTG        480
Leu Asp Lys Arg Ala Ile Asp Glu Ser Asp Ile Ile Met Thr Phe Leu
145                 150                 155                 160

AAC AAG CGC CAC CAC AAT GTG GAC GAA CTG CGT CAC GAG CAC GGC CGT        528
Asn Lys Arg His His Asn Val Asp Glu Leu Arg His Glu His Gly Arg
                165                 170                 175
```

```
CGC CTG TGG TTC GAC GTC TCC AAC GTG CCC AAC GAC AAC TAC CTG GTG      576
Arg Leu Trp Phe Asp Val Ser Asn Val Pro Asn Asp Asn Tyr Leu Val
            180                 185                 190

ATG GCC GAG CTG CGC ATC TAT CAG AAC GCC AAC GAG GGC AAG TGG CTG      624
Met Ala Glu Leu Arg Ile Tyr Gln Asn Ala Asn Glu Gly Lys Trp Leu
        195                 200                 205

ACC GCC AAC AGG GAG TTC ACC ATC ACG GTA TAC GCC ATT GGC ACC GGC      672
Thr Ala Asn Arg Glu Phe Thr Ile Thr Val Tyr Ala Ile Gly Thr Gly
    210                 215                 220

ACG CTG GGC CAG CAC ACC ATG GAG CCG CTG TCC TCG GTG AAC ACC ACC      720
Thr Leu Gly Gln His Thr Met Glu Pro Leu Ser Ser Val Asn Thr Thr
225                 230                 235                 240

GGG GAC TAC GTG GGC TGG TTG GAG CTC AAC GTG ACC GAG GGC CTG CAC      768
Gly Asp Tyr Val Gly Trp Leu Glu Leu Asn Val Thr Glu Gly Leu His
                245                 250                 255

GAG TGG CTG GTC AAG TCG AAG GAC AAT CAT GGC ATC TAC ATT GGA GCA      816
Glu Trp Leu Val Lys Ser Lys Asp Asn His Gly Ile Tyr Ile Gly Ala
            260                 265                 270

CAC GCT GTC AAC CGA CCC GAC CGC GAG GTG AAG CTG GAC GAC ATT GGA      864
His Ala Val Asn Arg Pro Asp Arg Glu Val Lys Leu Asp Asp Ile Gly
        275                 280                 285

CTG ATC CAC CGC AAG GTG GAC GAC GAG TTC CAG CCC TTC ATG ATC GGC      912
Leu Ile His Arg Lys Val Asp Asp Glu Phe Gln Pro Phe Met Ile Gly
    290                 295                 300

TTC TTC CGC GGA CCG GAG CTG ATC AAG GCG ACG GCC CAC AGC AGC CAC      960
Phe Phe Arg Gly Pro Glu Leu Ile Lys Ala Thr Ala His Ser Ser His
305                 310                 315                 320

CAC AGG AGC AAG CGA AGC GCC AGC CAT CCA CGC AAG CGC AAG AAG TCG     1008
His Arg Ser Lys Arg Ser Ala Ser His Pro Arg Lys Arg Lys Lys Ser
                325                 330                 335

GTG TCG CCC AAC AAC GTG CCG CTG CTG GAA CCG ATG GAG AGC ACG CGC     1056
Val Ser Pro Asn Asn Val Pro Leu Leu Glu Pro Met Glu Ser Thr Arg
            340                 345                 350

AGC TGC CAG ATG CAG ACC CTG TAC ATA GAC TTC AAG GAT CTG GGC TGG     1104
Ser Cys Gln Met Gln Thr Leu Tyr Ile Asp Phe Lys Asp Leu Gly Trp
        355                 360                 365

CAT GAC TGG ATC ATC GCA CCA GAG GGC TAT GGC GCC TTC TAC TGC AGC     1152
His Asp Trp Ile Ile Ala Pro Glu Gly Tyr Gly Ala Phe Tyr Cys Ser
    370                 375                 380

GGC GAG TGC AAT TTC CCG CTC AAT GCG CAC ATG AAC GCC ACG AAC CAT     1200
Gly Glu Cys Asn Phe Pro Leu Asn Ala His Met Asn Ala Thr Asn His
385                 390                 395                 400

GCG ATC GTC CAG ACC CTG GTC CAC CTG CTG GAG CCC AAG AAG GTG CCC     1248
Ala Ile Val Gln Thr Leu Val His Leu Leu Glu Pro Lys Lys Val Pro
                405                 410                 415

AAG CCC TGC TGC GCT CCG ACC AGG CTG GGA GCA CTA CCC GTT CTG TAC     1296
Lys Pro Cys Cys Ala Pro Thr Arg Leu Gly Ala Leu Pro Val Leu Tyr
            420                 425                 430

CAC CTG AAC GAC GAG AAT GTG AAC CTG AAA AAG TAT AGA AAC ATG ATT     1344
His Leu Asn Asp Glu Asn Val Asn Leu Lys Lys Tyr Arg Asn Met Ile
        435                 440                 445

GTG AAA TCC TGC GGG TGC CAT TGA                                     1368
Val Lys Ser Cys Gly Cys His
    450                 455
```

(2) INFORMATION FOR SEQ ID NO:24:

(i) SEQUENCE CHARACTERISTICS:
        (A) LENGTH: 455 amino acids
        (B) TYPE: amino acid (D) TOPOLOGY: linear (ii) MOLECULE TYPE: protein (xi) SEQUENCE DESCRIPTION: SEQ ID NO:24:

```
Met Ser Gly Leu Arg Asn Thr Ser Glu Ala Val Ala Val Leu Ala Ser
 1               5                  10                  15
Leu Gly Leu Gly Met Val Leu Leu Met Phe Val Ala Thr Thr Pro Pro
                20                  25                  30
Ala Val Glu Ala Thr Gln Ser Gly Ile Tyr Ile Asp Asn Gly Lys Asp
            35                  40                  45
Gln Thr Ile Met His Arg Val Leu Ser Glu Asp Asp Lys Leu Asp Val
        50                  55                  60
Ser Tyr Glu Ile Leu Glu Phe Leu Gly Ile Ala Glu Arg Pro Thr His
65                  70                  75                  80
Leu Ser Ser His Gln Leu Ser Leu Arg Lys Ser Ala Pro Lys Phe Leu
                85                  90                  95
Leu Asp Val Tyr His Arg Ile Thr Ala Glu Glu Gly Leu Ser Asp Gln
            100                 105                 110
Asp Glu Asp Asp Asp Tyr Glu Arg Gly His Arg Ser Arg Arg Ser Ala
        115                 120                 125
Asp Leu Glu Glu Asp Glu Gly Glu Gln Gln Lys Asn Phe Ile Thr Asp
    130                 135                 140
Leu Asp Lys Arg Ala Ile Asp Glu Ser Asp Ile Ile Met Thr Phe Leu
145                 150                 155                 160
Asn Lys Arg His His Asn Val Asp Glu Leu Arg His Glu His Gly Arg
                165                 170                 175
Arg Leu Trp Phe Asp Val Ser Asn Val Pro Asn Asp Asn Tyr Leu Val
            180                 185                 190
Met Ala Glu Leu Arg Ile Tyr Gln Asn Ala Asn Glu Gly Lys Trp Leu
        195                 200                 205
Thr Ala Asn Arg Glu Phe Thr Ile Thr Val Tyr Ala Ile Gly Thr Gly
    210                 215                 220
Thr Leu Gly Gln His Thr Met Glu Pro Leu Ser Ser Val Asn Thr Thr
225                 230                 235                 240
Gly Asp Tyr Val Gly Trp Leu Glu Leu Asn Val Thr Glu Gly Leu His
                245                 250                 255
Glu Trp Leu Val Lys Ser Lys Asp Asn His Gly Ile Tyr Ile Gly Ala
            260                 265                 270
His Ala Val Asn Arg Pro Asp Arg Glu Val Lys Leu Asp Asp Ile Gly
        275                 280                 285
Leu Ile His Arg Lys Val Asp Asp Glu Phe Gln Pro Phe Met Ile Gly
    290                 295                 300
Phe Phe Arg Gly Pro Glu Leu Ile Lys Ala Thr Ala His Ser Ser His
305                 310                 315                 320
His Arg Ser Lys Arg Ser Ala Ser His Pro Arg Lys Arg Lys Lys Ser
                325                 330                 335
Val Ser Pro Asn Asn Val Pro Leu Leu Glu Pro Met Glu Ser Thr Arg
            340                 345                 350
Ser Cys Gln Met Gln Thr Leu Tyr Ile Asp Phe Lys Asp Leu Gly Trp
        355                 360                 365
His Asp Trp Ile Ile Ala Pro Glu Gly Tyr Gly Ala Phe Tyr Cys Ser
    370                 375                 380
Gly Glu Cys Asn Phe Pro Leu Asn Ala His Met Asn Ala Thr Asn His
```

```
385                390                395                400
Ala Ile Val Gln Thr Leu Val His Leu Leu Glu Pro Lys Lys Val Pro
                405                410                415

Lys Pro Cys Cys Ala Pro Thr Arg Leu Gly Ala Leu Pro Val Leu Tyr
            420                425                430

His Leu Asn Asp Glu Asn Val Asn Leu Lys Lys Tyr Arg Asn Met Ile
        435                440                445

Val Lys Ser Cys Gly Cys His
    450                455

(2) INFORMATION FOR SEQ ID NO:25:

(i) SEQUENCE CHARACTERISTICS:
        (A) LENGTH: 1674 base pairs
        (B) TYPE: nucleic acid
        (C) STRANDEDNESS: single
        (D) TOPOLOGY: linear (ii) MOLECULE TYPE: protein (ix) FEATURE:
        (A) NAME/KEY: CDS
        (B) LOCATION: 69..1268
        (D) OTHER INFORMATION: /note= "mOP3-PP"

(xi) SEQUENCE DESCRIPTION: SEQ ID NO:25:

GGATCCGCGG CGCTGTCCCA TCCTTGTCGT CGAGGCGTCG CTGGATGCGA GTCCGCTAAA       60

CGTCCGAG ATG GCT GCG CGT CCG GGA CTC CTA TGG CTA CTG GGC CTG GCT      110
         Met Ala Ala Arg Pro Gly Leu Leu Trp Leu Leu Gly Leu Ala
         1               5                  10

CTG TGC GTG TTG GGC GGC GGT CAC CTC TCG CAT CCC CCG CAC GTC TTT       158
Leu Cys Val Leu Gly Gly Gly His Leu Ser His Pro Pro His Val Phe
15                  20                  25                  30

CCC CAG CGT CGA CTA GGA GTA CGC GAG CCC CGC GAC ATG CAG CGC GAG       206
Pro Gln Arg Arg Leu Gly Val Arg Glu Pro Arg Asp Met Gln Arg Glu
                35                  40                  45

ATT CGG GAG GTG CTG GGG CTA GCC GGG CGG CCC CGA TCC CGA GCA CCG       254
Ile Arg Glu Val Leu Gly Leu Ala Gly Arg Pro Arg Ser Arg Ala Pro
            50                  55                  60

GTC GGG GCT GCC CAG CAG CCA GCG TCT GCG CCC CTC TTT ATG TTG GAC       302
Val Gly Ala Ala Gln Gln Pro Ala Ser Ala Pro Leu Phe Met Leu Asp
        65                  70                  75

CTG TAC CGT GCC ATG ACG GAT GAC AGT GGC GGT GGG ACC CCG CAG CCT       350
Leu Tyr Arg Ala Met Thr Asp Asp Ser Gly Gly Gly Thr Pro Gln Pro
    80                  85                  90

CAC TTG GAC CGT GCT GAC CTG ATT ATG AGC TTT GTC AAC ATA GTG GAA       398
His Leu Asp Arg Ala Asp Leu Ile Met Ser Phe Val Asn Ile Val Glu
95                  100                 105                 110

CGC GAC CGT ACC CTG GGC TAC CAG GAG CCA CAC TGG AAG GAA TTC CAC       446
Arg Asp Arg Thr Leu Gly Tyr Gln Glu Pro His Trp Lys Glu Phe His
                115                 120                 125

TTT GAC CTA ACC CAG ATC CCT GCT GGG GAG GCT GTC ACA GCT GCT GAG       494
Phe Asp Leu Thr Gln Ile Pro Ala Gly Glu Ala Val Thr Ala Ala Glu
            130                 135                 140

TTC CGG ATC TAC AAA GAA CCC AGT ACC CAC CCG CTC AAC ACA ACC CTC       542
Phe Arg Ile Tyr Lys Glu Pro Ser Thr His Pro Leu Asn Thr Thr Leu
        145                 150                 155

CAC ATC AGC ATG TTC GAA GTG GTC CAA GAG CAC TCC AAC AGG GAG TCT       590
His Ile Ser Met Phe Glu Val Val Gln Glu His Ser Asn Arg Glu Ser
    160                 165                 170

GAC TTG TTC TTT TTG GAT CTT CAG ACG CTC CGA TCT GGG GAC GAG GGC       638
```

```
Asp Leu Phe Phe Leu Asp Leu Gln Thr Leu Arg Ser Gly Asp Glu Gly
175                 180                 185                 190

TGG CTG GTG CTG GAC ATC ACA GCA GCC AGT GAC CGA TGG CTG CTG AAC         686
Trp Leu Val Leu Asp Ile Thr Ala Ala Ser Asp Arg Trp Leu Leu Asn
                        195                 200                 205

CAT CAC AAG GAC CTA GGA CTC CGC CTC TAT GTG GAA ACC GAG GAT GGG         734
His His Lys Asp Leu Gly Leu Arg Leu Tyr Val Glu Thr Glu Asp Gly
            210                 215                 220

CAC AGC ATA GAT CCT GGC CTA GCT GGT CTG CTT GGA CGA CAA GCA CCA         782
His Ser Ile Asp Pro Gly Leu Ala Gly Leu Leu Gly Arg Gln Ala Pro
                225                 230                 235

CGC TCC AGA CAG CCT TTC ATG GTT GGT TTC TTC AGG GCC AAC CAG AGT         830
Arg Ser Arg Gln Pro Phe Met Val Gly Phe Phe Arg Ala Asn Gln Ser
240                 245                 250

CCT GTG CGG GCC CCT CGA ACA GCA AGA CCA CTG AAG AAG AAG CAG CTA         878
Pro Val Arg Ala Pro Arg Thr Ala Arg Pro Leu Lys Lys Lys Gln Leu
255                 260                 265                 270

AAT CAA ATC AAC CAG CTG CCG CAC TCC AAC AAA CAC CTA GGA ATC CTT         926
Asn Gln Ile Asn Gln Leu Pro His Ser Asn Lys His Leu Gly Ile Leu
                275                 280                 285

GAT GAT GGC CAC GGT TCT CAC GGC AGA GAA GTT TGC CGC AGG CAT GAG         974
Asp Asp Gly His Gly Ser His Gly Arg Glu Val Cys Arg Arg His Glu
                290                 295                 300

CTC TAT GTC AGC TTC CGT GAC CTT GGC TGG CTG GAC TCT GTC ATT GCC        1022
Leu Tyr Val Ser Phe Arg Asp Leu Gly Trp Leu Asp Ser Val Ile Ala
                305                 310                 315

CCC CAG GGC TAC TCC GCC TAT TAC TGT GCT GGG GAG TGC ATC TAC CCA        1070
Pro Gln Gly Tyr Ser Ala Tyr Tyr Cys Ala Gly Glu Cys Ile Tyr Pro
320                 325                 330

CTG AAC TCC TGT ATG AAC TCC ACC AAC CAC GCC ACT ATG CAG GCC CTG        1118
Leu Asn Ser Cys Met Asn Ser Thr Asn His Ala Thr Met Gln Ala Leu
335                 340                 345                 350

GTA CAT CTG ATG AAG CCA GAT ATC ATC CCC AAG GTG TGC TGT GTG CCT        1166
Val His Leu Met Lys Pro Asp Ile Ile Pro Lys Val Cys Cys Val Pro
                355                 360                 365

ACT GAG CTG AGT GCC ATT TCT CTG CTC TAC TAT GAT AGA AAC AAT AAT        1214
Thr Glu Leu Ser Ala Ile Ser Leu Leu Tyr Tyr Asp Arg Asn Asn Asn
                370                 375                 380

GTC ATC CTG CGC AGG GAG CGC AAC ATG GTA GTC CAG GCC TGT GGC TGC        1262
Val Ile Leu Arg Arg Glu Arg Asn Met Val Val Gln Ala Cys Gly Cys
                385                 390                 395

CAC TGAGTCCCTG CCCAACAGCC TGCTGCCATC CCATCTATCT AGTCAGGCCT             1315
His
400

CTCTTCCAAG GCAGGAAACC AACAAAGAGG GAAGGCAGTG CTTTCAACTC CATGTCCACA      1375

TTCACAGTCT TGGCCCTCTC TGTTCTTTTT GCCAAGGCTG AGAAGATGGT CCTAGTTATA      1435

ACCCTGGTGA CCTCAGTAGC CCGATCTCTC ATCTCCCCAA ACTCCCCAAT GCAGCCAGGG      1495

GCATCTATGT CCTTTGGGAT TGGGCACAGA AGTCCAATTT ACCAACTTAT TCATGAGTCA      1555

CTACTGGCCC AGCCTGGACT TGAACCTGGA ACACAGGGTA GAGCTCAGGC TCTTCAGTAT      1615

CCATCAGAAG ATTTAGGTGT GTGCAGACAT GACCACACTC CCCCTAGCAC TCCATAGCC       1674
```

(2) INFORMATION FOR SEQ ID NO:26:

(i) SEQUENCE CHARACTERISTICS:
        (A) LENGTH: 399 amino acids
        (B) TYPE: amino acid
        (D) TOPOLOGY: linear (ii) MOLECULE TYPE: protein (xi) SEQUENCE DESCRIPTION: SEQ ID NO:26:

```
Met Ala Ala Arg Pro Gly Leu Leu Trp Leu Leu Gly Leu Ala Leu Cys
 1               5                  10                  15

Val Leu Gly Gly Gly His Leu Ser His Pro Pro His Val Phe Pro Gln
            20                  25                  30

Arg Arg Leu Gly Val Arg Glu Pro Arg Asp Met Gln Arg Glu Ile Arg
        35                  40                  45

Glu Val Leu Gly Leu Ala Gly Arg Pro Arg Ser Arg Ala Pro Val Gly
    50                  55                  60

Ala Ala Gln Gln Pro Ala Ser Ala Pro Leu Phe Met Leu Asp Leu Tyr
65                  70                  75                  80

Arg Ala Met Thr Asp Asp Ser Gly Gly Thr Pro Gln Pro His Leu
                85                  90                  95

Asp Arg Ala Asp Leu Ile Met Ser Phe Val Asn Ile Val Glu Arg Asp
                100                 105                 110

Arg Thr Leu Gly Tyr Gln Glu Pro His Trp Lys Glu Phe His Phe Asp
            115                 120                 125

Leu Thr Gln Ile Pro Ala Gly Glu Ala Val Thr Ala Ala Glu Phe Arg
130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
                180                 185                 190

Val Leu Asp Ile Thr Ala Ala Ser Asp Arg Trp Leu Leu Asn His His
            195                 200                 205

Lys Asp Leu Gly Leu Arg Leu Tyr Val Glu Thr Glu Asp Gly His Ser
210                 215                 220

Ile Asp Pro Gly Leu Ala Gly Leu Leu Gly Arg Gln Ala Pro Arg Ser
225                 230                 235                 240

Arg Gln Pro Phe Met Val Gly Phe Phe Arg Ala Asn Gln Ser Pro Val
                245                 250                 255

Arg Ala Pro Arg Thr Ala Arg Pro Leu Lys Lys Lys Gln Leu Asn Gln
                260                 265                 270

Ile Asn Gln Leu Pro His Ser Asn Lys His Leu Gly Ile Leu Asp Asp
            275                 280                 285

Gly His Gly Ser His Gly Arg Glu Val Cys Arg Arg His Glu Leu Tyr
290                 295                 300

Val Ser Phe Arg Asp Leu Gly Trp Leu Asp Ser Val Ile Ala Pro Gln
305                 310                 315                 320

Gly Tyr Ser Ala Tyr Tyr Cys Ala Gly Glu Cys Ile Tyr Pro Leu Asn
                325                 330                 335

Ser Cys Met Asn Ser Thr Asn His Ala Thr Met Gln Ala Leu Val His
                340                 345                 350

Leu Met Lys Pro Asp Ile Ile Pro Lys Val Cys Cys Val Pro Thr Glu
            355                 360                 365

Leu Ser Ala Ile Ser Leu Leu Tyr Tyr Asp Arg Asn Asn Val Ile
370                 375                 380

Leu Arg Arg Glu Arg Asn Met Val Val Gln Ala Cys Gly Cys His
385                 390                 395
```

(2) INFORMATION FOR SEQ ID NO:27:

(i) SEQUENCE CHARACTERISTICS:
        (A) LENGTH: 104 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: Protein
        (B) LOCATION: 1..104
        (D) OTHER INFORMATION: /note= "BMP3"

(xi) SEQUENCE DESCRIPTION: SEQ ID NO:27:

```
Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Phe Pro Met Pro Lys Ser Leu Lys Pro Ser Asn His Ala
        35                  40                  45

Thr Ile Gln Ser Ile Val Ala Arg Ala Val Gly Val Val Pro Gly Ile
    50                  55                  60

Pro Glu Pro Cys Cys Val Pro Glu Lys Met Ser Ser Leu Ser Ile Leu
65                  70                  75                  80

Phe Phe Asp Glu Asn Lys Asn Val Val Leu Lys Val Tyr Pro Asn Met
                85                  90                  95

Thr Val Glu Ser Cys Ala Cys Arg
            100
```

(2) INFORMATION FOR SEQ ID NO:28:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Protein
        (B) LOCATION: 1..102
        (D) OTHER INFORMATION: /note= "BMP5"

(xi) SEQUENCE DESCRIPTION: SEQ ID NO:28:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Phe Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Phe Pro Asp His Val Pro Lys
    50                  55                  60

Pro Cys Cys Ala Pro Thr Lys Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ser Cys Gly Cys His
```

(2) INFORMATION FOR SEQ ID NO:29:

(i) SEQUENCE CHARACTERISTICS:
        (A) LENGTH: 102 amino acids
        (B) TYPE: amino acid
        (C) STRANDEDNESS: single
        (D) TOPOLOGY: linear (ii) MOLECULE TYPE: protein (vi) ORIGINAL SOURCE:
        (A) ORGANISM: HOMO SAPIENS (ix) FEATURE:
        (A) NAME/KEY: Protein
        (B) LOCATION: 1..102
        (D) OTHER INFORMATION: /note= "BMP6"

(xi) SEQUENCE DESCRIPTION: SEQ ID NO:29:

```
Cys Arg Lys His Glu Leu Tyr Val Ser Phe Gln Asp Leu Gly Trp Gln
 1               5                  10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
        35                  40                  45

Ile Val Gln Thr Leu Val His Leu Met Asn Pro Glu Tyr Val Pro Lys
    50                  55                  60

Pro Cys Cys Ala Pro Thr Lys Leu Asn Ala Ile Ser Val Leu Tyr Phe
65                  70                  75                  80

Asp Asp Asn Ser Asn Val Ile Leu Lys Lys Tyr Arg Trp Met Val Val
                85                  90                  95

Arg Ala Cys Gly Cys His
            100
```

(2) INFORMATION FOR SEQ ID NO:30:

(i) SEQUENCE CHARACTERISTICS:
        (A) LENGTH: 1247 base pairs
        (B) TYPE: nucleic acid
        (C) STRANDEDNESS: single
        (D) TOPOLOGY: linear (ii) MOLECULE TYPE: cDNA (vi) ORIGINAL SOURCE:
        (A) ORGANISM: HOMO SAPIENS
        (F) TISSUE TYPE: BRAIN (ix) FEATURE:
        (A) NAME/KEY: CDS
        (B) LOCATION: 84..1199
        (D) OTHER INFORMATION: /product= "GDF-1"
            /note= "GDF-1 cDNA"

(xi) SEQUENCE DESCRIPTION: SEQ ID NO:30:

```
GGGGACACCG GCCCCGCCCT CAGCCCACTG GTCCCGGGCC GCCGCGGACC CTGCGCACTC      60

TCTGGTCATC GCCTGGGAGG AAG ATG CCA CCG CCG CAG CAA GGT CCC TGC         110
                         Met Pro Pro Pro Gln Gln Gly Pro Cys
                          1               5

GGC CAC CAC CTC CTC CTC CTC CTG GCC CTG CTG CTG CCC TCG CTG CCC       158
Gly His His Leu Leu Leu Leu Leu Ala Leu Leu Leu Pro Ser Leu Pro
 10              15                  20                  25

CTG ACC CGC GCC CCC GTG CCC CCA GGC CCA GCC GCC GCC CTG CTC CAG       206
Leu Thr Arg Ala Pro Val Pro Pro Gly Pro Ala Ala Ala Leu Leu Gln
```

```
                    30                    35                    40
GCT CTA GGA CTG CGC GAT GAG CCC CAG GGT GCC CCC AGG CTC CGG CCG        254
Ala Leu Gly Leu Arg Asp Glu Pro Gln Gly Ala Pro Arg Leu Arg Pro
                45                    50                    55

GTT CCC CCG GTC ATG TGG CGC CTG TTT CGA CGC GGG GAC CCC CAG GAG        302
Val Pro Pro Val Met Trp Arg Leu Phe Arg Arg Arg Asp Pro Gln Glu
            60                    65                    70

ACC AGG TCT GGC TCG CGG CGG ACG TCC CCA GGG GTC ACC CTG CAA CCG        350
Thr Arg Ser Gly Ser Arg Arg Thr Ser Pro Gly Val Thr Leu Gln Pro
        75                    80                    85

TGC CAC GTG GAG GAG CTG GGG GTC GCC GGA AAC ATC GTG CGC CAC ATC        398
Cys His Val Glu Glu Leu Gly Val Ala Gly Asn Ile Val Arg His Ile
 90                    95                   100                   105

CCG GAC CGC GGT GCG CCC ACC CGG GCC TCG GAG CCT GTC TCG GCC GCG        446
Pro Asp Arg Gly Ala Pro Thr Arg Ala Ser Glu Pro Val Ser Ala Ala
                110                   115                   120

GGG CAT TGC CCT GAG TGG ACA GTC GTC TTC GAC CTG TCG GCT GTG GAA        494
Gly His Cys Pro Glu Trp Thr Val Val Phe Asp Leu Ser Ala Val Glu
            125                   130                   135

CCC GCT GAG CGC CCG AGC CGG GCC CGC CTG GAG CTG CGT TTC GCG GCG        542
Pro Ala Glu Arg Pro Ser Arg Ala Arg Leu Glu Leu Arg Phe Ala Ala
        140                   145                   150

GCG GCG GCG GCA GCC CCG GAG GGC GGC TGG GAG CTG AGC GTG GCG CAA        590
Ala Ala Ala Ala Ala Pro Glu Gly Gly Trp Glu Leu Ser Val Ala Gln
155                   160                   165

GCG GGC CAG GGC GCG GGC GCG GAC CCC GGG CCG GTG CTC CTC CGC CAG        638
Ala Gly Gln Gly Ala Gly Ala Asp Pro Gly Pro Val Leu Leu Arg Gln
170                   175                   180                   185

TTG GTG CCC GCC CTG GGG CCG CCA GTG CGC GCG GAG CTG CTG GGC GCC        686
Leu Val Pro Ala Leu Gly Pro Pro Val Arg Ala Glu Leu Leu Gly Ala
                190                   195                   200

GCT TGG GCT CGC AAC GCC TCA TGG CCG CGC AGC CTC CGC CTG GCG CTG        734
Ala Trp Ala Arg Asn Ala Ser Trp Pro Arg Ser Leu Arg Leu Ala Leu
            205                   210                   215

GCG CTA CGC CCC CGG GCC CCT GCC GCC TGC GCG CGC CTG GCC GAG GCC        782
Ala Leu Arg Pro Arg Ala Pro Ala Ala Cys Ala Arg Leu Ala Glu Ala
        220                   225                   230

TCG CTG CTG CTG GTG ACC CTC GAC CCG CGC CTG TGC CAC CCC CTG GCC        830
Ser Leu Leu Leu Val Thr Leu Asp Pro Arg Leu Cys His Pro Leu Ala
    235                   240                   245

CGG CCG CGG CGC GAC GCC GAA CCC GTG TTG GGC GGC GGC CCC GGG GGC        878
Arg Pro Arg Arg Asp Ala Glu Pro Val Leu Gly Gly Gly Pro Gly Gly
250                   255                   260                   265

GCT TGT CGC GCG CGG CGG CTG TAC GTG AGC TTC CGC GAG GTG GGC TGG        926
Ala Cys Arg Ala Arg Arg Leu Tyr Val Ser Phe Arg Glu Val Gly Trp
                270                   275                   280

CAC CGC TGG GTC ATC GCG CCG CGC GGC TTC CTG GCC AAC TAC TGC CAG        974
His Arg Trp Val Ile Ala Pro Arg Gly Phe Leu Ala Asn Tyr Cys Gln
            285                   290                   295

GGT CAG TGC GCG CTG CCC GTC GCG CTG TCG GGG TCC GGG GGG CCG CCG       1022
Gly Gln Cys Ala Leu Pro Val Ala Leu Ser Gly Ser Gly Gly Pro Pro
        300                   305                   310

GCG CTC AAC CAC GCT GTG CTG CGC GCG CTC ATG CAC GCG GCC GCC CCG       1070
Ala Leu Asn His Ala Val Leu Arg Ala Leu Met His Ala Ala Ala Pro
    315                   320                   325

GGA GCC GCC GAC CTG CCC TGC TGC GTG CCC GCG CGC CTG TCG CCC ATC       1118
Gly Ala Ala Asp Leu Pro Cys Cys Val Pro Ala Arg Leu Ser Pro Ile
330                   335                   340                   345

TCC GTG CTC TTC TTT GAC AAC AGC GAC AAC GTG GTG CTG CGG CAG TAT       1166
```

```
Ser Val Leu Phe Phe Asp Asn Ser Asp Asn Val Val Leu Arg Gln Tyr
                350                 355                 360

GAG GAC ATG GTG GTG GAC GAG TGC GGC TGC CGC TAACCCGGGG CGGGCAGGGA    1219
Glu Asp Met Val Val Asp Glu Cys Gly Cys Arg
            365                 370

CCCGGGCCCA ACAATAAATG CCGCGTGG                                       1247
```

(2) INFORMATION FOR SEQ ID NO:31:

(i) SEQUENCE CHARACTERISTICS:
        (A) LENGTH: 372 amino acids
        (B) TYPE: amino acid
        (D) TOPOLOGY: linear (ii) MOLECULE TYPE: protein (xi) SEQUENCE DESCRIPTION: SEQ ID NO:31:

```
Met Pro Pro Pro Gln Gln Gly Pro Cys Gly His His Leu Leu Leu Leu
 1               5                  10                  15

Leu Ala Leu Leu Leu Pro Ser Leu Pro Leu Thr Arg Ala Pro Val Pro
                20                  25                  30

Pro Gly Pro Ala Ala Ala Leu Leu Gln Ala Leu Gly Leu Arg Asp Glu
            35                  40                  45

Pro Gln Gly Ala Pro Arg Leu Arg Pro Val Pro Pro Val Met Trp Arg
        50                  55                  60

Leu Phe Arg Arg Arg Asp Pro Gln Glu Thr Arg Ser Gly Ser Arg Arg
 65                 70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
                100                 105                 110

Arg Ala Ser Glu Pro Val Ser Ala Ala Gly His Cys Pro Glu Trp Thr
            115                 120                 125

Val Val Phe Asp Leu Ser Ala Val Glu Pro Ala Glu Arg Pro Ser Arg
        130                 135                 140

Ala Arg Leu Glu Leu Arg Phe Ala Ala Ala Ala Ala Ala Ala Pro Glu
145                 150                 155                 160

Gly Gly Trp Glu Leu Ser Val Ala Gln Ala Gly Gln Gly Ala Gly Ala
                165                 170                 175

Asp Pro Gly Pro Val Leu Leu Arg Gln Leu Val Pro Ala Leu Gly Pro
            180                 185                 190

Pro Val Arg Ala Glu Leu Leu Gly Ala Ala Trp Ala Arg Asn Ala Ser
        195                 200                 205

Trp Pro Arg Ser Leu Arg Leu Ala Leu Ala Leu Arg Pro Arg Ala Pro
    210                 215                 220

Ala Ala Cys Ala Arg Leu Ala Glu Ala Ser Leu Leu Leu Val Thr Leu
225                 230                 235                 240

Asp Pro Arg Leu Cys His Pro Leu Ala Arg Pro Arg Arg Asp Ala Glu
                245                 250                 255

Pro Val Leu Gly Gly Gly Pro Gly Gly Ala Cys Arg Ala Arg Arg Leu
            260                 265                 270

Tyr Val Ser Phe Arg Glu Val Gly Trp His Arg Trp Val Ile Ala Pro
        275                 280                 285

Arg Gly Phe Leu Ala Asn Tyr Cys Gln Gly Gln Cys Ala Leu Pro Val
    290                 295                 300

Ala Leu Ser Gly Ser Gly Gly Pro Pro Ala Leu Asn His Ala Val Leu
```

-continued

```
                305                 310                 315                 320
Arg Ala Leu Met His Ala Ala Ala Pro Gly Ala Ala Asp Leu Pro Cys
                    325                 330                 335
Cys Val Pro Ala Arg Leu Ser Pro Ile Ser Val Leu Phe Phe Asp Asn
                340                 345                 350
Ser Asp Asn Val Val Leu Arg Gln Tyr Glu Asp Met Val Val Asp Glu
            355                 360                 365
Cys Gly Cys Arg
    370
```